(12) United States Patent
Bishop et al.

(10) Patent No.: US 11,098,346 B2
(45) Date of Patent: Aug. 24, 2021

(54) SEQUENTIAL DELIVERY OF FLUID VOLUMES AND ASSOCIATED DEVICES, SYSTEMS AND METHODS

(71) Applicant: University of Washington, Seattle, WA (US)

(72) Inventors: Joshua Bishop, Seattle, WA (US); Joshua Buser, Seattle, WA (US); Samantha Byrnes, Seattle, WA (US); Shivani Dharmaraja, Seattle, WA (US); Elain S. Fu, Seattle, WA (US); Jared Houghtaling, Seattle, WA (US); Peter C. Kauffman, Seattle, WA (US); Sujatha Kumar, Seattle, WA (US); Lisa Lafleur, Seattle, WA (US); Tinny Liang, Seattle, WA (US); Barry Lutz, Seattle, WA (US); Bhushan Toley, Seattle, WA (US); Maxwell Wheeler, Seattle, WA (US); Paul Yager, Seattle, WA (US); Xiaohong Zhang, Seattle, WA (US)

(73) Assignee: University of Washington, Seattle, WA (US)

( * ) Notice: Subject to any disclaimer, the term of this patent is extended or adjusted under 35 U.S.C. 154(b) by 177 days.

(21) Appl. No.: 16/059,919

(22) Filed: Aug. 9, 2018

(65) Prior Publication Data
US 2019/0134637 A1    May 9, 2019

Related U.S. Application Data

(63) Continuation of application No. 14/761,604, filed as application No. PCT/US2014/012618 on Jan. 22, 2014, now abandoned.
(Continued)

(51) Int. Cl.
*B01L 7/00* (2006.01)
*C12Q 1/6844* (2018.01)
*B01L 3/00* (2006.01)

(52) U.S. Cl.
CPC .......... *C12Q 1/6844* (2013.01); *B01L 3/5023* (2013.01); *B01L 3/502738* (2013.01);
(Continued)

(58) Field of Classification Search
None
See application file for complete search history.

(56) References Cited

U.S. PATENT DOCUMENTS

| 3,667,607 A | 6/1972 | Brandt |
| 3,811,840 A | 5/1974 | Bauer et al. |

(Continued)

FOREIGN PATENT DOCUMENTS

| CN | 1500555 A | 6/2004 |
| CN | 101008039 A | 8/2007 |

(Continued)

OTHER PUBLICATIONS

Brown, T. Southern Blotting in Current Protocols in Molecular Biology 2.9.1-2.9.20. (Year: 1999).*
(Continued)

*Primary Examiner* — Samuel C Woolwine
(74) *Attorney, Agent, or Firm* — Perkins Coie LLP

(57) ABSTRACT

The present technology is directed to capillarity-based devices for performing chemical processes and associated system and methods. In one embodiment, for example, a device can include a porous receiving element having an input region and a receiving region, a first fluid source and a second fluid source positioned within the input region of the receiving element; wherein the first fluid source is positioned between the second fluid source and the receiving
(Continued)

region, and wherein, when both the first and second fluid sources are in fluid connection with the input region, the device is configured to sequentially deliver the first fluid and the second fluid to the receiving region without leakage.

12 Claims, 42 Drawing Sheets

Related U.S. Application Data

(60) Provisional application No. 61/868,006, filed on Aug. 20, 2013, provisional application No. 61/867,950, filed on Aug. 20, 2013, provisional application No. 61/867,941, filed on Aug. 20, 2013, provisional application No. 61/861,055, filed on Aug. 1, 2013, provisional application No. 61/832,356, filed on Jun. 7, 2013, provisional application No. 61/808,106, filed on Apr. 3, 2013, provisional application No. 61/755,134, filed on Jan. 22, 2013.

(52) U.S. Cl.
CPC .......... *B01L 3/502746* (2013.01); *B01L 7/00* (2013.01); *B01L 7/52* (2013.01); *B01L 2200/0605* (2013.01); *B01L 2300/044* (2013.01); *B01L 2300/069* (2013.01); *B01L 2300/0672* (2013.01); *B01L 2300/0816* (2013.01); *B01L 2300/0825* (2013.01); *B01L 2300/0864* (2013.01); *B01L 2300/0867* (2013.01); *B01L 2300/0887* (2013.01); *B01L 2300/126* (2013.01); *B01L 2300/1827* (2013.01); *B01L 2300/1855* (2013.01); *B01L 2300/1877* (2013.01); *B01L 2400/0406* (2013.01); *B01L 2400/0622* (2013.01); *B01L 2400/0672* (2013.01); *B01L 2400/0683* (2013.01); *Y10T 436/2575* (2015.01)

(56) References Cited

U.S. PATENT DOCUMENTS

| | | |
|---|---|---|
| 4,235,601 A | 11/1980 | Deutsch et al. |
| 4,338,169 A | 7/1982 | Bienvenu et al. |
| 4,632,901 A | 12/1986 | Valkirs et al. |
| 4,647,430 A | 3/1987 | Zweig |
| 4,727,019 A | 2/1988 | Valkirs et al. |
| 4,752,138 A | 6/1988 | Rufer |
| 4,810,470 A | 3/1989 | Burkhardt et al. |
| 4,861,711 A | 8/1989 | Friesen et al. |
| 4,960,691 A | 10/1990 | Gordon et al. |
| 4,987,085 A | 1/1991 | Allen et al. |
| 5,079,142 A | 1/1992 | Coleman et al. |
| 5,110,724 A | 5/1992 | Hewett |
| 5,135,872 A | 8/1992 | Ingalz et al. |
| 5,185,242 A | 2/1993 | Keating et al. |
| 5,198,193 A | 3/1993 | Bunce et al. |
| 5,354,538 A | 10/1994 | Bunce et al. |
| 5,369,007 A | 11/1994 | Kidwell |
| 5,516,488 A | 5/1996 | Bunce et al. |
| 5,540,888 A | 7/1996 | Bunce et al. |
| 5,565,318 A | 10/1996 | Difrancesco et al. |
| 5,593,824 A | 1/1997 | Treml et al. |
| 5,618,494 A | 4/1997 | Bunce et al. |
| 5,705,397 A | 1/1998 | Bunce et al. |
| 5,716,852 A | 2/1998 | Brody et al. |
| 5,736,188 A | 4/1998 | Alcock et al. |
| 5,763,157 A | 6/1998 | Treml et al. |
| 5,801,155 A | 9/1998 | Kutyavin et al. |
| 5,853,670 A | 12/1998 | Bunce |
| 5,916,521 A | 6/1999 | Bunce et al. |
| 5,932,100 A | 8/1999 | Forster et al. |
| 6,007,999 A | 12/1999 | Clark |
| 6,017,767 A | 1/2000 | Chandler |
| 6,084,102 A | 7/2000 | Kutyavin et al. |
| 6,093,869 A | 7/2000 | Roe et al. |
| 6,127,121 A | 10/2000 | Afonina et al. |
| 6,146,589 A | 11/2000 | Chandler |
| 6,168,758 B1 | 1/2001 | Forsberg et al. |
| 6,271,040 B1 | 8/2001 | Buechler |
| 6,303,389 B1 | 10/2001 | Levin et al. |
| 6,312,894 B1 | 11/2001 | Hedgpeth et al. |
| 6,485,906 B2 | 11/2002 | Meyer, Jr. et al. |
| 6,486,308 B2 | 11/2002 | Kutyavin et al. |
| 6,492,346 B1 | 12/2002 | Hedgpeth et al. |
| 6,663,833 B1 | 12/2003 | Stave et al. |
| 6,683,173 B2 | 1/2004 | Dempcy et al. |
| 6,742,661 B1 | 6/2004 | Weigl et al. |
| 6,849,414 B2 | 2/2005 | Guan et al. |
| 6,884,584 B2 | 4/2005 | Hedgpeth et al. |
| 6,949,367 B1 | 9/2005 | Dempcy et al. |
| 6,989,128 B2 | 1/2006 | Alajoki et al. |
| 7,045,610 B2 | 5/2006 | Dempcy et al. |
| 7,112,444 B2 | 9/2006 | Beebe et al. |
| 7,141,429 B2 | 11/2006 | Kamholz et al. |
| 7,179,639 B2 | 2/2007 | Pottathil et al. |
| 7,189,522 B2 | 3/2007 | Esfandiari |
| 7,300,802 B2 | 11/2007 | Paek et al. |
| 7,314,060 B2 | 1/2008 | Chen et al. |
| 7,368,549 B2 | 5/2008 | Dempcy et al. |
| 7,416,892 B2 | 8/2008 | Shen et al. |
| 7,442,557 B1 | 10/2008 | Clark et al. |
| 7,537,733 B2 | 5/2009 | Lappe et al. |
| 7,682,817 B2 | 3/2010 | Cohen et al. |
| 7,715,989 B2 | 5/2010 | Dempcy et al. |
| 7,722,817 B2 | 5/2010 | Lauks et al. |
| 7,794,945 B2 | 9/2010 | Hedgpeth et al. |
| 8,201,765 B2 | 6/2012 | Rajagopal et al. |
| 8,329,777 B2 | 12/2012 | Lawrence et al. |
| 8,399,190 B2 | 3/2013 | Belgrader et al. |
| 8,486,717 B2 | 7/2013 | O'Farrell et al. |
| 8,506,901 B2 | 8/2013 | Chen et al. |
| 8,600,933 B2 | 12/2013 | Rowley et al. |
| 8,685,749 B2 | 4/2014 | Shoemaker et al. |
| 8,845,984 B2 | 9/2014 | Powers et al. |
| 8,900,850 B2 | 12/2014 | Gavalchin et al. |
| 9,101,927 B2 | 8/2015 | Alajem et al. |
| 9,207,236 B2 | 12/2015 | Cary et al. |
| 9,528,987 B2 | 12/2016 | Fridley et al. |
| 9,562,262 B2 | 2/2017 | Peytavi et al. |
| 9,616,424 B2 | 4/2017 | Lee et al. |
| 10,125,388 B2 | 11/2018 | Cooney et al. |
| 2001/0046701 A1 | 11/2001 | Schulte et al. |
| 2002/0085953 A1 | 7/2002 | Parker et al. |
| 2002/0179445 A1 | 12/2002 | Alajoki et al. |
| 2003/0129767 A1 | 7/2003 | Bautista et al. |
| 2004/0152207 A1 | 8/2004 | Nelson et al. |
| 2004/0166021 A1 | 8/2004 | Hsu et al. |
| 2004/0166504 A1 | 8/2004 | Rossier et al. |
| 2006/0090800 A1 | 5/2006 | Banerjee et al. |
| 2006/0160078 A1 | 7/2006 | Cardy et al. |
| 2006/0180469 A1 | 8/2006 | Han et al. |
| 2006/0246600 A1 | 11/2006 | Yang et al. |
| 2007/0020768 A1 | 1/2007 | Rundstrom et al. |
| 2007/0239069 A1 | 10/2007 | Guirguis et al. |
| 2008/0145835 A1 | 6/2008 | Alajem et al. |
| 2008/0220520 A1 | 9/2008 | Palecek et al. |
| 2008/0248098 A1 | 10/2008 | Jin et al. |
| 2009/0004732 A1 | 1/2009 | LaBarre et al. |
| 2009/0011472 A1 | 1/2009 | Nelson et al. |
| 2009/0142229 A1 | 6/2009 | MacDonald et al. |
| 2009/0197296 A1 | 8/2009 | Martin et al. |
| 2009/0298191 A1 | 12/2009 | Whitesides et al. |
| 2010/0143905 A1 | 6/2010 | Lane et al. |
| 2010/0210037 A1 | 8/2010 | Brown et al. |
| 2010/0210038 A1 | 8/2010 | Blatt et al. |
| 2010/0233708 A1 | 9/2010 | Mehra et al. |
| 2011/0070589 A1 | 3/2011 | Belgrader et al. |
| 2011/0070642 A1 | 3/2011 | Cayre et al. |
| 2011/0081641 A1 | 4/2011 | Gould et al. |
| 2011/0123398 A1* | 5/2011 | Carrilho ............ F16K 99/0015 422/68.1 |

(56) References Cited

U.S. PATENT DOCUMENTS

| | | |
|---|---|---|
| 2011/0165559 A1 | 7/2011 | Lane et al. |
| 2011/0189792 A1 | 8/2011 | Reinhartz et al. |
| 2012/0003654 A2 | 1/2012 | Belgrader et al. |
| 2012/0028498 A1 | 2/2012 | Na et al. |
| 2012/0149093 A1 | 6/2012 | Gould et al. |
| 2012/0252008 A1 | 10/2012 | Brown et al. |
| 2012/0270225 A1 | 10/2012 | Wakeley et al. |
| 2012/0288961 A1 | 11/2012 | Yager et al. |
| 2013/0017559 A1 | 1/2013 | Babu et al. |
| 2013/0164193 A1 | 6/2013 | Semenov et al. |
| 2013/0253613 A1 | 9/2013 | Salahovic et al. |
| 2013/0272087 A1 | 10/2013 | Carrera Fabra et al. |
| 2014/0093980 A1 | 4/2014 | Fu |
| 2014/0100102 A1 | 4/2014 | Rajagopal et al. |
| 2014/0227707 A1 | 8/2014 | Yager et al. |
| 2014/0295533 A1 | 10/2014 | Faghri et al. |
| 2014/0370617 A1 | 12/2014 | Madsen et al. |
| 2015/0041316 A1 | 2/2015 | Miki et al. |
| 2015/0057515 A1 | 2/2015 | Wang et al. |
| 2015/0203806 A1 | 7/2015 | Yager et al. |
| 2015/0361487 A1 | 12/2015 | Bishop et al. |
| 2016/0121329 A1 | 5/2016 | Vereshchagina et al. |
| 2016/0310942 A1 | 10/2016 | Yager |
| 2017/0131211 A1 | 5/2017 | Yager |

FOREIGN PATENT DOCUMENTS

| | | |
|---|---|---|
| CN | 102827928 A | 12/2012 |
| EP | 0151783 A2 | 8/1985 |
| EP | 0314499 A1 | 5/1989 |
| EP | 0520756 B1 | 4/1995 |
| GB | 2261284 A | 5/1993 |
| GB | 2410086 A | 7/2005 |
| WO | 97034148 | 9/1997 |
| WO | 2001025789 A1 | 4/2001 |
| WO | 0136974 A1 | 5/2001 |
| WO | 2005069007 A1 | 7/2005 |
| WO | 08049083 A2 | 4/2008 |
| WO | 2009137059 A1 | 11/2009 |
| WO | 2010003188 A1 | 1/2010 |
| WO | 2010102294 A1 | 9/2010 |
| WO | 2010130762 A2 | 11/2010 |
| WO | 2011087813 A2 | 7/2011 |
| WO | 2011115975 A2 | 9/2011 |
| WO | 2012178187 A1 | 12/2012 |
| WO | 2014116756 A1 | 7/2014 |

OTHER PUBLICATIONS

Final Office Action dated Apr. 19, 2019 in U.S. Appl. No. 15/135,461 for Yager et al., filed Apr. 21, 2016, 17 pages.
Non-Final Office Action dated Aug. 19, 2019 in U.S. Appl. No. 15/348,926, 12 pages.
Final Office Action dated Oct. 10, 2019 in U.S. Appl. No. 15/135,461 of Yager, P. et al., filed Apr. 21, 2016, 14 pages.
AA Weaver et al. (Jul. 2013) "Paper analytical devices for fast field screening of beta lactam antibiotics and antituberculosis pharmaceuticals," Analytical Chemistry, 85(13):6453-6460.
Abe et al. "Inkjet-printed Paperfluidic Immuno-chemical Sensing Device" Anal Bioanal Chem (2010) 398, pp. 885-893.
Abe, K. et al. (Sep. 2010) "Inkjet-printed paperfluidic immuno-chemical sensing device," Analytical and Bioanalytical Chemistry, 398(2):885-893.
Agida et al. "Stimuli-Responsive Polymer Brushes for Flow ControlThrough Nanopores" J Funct Biomater, Jun. 2012, 3(2): 239-256. Published online Mar. 26, 2012.
Aiello, AE et al. (Jun. 2006) "Meticillin-resistant *Staphylococcus aureus* among US prisoners and military personnel: review and recommendations for future studies," Lancet Infectious Diseases, 6(6):335-341.
AK Yetisen et al. (Jun. 2013) "Paper-based microfluidic point-of-care diagnostic devices," Lab on a Chip, 13(12):2210-2251.

Alguacil, Juan et al., "Measurement of urine pH for epidemiological studies on bladder cancer", European Journal of Epidemiology, 2007.
Al-Soud, W. et al. (Feb. 2001) "Purification and Characterization of PCR-Inhibitory Copmponents in Blood Cells," Journal of Clinical Microbiology, 39(2):485-493.
An, S. F. et al. (May 1991) "Removal of inhibitor(s) of the polymerase chain reaction from formalin fixed, paraffin wax embedded tissues," Journal of Clinical Pathology, 44:924-927.
Anchordoquy, TJ and Molina, MC (Jan. 2008) "Preservation of DNA," Cell Preservation Technology, 5(4):180-188.
Apilux, A. et al. (Mar. 2010) "Lab-on-paper with dual electrochemical/colorimetric detection for simultaneous determination of gold and iron," Analytical Chemistry, 82(5):1727-1732.
Arai, H. et al. (Feb. 1999) "Evaluation of a rapid immunochromatographic test for detection of antibodies to human immunodeficiency virus," Journal of Clinical Microbiology, 37(2):367-370.
AW Martinez et al. (May 2008) "Simple Telemedicine for Developing Regions: Camera Phones and Paper-Based Microfluidic Devices for Real-Time, Off-Site Diagnosis," Analytical Chemistry, 80(10):3699-3707.
BA Rohrman and R. Richards-Kortum (Sep. 2012) "A paper and plastic device for performing recombinase polymerase amplification of HIV DNA," Lab on a Chip, 12(17):3082-3088.
Ballerini, D. R. et al. (May 2012) "Patterned paper and alternative materials as substrates for low-cost microfluidic diagnostics," Microfluid Nanofluid (2012) 13:769-787.
Bauer, KA et al. (Nov. 2010) "An Antimicrobial Stewardship", Program's Impact with Rapid Polymerase Chain Reaction Methicillin-Resistant *Staphylococcus aureus/S. aureus* Blood Culture Test in Patients with *S. aureus* Bacteremia, Clinical Infectious Diseases, 51(9):1074-1080.
Baum, SE et al. (Feb. 2003) "Methicillin-resistant *Staphylococcus aureus* in an adult military beneficiary population lacking risk factors: Susceptibility to orally available agents," Military Medicine, 168(2):126-130.
Belousov, Y. et al. (Mar. 2004) "Single nucleotide polymorphism genotyping by two colour melting curve analysis using the MGB Eclipse Probe System in challenging sequence environment," Human Genomics, 1(3):209-217.
Bercovici, M. et al. (May 2011) "Rapid Detection of Urinary Tract Infections Using Isotachophoresis of Molecular Beacons," Analytical Chemistry 2011, 83, 4110-4117.
BioSpec Products (accessed Jan. 2015) "Mini-beadbeater-8," available online at: http://www.biospec.com/instructions/minibeadbeater_8.
Bird, Christianne Protein Purification Reagent Market Expands, Genetic Engineering and Biotechnology News (http://www.genengnews.com/gen-articles/protein-purification-reagent-market-expands/3930/), 2011.
BJ Toley et al. (Dec. 2013) "Tunable-delay shunts for paper microfluidic devices," Analytical Chemistry, 85(23):11545-11552.
BJ Toley et al. (Oct. 2015) "Isothermal strand displacement amplification (iSDA): a rapid and sensitive method of nucleic acid amplification for point-of-care diagnosis," Analyst, 140(22):7540-7549.
Blanc, DS et al. (Feb. 2011) "High proportion of wrongly", identified methicillin-resistant *Staphylococcus aureus* carriers by use of a rapid commercial PCR assay due to presence of staphylococcal cassette chromosome element lacking the mecA gene, Journal of Clinical Microbiology, 49(2):722-724.
Borysiak, M. D. et al. (Feb. 2015) "NAIL: Nucleic Acid detection using Isotachophoresis and Loop-mediated isothermal amplification," The Royal Society of Chemistry, Lab on a Chip, 2015, 15, 1697-1707.
Boyd, S. and Yamazaki, H. (May 1996) "Long-term preservation of antibody activity and binding to polyester cloth by dessication," Biotechnology Techniques, 10(5):367-370.
Brenwald, NP et al. (Mar. 2010) "Feasibility study of a real-time PCR test for methicillin-resistant *Staphylococcus aureus* in a point of care setting," Journal of Hospital Infection, 74(3):245-249.

(56) References Cited

OTHER PUBLICATIONS

Bruzewicz, DA et al. (May 2008) "Low-cost printing of poly(dimethylsiloxane) barriers to define microchannels in paper," Analytical Chemistry, 80(9):3387-3392.
Buitink, J. et al. (Aug. 2000) "High Critical Temperature above Tg May Contribute to the Stability of Biological Systems," Biophysical Journal, 79(2):1119-1128.
Buschmann, Michael D. et al., "Chitosans for delivery of nucleic acids", Advanced Drug Delivery Reviews, 2013.
Buser, J.R. et al., "Modelling fluid flow in paper microfluidics: necessary parameters, measurements, and modelling techniques" 2016.
Buser, J.R. et al., "The P-valve: A pressure-based valving system for controlling flow and automating assays in paper microfluidics" 2013.
Byrnes, S.A. et al. (May 2015) "One-step purification and concentration of DNA in porous membranes for point-of-care applications," The Royal Society of Chemistry, Lab on a Chip, 2015, 13 pages.
C. Liu et al. (Aug. 2011) "A self-heating cartridge for molecular diagnostics," Lab on a Chip, 11(16):2686-2692.
Campbell, KM et al. (Sep. 2004) "Risk factors for community-associated", methicillin-resistant *Staphylococcus aureus* infections in an outbreak of disease among military trainees in San Diego, California, in 2002, Journal of Clinical Microbiology, 42(9):4050-4053.
Carpenter, JF et al. (Jan. 1987) "Stabilization of Phosphofructokinase with Sugars during Freeze-Drying—Characterization of Enhanced Protection in the Presence of Divalent-Cations," Biochimica et Biophysica Acta, 923(1):109-115.
Carrilho, E. et al. (Aug. 2009) "Understanding Wax Printing: A Simple Micropatterning Process for Paper-Based Microfluidics," Analytical Chemistry, 81(16):7091-7095.
Carter, DJ and Cary, RB (epub May 2007) "Lateral flow microarrays: a novel platform for rapid nucleic acid detection based on miniaturized lateral flow chromatography," Nucleic Acids Research, 35(10):e74, 11 pp.
Causer, Louise M. et al., "A field evaluation of a new molecular-based point-of-care test for chlamydia and gonorrhoea in remote Aboriginal health services in Australia", Sexual Health, 2015.
CC Boehme et al. (Apr.-May 2011) "Feasibility, diagnostic accuracy, and effectiveness of decentralised use of the Xpert MTB/RIF test for diagnosis of tuberculosis and multidrug resistance: a multicentre implementation study," Lancet, 377(9776):1495-150.
Center for Disease Control (Aug. 2009) "Interim guidance for detection of novel influenza A virus using rapid influenza testing," available at: http://www.cdc.gov/h1n1flu/guidance/rapid_testing.htm.
Chembio Diagnostic Systems, Inc. (Apr. 2009; retrieved Jan. 2015) "Dual Path Platform (DPP*) Technology," available online at: <http://www.chembio.com/newtechnologies.html>.
Chen, H. et al. (Apr. 2012) "A fluidic diode, valves, and a sequential-loading circuit fabricated on layered paper," Lab Chip, 2012, 12, 2909-2913.
Chernesky, M. et al. (Oct. 2002) "Impact of Urine Collection Order on the Ability of Assays to Identify Chlamydia trachomatis Infections in Men," Sexually Transmitted Diseases, 30(4):345-347.
Chickering, HT and Park, JH (Mar. 1919) "*Staphylococcus aureus* pneumonia," Journal of the American Medical Association, 72(9):617-626.
Chin, CD et al. (Jan. 2007) "Lab-on-a-chip devices for global health: past studies and future opportunities," Lab on a Chip, 7(1):41-57.
Cho, IH et al. (Jan. 2010) "Immunogold-silver staining-on-a-chip biosensor based on cross-flow chromatography," Journal of Chromatography B: Analytical Technologies in the Biomedical and Life Sciences, 878(2):271-277.
Cho, JH et al. (Feb. 2006) "Plastic ELISA-on-a-chip based on sequential cross-flow chromatography," Analytical Chemistry, 78(3):793-800.

Chun, P. (2009; retrieved Mar. 2016) "Colloidal Gold and Other Labels for Lateral Flow Immunoassays," in Lateral Flow Immunoassay, eds. R. Wong and H. Tse, Humana Press: New York, pp. 75-94.
Co, EM et al. (Jan. 2011) "Prevalence of Methicillin-Resistant *Staphylococcus aureus* in a Combat Support Hospital in Iraq," Military Medicine, 176(1):89-93.
Corstjens, P. et al. (Jan. 2003) "Lateral-flow and up-converting phosphor reporters to detect single-stranded nucleic acids in a sandwich-hybridization assay," Analytical Biochemistry, 312(2):191-200.
Corstjens, P., et al. (Oct. 2001) "Use of up-converting", phosphor reporters in lateral-flow assays to detect specific nucleic acid sequences: A rapid, sensitive DNA test to identify human papillomavirus type 16 infection, Clinical Chemistry, 47(10):1885-1893.
Cretich, M. et al. (Feb. 2010) "Coating of nitrocellulose for colorimetric DNA microarrays," Analytical Biochemistry, 397(1):84-88.
Crowe, LM et al. (Oct. 1996) "Is trehalose special for preserving dry biomaterials?" Biophysical Journal, 71(4):2087-2093.
Crum, NF et al. (Nov. 2006) "Fifteen-year study of the changing epidemiology of methicillin-resistant *Staphylococcus aureus*," American Journal of Medicine, 119(11):943-951.
Cuervo, A. et al., "Direct measurement of the dielectric polarization properties of DNA", Proc Natl Acad Sci, 2014.
D. Di Carlo et al. (Aug. 2003) "Reagentless mechanical cell lysis by nanoscale barbs in microchannels for sample preparation," Lab on a Chip, 3(4):287-291.
Debye, P. et al., "The theory of electrolyes I. The lowering of the freezing point and related occurrences.", Phys Zeitschrift (http://www.chemteam.info/Chem-History/Debye-Strong-Electrolyte.html), 1923.
Desai, D. et al. (Jan. 2011) "Tackling HIV through robust diagnostics in the developing world: current status and future opportunities," Lab on a Chip, 11(2):194-211.
Dharmaraja, S. et al. (2013) "Programming paper networks for point of care diagnostics," Proc. of SPIE, vol. 8615, 11 pages.
Diagnostics for All (2010; retrieved Mar. 2016) "Diagnostics for All: Patterned-paper microfluidics as a low-cost platform for advanced point-of-care diagnostics in low-resource settings," available at http://www.dfa.org/index.html, 1 page.
Drexler, JF et al. (Oct. 2009) "Poor Clinical Sensitivity of Rapid Antigen Test for Influenza A Pandemic (H1N1) 2009 Virus," Emerging Infectious Diseases, 15(10):1662-1664.
Dungchai et al. "Use of Multiple Colorimetric Indicators for Paper-based Microfluidic Devices" Analytica Chimica Acta (2010) 674, pp. 227-233.
Dungchai, W. et al. (Aug. 2010) "Use of multiple colorimetric indicators for paper-based microfluidic devices," Analytica Chimica Acta, 674(2):227-233.
Eddington, DT and Beebe, DJ (Feb. 2004) "Flow control with hydrogels," Advanced Drug Delivery Reviews, 56(2):199-210.
Edwards, KA and Baeumner, AJ (Nov. 2006) "Optimization of DNA-tagged dye-encapsulating liposomes for lateral-flow assays based on sandwich hybridization," Analytical and Bioanalytical Chemistry, 386(5):1335-1343.
Eijkel, Jan C.T. (Nov. 2006) "Young 4ever—the use of capillarity for passive flow handling in lab on a chip devices," Lab on a Chip, 6(11):1405-1408.
Elias, ME and Elias, AM (Dec. 1999) "Trehalose + water fragile system: properties and glass transition," Journal of Molecular Liquids, 83(1-3):303-310.
Ellis, MW et al. (Oct. 2004) "Natural history of community-acquired methicillin-resistant *Staphylococcus aureus* colonization and infection in soldiers," Clinical Infectious Diseases, 39(7):971-979.
Engler, K.H. et al. (Jan. 2002) "Immunochromatographic strip test for rapid detection of diphtheria toxin: Description and multicenter evaluation in areas of low and high prevalence of diphtheria," Journal of Clinical Microbiology, 40(1):80-83.
Englund, JA (2001; retrieved Mar. 2016) "Diagnosis and Epidemiology of Community-Acquired Respiratory Virus Infections in the Immunocompromised Host," Biology of Blood and Marrow Transplantation, 7(Suppl):2S-4S.

(56) References Cited

OTHER PUBLICATIONS

Fairchok, MP et al. (Sep. 2010) "Epidemiology of viral respiratory tract infections in a prospective cohort of infants and toddlers attending daycare," Journal of Clinical Virology, 49(1):16-20.

Farzamfar, B. et al. (2007; retrieved Mar. 2016) "The effect of", different stabilizers on stability of horseradish peroxidase-bovine serum albumin-aflatoxin B1, a conjugated tracer for detection of aflatoxin B1 in immunoassay-based methods, Iranian Journal of Pharmaceutical Research, 6(3):179-184.

Faulstich, K. et al. (2009; retrieved Mar. 2016) "Handheld and Portable Reader Devices for Lateral Flow Immunoassays," in Lateral Flow Immunoassay, eds. R. Wong and H. Tse, Humana Press: New York, pp. 157-183.

Fenton et al. "Multiplex Lateral-Flow Test Strips Fabricated by Two-Dimensional Shaping" ACS Applied Materials & Interfaces, vol. 1, No. 1, 2009, pp. 124-129.

Fenton, E. M. et al. (2009) "Multiplex Lateral-Flow Test Strips Fabricated by Two-Dimensional Shaping," Applied Materials & Interfaces vol. 1, No. 1, 124-129.

Fenton, EM et al. (Jan. 2009) "Multiplex lateral-flow test strips fabricated by two-dimensional shaping," Applied Materials and Interfaces, 1(1):124-129.

Final Office Action dated Aug. 25, 2016 in U.S. Appl. No. 14/601,966 of Yager, P. et al., filed Jan. 21, 2015.

Final Office Action dated Feb. 24, 2017 in U.S. Appl. No. 13/518,365, 16 pages.

Final Office Action dated Feb. 24, 2017 in U.S. Appl. No. 13/518,365, of Yager, P. et al., filed Jun. 21, 2012.

Final Office Action dated Jul. 27, 2017 in U.S. Appl. No. 14/043,664 of Fu, E., et al., filed Oct. 1, 2013.

Foley, JO et al. (Apr. 2008) "Experimental and model investigation of the time-dependent 2-dimensional distribution of binding in a herringbone microchannel," Lab on a Chip, 8(4):557-564.

Foley, JO et al. (May 2007) "Concentration gradient immunoassay. 2. Computational modeling for analysis and optimization," Analytical Chemistry, 79(10):3549-3553.

Fornera, S. et al. (Aug. 2011) "Immobilization of Peroxidase on SiO(2) Surfaces with the Help of a Dendronized Polymer and the Avidin-Biotin System," Macromolecular Bioscience, 11(8):1052-1067.

Fridley, G. E. et al. (Aug. 2012) "Controlled release of dry reagents in porous media for tunable temporal and spatial distribution upon rehydration," Lab Chip, 2012, 12, 4321-4327.

Fridley, Gina E. et al., "Controlled release of dry reagents in porous media for tunable temporal and spatial distribution upon rehydration", Lab Chip, 2012.

Fu et al. "A Two-Dimensional Paper Network Format that Enables Simple Multi-step Assays for Use in Low-resource Settings in the Context of Malaria Antigen Detection" Anal Chem (May 15, 2012) 84(10) pp. 4574-4579.

Fu et al. "Chemical Signal Amplification in Two-Dimensional Paper Networks" Sens Actuators B Chem, (Aug. 6, 2010) 149(1), pp. 325-328.

Fu et al. "Controlled Reagent Transport in Disposable 2D Paper Networks" Lab Chip (Apr. 7, 2010) 10(7), pp. 918-920.

Fu et al. "Enhanced Sensitivity of Lateral Flow Tests Using a Two-Dimensional Paper Network Format" Anal. Chem. (Oct. 15, 2011) 83(20), pp. 7941-7946.

Fu et al. "Transport in Two-Dimesional Paper Networks" Microfluid Nanofluidics (Jan. 2011) 10(1), pp. 29-35.

Fu et al. "Two-Dimensional Paper Network Format That Enables Simple Multistep Assays for Use in Low-Resource Settings in the Context of Malaria Antigen Detection" ACS Publications, (2012) 84, pp. 4574-4579.

Fu, E. Et al. "Two-dimensional paper network format for amplified lateral flow assays" 5th International Conference on Miniaturized Systems for Chemistry and Life Sciences, 2011, vol. 3, pp. 1891-1893.

Fu, E. et al. (Aug. 2010) "Chemical signal amplification in two-dimensional paper networks," Sensors and Actuators B-Chemical, 149(1):325-328.

Fu, E. et al. (epub Jan. 2010) "Controlled reagent transport in disposable 2D paper networks," Lab on a Chip, 10(7):918-920.

Fu, E. et al. (Jan. 2011) "Transport in two-dimensional paper networks," Microfluid Nanofluidics Jan. 2011: 10(1):29-35.

Fu, E. et al. (Jan. 2011) "Transport in two-dimensional paper networks," Microfluidics and Nanofluidics, 10(1):29-35.

Fu, E. et al. (Jun. 2010) "Chemical signal amplification in two-dimensional paper networks," Sensors and Actuators B-149 (2010) 325-328).

Fu, E. et al. (May 2009) "Modeling of a Competitive Microfluidic Heterogeneous Immunoassay: Sensitivity of the Assay Response to Varying System Parameters," Analytical Chemistry, 81(9):3407-3413.

Fu, E. et al. (May 2012) "Two-Dimensional Paper Network Format That Enables Simple Multistep Assays for USE in Low-Resource Settings in the Context of Malaria Antigen Detection," Analytical Chemistry, 2012, 84, 4574-4579.

Fu, E. et al. (May 2012) "A two-dimensional paper network format that enables simple multi-step assays for use in low-resource settings," Analytical Chemistry, 84(10):4574-4579.

Fu, E. et al. (Oct. 2011) "Enhanced Sensitivity of Lateral Flow Tests Using a Two-Dimensional Paper Network Format," Analytical Chemistry, 83(20):7941-7946.

Fu, E. et al. (Sep. 2011) "Enhanced Sensitivity of Lateral Flow Tests Using a Two-Dimensional Paper Network Format," Analytical Chemistry, 2011, 83, 7941-7946.

Fu, E. et al., "Microfluidics 2.0" Presentation, available at http://depts.washington.edu/cpac/Activities/Meetings/Fall/2010/documents/YagerCPACtalkNov2010.pdf, Nov. 11, 2010.

Fu, Elain et al. (epub Jan. 2010) "Controlled reagent transport in disposable 2D paper networks," Lab on a Chip, 10(7):918-920.

GE Healthcare Life Sciences (Apr. 2009; retrieved Jan. 2015) "Whatman Filters & Sample Collection," available online at: http://www.whatman.com/References/FINAL%20FTAProtect&StorageDNADataSheet%204-30-09LR.pdf.

Gerbers, Roman et al., "A new paper-based platform technology for point-of-care diagnostics", The Royal Society of Chemistry, 2014.

Gervais, L. and Delamarche, E. (Dec. 2009) "Toward one-step point-of-care immunodiagnostics using capillary-driven microfluidics and PDMS substrates," Lab on a Chip, 9(23):3330-3337.

Gervais, L. et al. (Aug. 2009) "Toward on-step point-of-care immunodiagnostics using capillary-driven microfluidics and PDMS substrates," Lab Chip, 2009, 9, 3330-3337.

Gervais, L. et al. (Jun. 2011) "Capillary-driven multiparametric microfluidic chips for one-step immunoassays," Biosensors and Bioeletronics 27 (2011) 64-70.

Gibson, TD et al. (Jul. 1993) "Preservation of Shelf-Life of Enzyme-Based Analytical Systems Using a Combination of Sugars, Sugar Alcohols and Cationic Polymers of Zinc Ions," Analytical Chimica Acta, 279(1):185-192.

Gill, P. et al., "Nucleic acid isothermal amplification technologies: a review", Nucleosides, Nucleotides & Nucleic Acids, Mar. 2008, 27(3):224-243.

Govindarajan, A. et al. (Jan. 2011) "Microfluidic origami for", point-of-care extraction of nucleic acids from viscous samples, In Proceedings of the IEEE 24th International Conference on Micro Electrical Mechanical Systems (MEMS '11), Cancun, Mexico, pp. 932-935.

H. Kaneko et al. (Apr. 2007) "Tolerance of loop-mediated isothermal amplification to a culture medium and biological substances," Journal of Biochemical and Biophysical Methods, 70(3):499-501.

H. Lu et al. (Jan. 2005) "A microfluidic electroporation device for cell lysis," Lab on a Chip, 5(1):23-29.

H. Tani et al. (Feb. 2007) "Quantitative method for specific nucleic acid sequences using competitive polymerase chain reaction with an alternately binding probe," Analytical Chemistry, 79(3):974-979.

Horton, JK et al. (Jun. 1991) "A novel, rapid, single-step immunochromatographic procedure for the detection of mouse immunoglobulin," Journal of Immunological Methods, 140(1):131-134.

(56) References Cited

OTHER PUBLICATIONS

Huang, XZ et al. (Jul. 2011) "Methicillin-resistant *Staphylococcus aureus* infection in combat support hospitals in three regions of Iraq," Epidemiology and Infection, 139(7):994-997.
Hurt, AC et al. (Jun. 2007) "Performance of six influenza rapid tests in detecting human influenza in clinical specimens," Journal of Clinical Virology, 39(2):132-135.
Hymas, W. et al. (Aug. 2010) "Development of a multiplex real-time RT-PCR assay for detection of influenza A, influenza B, RSV and typing of the 2009-H1N1 influenza virus," Journal of Virological Methods, 167(2):113-118.
International Search Report and Written Opinion dated Jun. 9, 2011 for PCT/US2010/061675 filed Dec. 21, 2010, 18 pages.
International Search Report and Written Opinion dated Nov. 7, 2012 for International Patent Application No. PCT/US2012/044060 filed Jun. 25, 2012.
International Search Report and Written Opinion dated May 14, 2014 for PCT/US2014/012618 filed Jan. 22, 2014, 17 pages.
International Search Report and Written Opinion for Application No. PCT/US2010/061675 dated Jun. 9, 2011.
Izutsu, KI et al. (Jul. 1994) "Physical Stability and Protein Stability of Freeze-Dried Cakes during Storage at Elevated-Temperatures," Pharmaceutical Research, 11(7):995-999.
J. Jacobs et al. (Dec. 2009) "Influence of environmental gradients on the abundance and distribution of *Mycobacterium* spp. in a coastal lagoon estuary," Applied and Environmental Microbiology, 75(23):7378-7384.
J. Kim et al. (Aug. 2004) "Cell lysis on a microfluidic CD (compact disc)," Lab on a Chip, 4(5):516-522.
J. Kim et al. (Aug. 2009) "Microfluidic sample preparation: cell lysis and nucleic acid purification," Integrative Biology, 1(10):574-586.
J. Siegrist et al. (Feb. 2010) "Validation of a centrifugal microfluidic sample lysis and homogenization platform for nucleic acid extraction with clinical samples," Lab on a Chip, 10(3):363-371.
J. Singleton et al. (Mar. 2013) "Instrument-free exothermic heating with phase change temperature control for paper microfluidic devices," Proceedings of SPIE—International Society for Optical Engineering, 8615:86150R.
Jain, R. et al. (Apr. 2011) "Veterans Affairs Initiative to Prevent Methicillin-Resistant *Staphylococcus aureus* Infections," New England Journal of Medicine, 364(15):1419-1430.
JR Buser et al. (epub Mar. 2015) "Electromechanical cell lysis using a portable audio device: enabling challenging sample preparation at the point-of-care," Lab on a Chip, 15(9):1994-1997.
Juncker, D. et al. (Dec. 2002) "Autonomous microfluidic capillary system," Analytical Chemistry, 74(24):6139-6144.
Juncker, David (May 2002) "Capillary microfluidic systems for bio/chemistry," Ph.D. Thesis, Université de Neuchâtel Faculté0 des sciences, Switzerland, 97 pages.
Kallen, AJ et al. (Mar. 2000) "Increase in community-acquired methicillin-resistant *Staphylococcus aureus* at a Naval Medical Center," Infection Control and Hospital Epidemiology, 21(3):223-226.
Kalogianni, DP et al. (May 2011) "Carbon nano-strings as reporters in lateral flow devices for DNA sensing by hybridization," Analytical and Bioanalytical Chemistry, 400(4):1145-1152.
Kauffman et al. "Visualization and Measurement of Flow in Two-Dimensional Paper Networks" Lab Chip, (Oct. 7, 2010) 10(19) pp. 2614-2617.
Kauffman, P. et al. (Jun. 2010) "Visualization and measurement of flow in two-dimensional paper networks," Lab Chip, 2010, 10, 2614-2617.
Kauffman, P. et al. (Oct. 2010) "Visualization and measurement of flow in two-dimensional paper networks," Lab on a Chip, 10(19):2614-2617.
Kay, M. et al. (Apr. 2011) "Shedding of Pandemic (H1N1) 2009 Virus among Health Care Personnel, Seattle, Washington, USA," Emerging Infectious Diseases, 17(4):639-644.
Kayitmazer, A. B. et al., "Role of Polyelectrolyte Persistence Length in the Binding of Oppositely Charged Micelles, Dendrimers, and Protein to Chitosan and Ploy", Macromolecules, 2005.
Kenner, J. et al. (Jun. 2003) "Rates of carriage of methicillin-resistant and methicillin-susceptible *Staphylococcus aureus* in an outpatient population," Infection Control and Hospital Epidemiology, 24(6):439-444.
Kettler et al. "Mapping the Landscape of Diagnostics for Sexually Transmitted Infections" Special Programme for Research and training in Tropical Diseases (TDR), pp. 1-36.
Kettler, H. et al. (2004; retrieved Mar. 2016) "Mapping the landscape of diagnosis for sexually transmitted infections," World Health Organization on behalf of the Special Programme for Research and Training in Tropical Diseases (TDR), 44 pp.
Kifude, CM et al. (Jun. 2008) "Enzyme-linked immunosorbent assay for detection of Plasmodium falciparum histidine-rich protein 2 in blood, plasma, and serum," Clinical and Vaccine Immunology, 15(6):1012-1018.
Klevens, RM et al. (Oct. 2007) "Invasive methicillin-resistant *Staphylococcus aureus* infections in the United States," JAMA—Journal of the American Medical Association, 298(15):1763-1771.
Kline, MC et al. (Apr. 2002) "Polymerase chain reaction amplification of DNA from aged blood stains: Quantitative evaluation of the "suitability for purpose" of four filter papers as archival media," Analytical Chemistry, 74(8):1863-1869.
Ko, Jong Soo et al. (Oct. 2003) "Polymer-Based microfluidic device for immunosensing LOC (Lab-on-a-Chip)," 7th International Conference on Miniaturized Chemical and Biochemical Analysts Systems, pp. 295-298.
Kolosova, AY et al. (Feb. 2007) "Investigation of several parameters influencing signal generation in flow-through membrane-based enzyme immunoassay," Analytical and Bioanalytical Chemistry, 387(3):1095-1104.
Koo, Charmaine K. et al., "An inkjet-printed electrowetting valve for paper-fluidic sensors", The Royal Society of Chemistry, 2013.
Kutyavin, IV et al. (Jan. 2000) "3 '-minor groove binder-DNA probes increase sequence specificity at PCR extension temperatures," Nucleic Acids Research, 28(2):655-661.
Kutyavin, IV et al. (Nov. 2002) "Reduced aggregation and improved specificity of G-rich oligodeoxyribonucleotides containing pyrazolo[3,4-d]pyrimidine guanine bases," Nucleic Acids Research, 30(22):4952-4959.
Labarre, P. et al. (May 2011) "A Simple, Inexpensive Device for Nucleic Acid Amplification without Electricity—Toward Instrument-Free Molecular Diagnostics in Low-Resource Settings," PLoS One, 6(5):e19738.
Lamar, JE et al. (Feb. 2003) "Sentinel cases of community-acquired methicillin-resistant *Staphylococcus aureus* onboard a naval ship," Military Medicine, 168(2):135-138.
Lei, KF and Butt, YKC (Jan. 2010) "Colorimetric immunoassay chip based on gold nanoparticles and gold enhancement," Microfluidics and Nanofluidics, 8:131-137.
Lei, KF and Wong, KS (epub Sep. 2010) "Automated Colorimetric Immunoassay Microsystem for Clinical Diagnostics," Instrumentation Science and Technology, 38(4):295-304.
Leirião, PR et al. (Jul. 2003) "Horseradish peroxidase immobilized through its carboxylic groups onto a polyacrylonitrile membrane—Comparison of enzyme performances with inorganic beaded supports," Applied Biochemistry and Biotechnology, 110(1):1-10.
Léonforte, F. et al. (May 2011) "Molecular transport and flow past hard and soft surfaces: computer simulation of model systems," Journal of Physics—Condensed Matter, 23(18):184105, 21 pp.
Li et al. "Paper-Based Microfluidic Devices by Plasma Treatment" Anal Chem (2008) 90, pp. 9131-9134.
Li et al. "Quantitative Biomarker Assay with Microfluidic Paper-based Analytical Devices" Anal Bioanal Chem, (2010) 396, pp. 495-501.
Li, JJ et al. (May 2008) "Optical scanner for immunoassays with up-converting phosphorescent labels," IEEE Transactions on Biomedical Engineering, 55(5):1560-1571.
Li, X. et al. (2012) "A perspective on paper-based microfluidics: Current status and future trends," Biomicrofluidics 6, 011301 (2012) 14 pages.

(56) References Cited

OTHER PUBLICATIONS

Li, X. et al. (Dec. 2008) "Paper-based microfluidic devices by plasma treatment," Analytical Chemistry, 80(23):9131-9134.
Li, X. et al. (Jan. 2010) "Quantitative biomarker assay with microfluidic paper-based analytical devices," Analytical and Bioanalytical Chemistry, 396(1):495-501.
Ligler, FS (Jan. 2009) "Perspective on Optical Biosensors and Integrated Sensor Systems," Analytical Chemistry, 81(2):519-526.
Lin, J-J et al. (2007; retrieved Mar. 2016) "Novel dry-type glucose sensor based on a metal-oxide-semiconductor capacitor structure with horseradish peroxidase plus glucose oxidase catalyzing layer," Japanese Journal of Applied Physics, 46(10A):6871-6874.
Lindman, Stina et al., "Salting the Charged Surface: pH and Salt Dependence of Protein G B1 Stability", Department of Biophysical Chemistry, Lund University, Lund, Sweden, 2006.
Linnes, J. C. et al. (Jan. 2014) "Paper-based molecular diagnostic for Chlamydia trachomatis," RSC Adv. 4(80):42245-42251.
Linnes, Jacqueline C. et al., "Paper-based molecular diagnostic for Chlamydia trachomatis", Biomedical Engineering, Boston University, Boston, MA, 2014.
Liu, KK et al. (epub Jul. 2010) "Microfluidic systems for biosensing," Sensor, 10(7):6623-6661.
Lokuge et al. "Temperature-controlled flow switching in nanocapillary array membranes mediated by poly(N-isopropylacrylamide) polymer brushes grafted by atom transfer radical polymerization" Langmuir, Jan. 2, 2007, 23(1): 305-11.
Lu, Y. et al. (Feb. 2009) "Low cost, portable detection of gold nanoparticle-labeled microfluidic immunoassay with camera cell phone," Electrophoresis, 30(4):579-582.
Lucas, Von Richard, "Uber das Zeitgesetz des kapillaren Aufstiegs von Flüssigkeiten," Apr. 10, 1918, 1 page.
Lutz et al. "Dissolvable Fluidic Time Delays for Programming Multi-step Assays in Instrument-Free Paper Diagnostics" Lab Chip (Jul. 21, 2013) 13(14) pp. 2840-2847.
Lutz, B. et al. (Jul. 2013) "Dissolvable fluidic time delays for programming multi-step assays in instrument-free paper diagnostics," Lab on a Chip, 13(14):2840-2847.
Lutz, B. R et al. (Oct. 2011) "Two-dimensional paper networks: programmable fluidic disconnects for multi-step processes in shaped paper," Lab Chip, 2011, 11, 4274-4278.
Lutz, B. R. et al. (May 2013) "Dissolvable fluidic time delays for programming multi-step assays in instrument-free paper diagnostics," Lab Chip, 2013, 13, 2840-2847.
Lutz, BR et al. (Dec. 2011) "Two-dimensional paper networks: programmable fluidic disconnects for multi-step processes in shaped paper," Lab on a Chip, 11(24):4274-4278.
Malhotra-Kumar, S. et al. (Dec. 2010) "Evaluation of molecular assays for rapid detection of methicillin-resistant *Staphylococcus aureus*," Journal of Clinical Microbiology, 48(12):4598-4601.
Malmberg, C. G. et al., "Dielectric Constant of Water from 0 to 100 C", Journal of Research of the National Bureau of Standards, 1956.
Mao, X. et al. (Feb. 2009) "Disposable Nucleic Acid Biosensors Based on Gold Nanoparticle Probes and Lateral Flow Strip," Analytical Chemistry, 81(4):1660-1668.
Marner, ES et al. (Apr. 2011) "Diagnostic accuracy of the", Cepheid GeneXpert vanA/vanB assay ver. 1.0 to detect the vanA and vanB vancomycin resistance genes in Enterococcus from perianal specimens, Diagnostic Microbiology and Infectious Disease, 69(4):382-389.
Martinez et al. "Patterned Paper as a Platform for Inexpensive, Low-volume, Portable Bioassays" Angewandte Chemie (2007) 46, pp. 1318-1320.
Martinez et al. "Programmable Diagnostic Devices Made From Paper and Tape" Lab Chip (2010) 10, pp. 2499-2504.
Martinez et al. "Three-dimensional Microfluidic Devices Fabricated in Layered Paper and Tape" PNAS, vol. 105, No. 50 (Dec. 16, 2008) pp. 19606-19611.
Martinez, A. W. et al. (2007) "Patterned Paper as a Platform for Inexpensive, Low-Volume, Portable Bioassays," Angew. Chem. Int. Ed. 2007, 46, 1318-1320.

Martinez, AW et al. (Dec. 2008) "FLASH: A rapid method for prototyping paper-based microfluidic devices," Lab on a Chip, 8(12):2146-2150.
Martinez, AW et al. (Dec. 2008) "Three-dimensional microfluidic devices fabricated in layered paper and tape," Proceedings of the National Academy of Sciences USA, 105(50):19606-19611.
Martinez, AW et al. (Feb. 2007) "Patterned paper as platform for inexpensive portable bioassays," Angewandte Chemie International Edition, 46(81):1318-1320.
Martinez, AW et al. (May 2008) "Simple Telemedicine for Developing Regions: Camera Phones and Paper-Based Microfluidic Devices for Real-Time Off-Site Diagnosis," Analytical Chemistry, 80(10):3699-3707.
Martinez, AW et al. (Oct. 2010) "Programmable diagnostic devices made from paper and tape," Lab on a Chip, 10(19):2499-2504.
Masson, M. et al. (Sep. 1993) "Chemical Activation of Nitrocellulose Membranes for Peptide Antigen-Antibody Binding-Studies—Direct Substitution of the Nitrate Group with Diaminoalkane," Electrophoresis, 14(9):860-865.
Mazzobre, MF et al. (May 1997) "Protective role of trehalose on thermal stability of lactase in relation to its glass and crystal forming properties and effect of delaying crystallization," LWT—Food Science and Technology, 30(3):324-329.
McCance, R. A. et al., "The secretion of urine during dehydration and rehydration", J. Physiol., 1944.
Mendez, S. et al. (Jan. 2010) "Imbibition in porous membranes of complex shape: quasi-stationary flow in thin rectangular segments," Langmuir, 26(2):1380-1385.
Mendez, S. et al. (Oct. 2009) "Imbibition in Porous Membranes of Complex Shape: Quasi-stationary Flow in Thin Rectangular Segments," Langmuir 2010, 26(2), 1380-1385.
Miller, DP et al. (Aug. 1998) "Stabilization of lactate dehydrogenase following freeze-thawing and vacuum-drying in the presence of trehalose and borate," Pharmaceutical Research, 15(8):1215-1221.
Moghadam B. Y. et al (May 2014) "Isotachophoretic Preconcenetration on Paper-Based Microfluidic Devices," Analytical Chemistry 2014, 86, 5829-5837.
Molinari, NA et al. (Jun. 2007) "The annual impact of seasonal influenza in the US: Measuring disease burden and costs," Vaccine, 25(27):5086-5096.
Monto, AS et al. (Nov. 2000) "Clinical Signs and Symptoms Predicting Influenza Infection," Archives of Internal Medicine, 160(21):3243-3247.
Morrison-Rodriguez, SM et al. (May 2010) "Community-associated methicillin-resistant *Staphylococcus aureus* infections at an Army training installation," Epidemiology and Infection, 138(5):721-729.
N. Dell et al. (Mar. 2012) "Digitizing paper forms with mobile imaging technologies," in Proceedings of the 2nd ACM Symposium on Computing for Development (ACM DEV '12), Article No. 2, 10 pages.
N. Panpradist et al. (Sep. 2014) "Swab sample transfer for point-of-care diagnostics: characterization of swab types and manual agitation methods," PLoS One, 9(9):e105786.
Natarajan, P. et al. (Dec. 2000) "Paper-based archiving of mammalian and plant samples for RNA analysis," Biotechniques, 29(6):1328-1333.
Ngom, B. et al. (2010) "Development and application of lateral flow test strip technology for detection of infectious agents and chemical contaminants: a review," Anal. Bioanal Chem (2010) 397:1113-1135.
Nie, Z. et al. (Nov. 2010) "Integration of paper-based microfluidic devices with commercial electrochemical readers," Lab on a Chip, 10(22):3163-3169.
Nielsen, K. (May 1995) "Stability of Freeze-Dried Horseradish-Peroxidase Conjugated Monoclonal-Antibodies Used in Diagnostic Serology," Journal of Immunoassay, 16(2):183-197.
Niemz, A. et al. (May 2011) "Point-of-care nucleic acid testing for infectious diseases," Trends in Biotechnology, 29(5):240-250.
Noguera, P. et al. (Jan. 2011) "Carbon nanoparticles in lateral flow methods to detect genes encoding virulence factors of Shiga toxin-producing *Escherichia coli*," Analytical and Bioanalytical Chemistry, 399(2):831-838.

(56) References Cited

OTHER PUBLICATIONS

Noh et al. "Metering the Capillary-Driven Flow of Fluids in Paper-Based Microfluidic Devices" Anal Chem (2010) 82, pp. 4181-4187.
Noh, H. and Philips, ST (May 2010) "Metering the capillary-driven flow of fluids in paper-based microfluidic devices," Analytical Chemistry, 82(10):4181-4187.
Noh, H. and Philips, ST (Oct. 2010) "Fluidic timers for time-dependent, point-of-care assays on paper," Analytical Chemistry, 82(19):8071-8078.
Noh, H. et al. (Oct. 2010) "Fluid Timers for Time-Dependent, Point-of-Care Assays on Paper," Analytical Chemistry 2010, 82, 8071-8078.
Noh, H. et al. (Oct. 2010) "Metering the Capillary-Driven Flow of Fluids in Paper-Based Microfluidic Devices," Analytical Chemistry 2010, 82, 4181-4187.
Non-Final Office Action in U.S. Appl. No. 13/518,365, dated Oct. 3, 2014, 15 pages.
Non-Final Office Action dated Feb. 16, 2017 in U.S. Appl. No. 14/601,966, 9 pages.
Non-Final Office Action dated Feb. 9, 2018 in U.S. Appl. No. 14/761,604 of Bishop, J. et al., filed Jul. 16, 2015.
Non-Final Office Action dated Jan. 25, 2016 in U.S. Appl. No. 14/601,966, 16 pages.
Non-Final Office Action dated May 16, 2016 in related U.S. Appl. No. 14/129,078, 46 pages.
Non-Final Office Action dated Nov. 14, 2017 in U.S. Appl. No. 13/518,365, 26 pages.
Non-Final Office Action dated Nov. 14, 2017 in U.S. Appl. No. 13/518,365, of Yager, P. et al., filed Jun. 21, 2012.
Non-Final Office Action dated Oct. 12, 2016 in U.S. Appl. No. 14/043,664, 21 pages.
Non-Final Office Action dated Oct. 19, 2018 in U.S. Appl. No. 15/135,461 for Yager et al., filed Apr. 21, 2016, 14 pages.
Notice of Allowance dated Oct. 17, 2016 in U.S. Appl. No. 14/129,078, 7 pages.
Nuovo, GV et al., "In situ strand displacement amplification: an improved technique for the detection of low copy nucleic acids", Diagnostic Molecular Pathology, Dec. 2000, 9(4):195-202.
O'Farrell, "Evolution in Lateral Flow-Based Immunoassay Systems" Humana Press (2009) pp. 1-33.
O'Farrell, B. (2009; retrieved Mar. 2016) "Evolution in Lateral Flow-Based Immunoassay Systems," in Lateral Flow Immunoassay, eds. R. Wong and H. Tse, Humana Press: New York, pp. 1-33.
Office Action dated May 5, 2016 in corresponding Chinese Patent Application No. 201480017562.5, 10 pages.
Ohtake, S. and Wang, YJ (Jun. 2011) "Trehalose: Current Use and Future Applications," Journal of Pharmaceutical Sciences, 100(6):2020-2053.
Osborn et al. "Microfluidics Without Pumps: Reinventing a T-Sensor and H-Filter in Paper Networks" Lab Chip, (2010) 10, pp. 2659-2665.
Osborn, J. et al. (Oct. 2010) "Microfluidics without pumps: reinventing the T-sensor and H-filter in paper networks," Lab on a Chip, 10(20):2659-2665.
Osborn, J. L. et al. (Jun. 2010) "Microfluidics without pumps: reinventing the T-sensor and H-filter in paper networks," The Royal Society of Chemistry, Lab Chip, 7 pages.
Ou, Zhaoyang et al., "Entropy and enthalpy of polyelectrolyte complexation: Langevin dynamics simulations", The Journal of Chemical Physics, 2006.
P. LaBarre et al. (May 2011) "A simple, inexpensive device for nucleic acid amplification without electricity-toward instrument-free molecular diagnostics in low-resource settings," PLoS One, 6(5):e19738.
Papp, John R. et al., "Recommendations for the Laboratory-Based Detection of Chlamydia trachomatis and Neisseria gonorrhoeae", MMWR, Mar. 14, 2014.
Park, Edward S. et al. (2010; retrieved Mar. 2016) "Packaging for Bio-micro-electro-mechanical Systems (BioMEMS) and Microfluidic Chips," in Nano-Bio-Electronic, Photonic and MEMS Packaging, C.P. Wong, Kyoung-Sik Moon, Yi Li (Eds.), Springer; pp. 505-563.
Patterson, K. et al. (Oct. 2002) "Development of a rapid immunodiagnostic test for Haemophilus ducreyi," Journal of Clinical Microbiology, 40(10):3694-3702.
PE Vandeventer et al. (2011) "Mechanical disruption of lysis-resistant bacterial cells by use of a miniature, low-power, disposable device," Journal of Clinical Microbiology, 49(7):2533-2539, doi: 10.1128/JCM.02171-10.
PE Vandeventer et al. (Jul. 2011) "Mechanical disruption of lysis-resistant bacterial cells by use of a miniature, low-power, disposable device," Journal of Clinical Microbiology, 49(7):2533-2539.
Peeling, R. et al. (Dec. 2006) "Rapid tests for sexually transmitted infections (STIs): the way forward," Sexually Transmitted Infections, 82(Suppl 5):v1-v6.
Peltola V. et al. (Oct. 2005) "Accuracy of clinical diagnosis of influenza in outpatient children," Clinical Infectious Diseases, 41(8):1198-2000.
Peterson, LR and Diekema, DJ (Mar. 2010) "To Screen or Not to Screen for Methicillin-Resistant *Staphylococcus aureus*," Journal of Clinical Microbiology, 48(3):683-689.
Point-of-care diagnostic market worth $27.5 Billion by 2018, Markets and Markets. (http://www.prnewswire.com/news-releases/point-of-care-diagnostic-market-worth-275-billion-by-2018-274885521.html), 2013.
Posthuma-Trumpie et al. "Lateral Flow (Immuno)assay: Its Strengths, Weaknesses, Opportunities and Threats. A Literature Survey" Anal Bioanal Chem, 393 (2009) pp. 569-582.
Posthuma-Trumpie, GA et al. (Jan. 2009) "Lateral flow (immuno)assay: its strengths, weaknesses, opportunities and threats. A literature survey," Analytical and Bioanalytical Chemistry, 393(2):569-582.
Pribyl, M. et al. (Apr.-Sep. 2006) "Modeling reaction-transport processes in a microcapillary biosensor for detection of human IgG," Microelectronic Engineering, 83(4-9):1660-1663.
Putnam, David F. et al., "Composition and Concentrative Properties of Human Urine", National Aeronautics and Space Administration, 1971.
Qian, S.Z. and Bau, HH (Mar. 2004) "Analysis of lateral flow biodetectors: competitive format," Analytical Biochemistry, 326(2):211-224.
Qu, Yatian et al., "Simultaneous Purification and Fractionation of Nucleic Acids and Proteins from Complex Samples Using Bidirectional Isotachophoresis", Analytical Chemistry, 2014.
R Core Team, "R: A Language and Environment for Statistical Computing," Version 3.2.5 (Apr. 14, 2016) 3,475 pages.
R. Mariella, Jr. (Dec. 2008) "Sample preparation: the weak link in microfluidics-based biodetection," Biomedical Microdevices, 10(6):777-784.
Rand, KH et al. (Jul. 2011) "A Comparison of Two Multiplex Methods for the Detection of Respiratory Viruses: FilmArray RP and xTAG RVP," Journal of Clinical Microbiology, 49(7):2449-2453.
Rao et al. "Developing rapid, point-of-care, multiplex detection for use in lateral flow devices" Proceedings of SPIE—The International Society for Optical Engineering 6007, Oct. 2005.
Rejeb, S. et al. (Dec. 1998) "Functionalization of nitrocellulose membranes using ammonia plasma for the covalent attachment of antibodies for use in membrane-based immunoassays," Analytical Chimica Acta, 376(1):133-138.
Restriction Requirement for U.S. Appl. No. 13/518,365, dated Mar. 19, 2014, 6 pages.
Richardson, A. et al. (Mar. 2008) "A nitric oxide-inducible lactate dehydrogenase enables *Staphylococcus aureus* to resist innate immunity," Science, 319(5870):1672-1676.
Robinson, JM and Karnovsky, MJ (Jun. 1991) "Rapid-Freezing Cytochemistry-Preservation of Tubular Lysosomes and Enzyme-Activity," Journal of Histochemistry and Cytochemistry, 39(6):787-792.
Roche, Business Overview, (http://www.roche.com/investors/reporting/fyr13_business_overview.htm), 2013.
Rogacs, A. et al. (Dec. 2013) "Purification of nucleic acids using isotachophoresis," Journal of Chromatography A, 1335 (2014) 105-120.

(56) References Cited

OTHER PUBLICATIONS

Rohrman, Brittany A. et al., "A paper and plastic device for performing recombinase polymerase amplification of HIV DNA", Lab Chip, 2012.
Rojas, E. and Liu, L. (May 2005) "Estimating the annual hospital", excess cost of methicillin-resistant *Staphylococcus aureus* infection in the United States, in International Society for Pharmaeconomics and Outcomes Research (ISPOR) Tenth Annual International Meeting, Washington, DC, 1 page.
Rosenvinge, M. M. et al., "Screening for asymptomatic chlamydia in women—how often would gonorrhoea be missed?", St. George's Hospital NHS Trust, London, UK, 2009.
Rossney, AS et al. (Oct. 2008) "Evaluation of the Xpert", Methicillin-Resistant *Staphylococcus aureus* (MRSA) Assay Using the GeneXpert Real-Time PCR Platform for Rapid Detection of MRSA from Screening Specimens, Journal of Clinical Microbiology, 46(10):3285-3290.
Rubinstein, E. et al. (Jun. 2008) "Pneumonia caused by methicillin-resistant *Staphylococcus aureus*," Clinical Infectious Diseases, 46(Suppl 5): S378-S385.
Safdar, N. and Bradley, EA (Apr. 2008) "The risk of infection after nasal colonization with *Staphylococcus aureus*," American Journal of Medicine, 121(4):310-315.
Schrader, C. et al. (Jun. 2012) "PCR inhibitors—occurrence, properties and removal," Journal of Applied Microbiology 113, 1014-1026.
Second Office Action in Chinese Patent Application No. 201480017562.5, dated Mar. 3, 2017, 3 pages.
Segall, G. and Purves, C. (1952; retrieved Mar. 2016) "The Action of Hydroxylamine, its o-methyl ether, and their Hydrochlorides on cellulose trinitrate in Pyridine," Canadian Journal of Chemistry, 30(11):860-871.
Sia, SK et al. (Jan. 2004) "An integrated approach to a portable and low-cost immunoassay for resource-poor settings," Angewandte Chemie (International Edition), 43(4):498-502.
Sigmundsson, K. et al. (Jul. 2002) "Determination of active concentrations", and association and dissociation rate constants of interacting biomolecules: An analytical solution to the theory for kinetic and mass transport limitations in biosensor technology and its experimental verification, Biochemistry, 41(26):8263-8276.
Siwoski, A. et al. (Aug. 2002) "An efficient method for assessment of DNA quality of archival microdissected specimens," Modern Pathology, 15(8):889-892.
Skidmore, S. (Oct. 2010) "Poorly performing point-of-care tests for chlamydia: what can be done?" Sexually Transmitted Infections, 86(5):330-330.
Squires, TM and Quake, SR (Oct. 2005) "Microfluidics: Fluid physics at the nanoliter scale," Reviews of Modern Physics, 77(3):977-1026.
SS Yun et al. (Mar. 2010) "Handheld mechanical cell lysis chip with ultra-sharp silicon nano-blade arrays for rapid intracellular protein extraction," Lab on a Chip, 10(11):1442-1446.
Stahlberg, A. et al. (Sep. 2004) "Comparison of reverse transcriptases in gene expression analysis," Clinical Chemistry, 50(9):1678-1680.
Stevens, D. (Aug. 2010) "Development and Optical Analysis of a Microfluidic Point-of-Care Diagnostic Device," Ph.D. thesis, University of Washington: Seattle, Washington, 230 pp.
Stevens, DY et al. (Dec. 2008) "Enabling a microfluidic immunoassay for the developing world by integration of on-card dry-reagent storage," Lab on a Chip, 8(12):2038-2045.
Strand, Sabina P. et al., "Influence of Chitosan Structure on the Formation and Stability of DNA-Chitosan Polyelectrolyte Complexes", Biomacromolecules, 2005.
Sudhakar, D. et al. (May 1979) "Grafting of methyl methacrylate to nitrocellulose by ceric ions," Journal of Applied Polymer Science, 23(10):2923-2928.
Suk, JW and Cho, J-H. (Apr. 2007) "Capillary flow control using hydrophobic patterns," Journal of Micromechanics and Microengineering, 17(4):N11-N15.

Sun et al. "Reversible switching between superhydrophilicity and superhydrophobicity" Angew Chem Int Ed Engl. Jan. 3, 2004, 43(3):357-60.
Tanriverdi, S. et al. (Apr. 2010) "A rapid and automated sample-to-result HIV load test for near-patient application," Journal of Infectious Diseases, 201(Supplement 1):s52-s58.
The Engineering ToolBox, Relavite Permittivity—Dielectric Constant. (http://www.engineeringtoolbox.com/relative-permittivity-d_1660.html), Accessed 2016.
The Lewin Group, Inc. prepared for Advanced Medical Technology Association (AdvaMed) (2005; accessed Feb. 2013) "The value of diagnostics innovation, adoption and diffusion into health care," available online at: http://www.lewin.com/publications/Publicati.
Thompson, WW et al. (Jan. 2003) "Mortality associated with influenza and respiratory syncytial virus in the United States," JAMA—Journal of the American Medical Association, 289(2):179-186.
Thompson, WW et al. (Sep. 2004) "Influenza-associated hospitalizations in the United States," JAMA—Journal of the American Medical Association, 292(11):1333-1340.
Toley, B. J. et al. (Jan. 2015) "A versatile valving toolkit for automating fluidic operations in paper microfluidic devices," The Royal Society of Chemistry, Lab Chip, 2015, 13 pages.
Unger, MA et al. (Apr. 2000) "Monolithic microfabricated valves and pumps by multilayer soft lithography," Science, 288(5463):113-116.
Unitaid Secretariat, World Health Organization (Jul. 2012) "Tuberculosis: Diagnostic Technology Landscape", 44 pages.
Uyeki, TM et al. (May 2009) "Low Sensitivity of Rapid Diagnostic Test for Influenza," Clinical Infectious Diseases, 48(9):E89-E92.
V. Gubala et al. (Jan. 2012) "Point of care diagnostics: status and future," Analytical Chemistry, 84(2):487-515.
Vasoo, S. et al. (Oct. 2009) "Rapid Antigen Tests for Diagnosis of Pandemic (Swine) Influenza A/H1N1," Clinical Infectious Diseases, 49(7):1090-1093.
Vijayendran, RA et al. (Dec. 1999) "A computational reaction-diffusion model for the analysis of transport-limited kinetics," Analytical Chemistry, 71(23):5405-5412.
Wakeley, PR et al. (Feb. 2010) "Use of a field-enabled nucleic acid extraction and PCR instrument to detect BVDV," Veterinary Record, 166(8):238-239.
Walker, GT et al. (Jan. 1996) "DNA detection by strand displacement amplification and fluorescence polarization with signal enhancement using a DNA binding protein," Nucleic Acids Research, 24(2):348-353.
Walkey, AJ et al. (May 2011) "Linezolid vs Glycopeptide Antibiotics for the Treatment of Suspected Methicillin-Resistant *Staphylococcus aureus* Nosocomial Pneumonia: A Meta-analysis of Randomized Controlled Trials," Chest, 139(5):1148-1155.
Wang et al. "Tree-shaped Paper Strip for Semiquantitative Colorimetric Detection of Protein with Self-calibration" Journal of Chromatography A, (2010) 1217, pp. 3896-3899.
Wang, G. et al. (Apr. 2003) "Amperometric hydrogen peroxide biosensor with sol-gel/chitosan network-like film as immobilization matrix," Biosensors and Bioelectronics, 18(4):335-343.
Wang, W. et al. (Jun. 2010) "Tree-shaped paper strip for semiquantitative colorimetric detection of protein with self-calibration," Journal of Chromatography A, 1217(24):3896-3899.
Washburn, Edward W., "The Dynamics of Capillary Flow," The Physical Review, Second Series, Mar. 1921, vol. XVII, No. 3, pp. 273-283.
Washburn, EW (Mar. 1921) "The Dynamics of Capillary Flow," Physical Review, 17(3):273-283.
Watchirs Smith, Lucy A. et al., "Point-of-care tests for the diagnosis of Neisseria gonorrhoeae infction: a systematic review of operational and performance characteristics", Sex Transm Infect, 2013.
Weigl, B. et al. (Dec. 2008) "Towards-Non- and minimally instrumented, microfluidics-based diagnostic devices," Lab Chip, 8(12):1999-2014.
Wellinghausen, N. et al. (Aug. 2009) "Rapid detection of *Staphylococcus aureus* bacteremia and methicillin resistance by real-time PCR in whole blood samples," European Journal of Clinical Microbiology and Infectious Diseases, 28(8):1001-1005.

(56) References Cited

OTHER PUBLICATIONS

Williams, MS et al. (Jul. 2008) "A practical guide to the staggered herringbone mixer," Lab on a Chip, 8(7):1121-1129.
Williams, R. (Jan. 1981) "The capillary without walls," Journal of Colloid Interface Science, 79(1):287-288.
Williams, Richard, "The Capillary Without Walls" Journal of Colloid and Interface Science, (Jan. 1981) vol. 79, No. 1, pp. 287-288.
Witkop, CT et al. (Feb. 2010) "Novel Influenza A (H1N1) Outbreak at the US Air Force Academy Epidemiology and Viral Shedding Duration," American Journal of Preventive Medicine, 38(2):121-126.
Wolk, DM et al. (Mar. 2009) "Multicenter Evaluation of the Cepheid Xpert Methicillin-Resistant *Staphylococcus aureus* (MRSA) Test as a Rapid Screening Method for Detection of MRSA in Nares," Journal of Clinical Microbiology, 47(3):758-764.
Wolk, DM et al. (Mar. 2009) "Rapid Detection of *Staphylococcus aureus*", and Methicillin-Resistant *S. aureus* (MRSA) in Wound Specimens and Blood Cultures: Multicenter Preclinical Evaluation of the Cepheid Xpert MRSA/SA Skin and Soft Tissue and Blood Culture Assays, Journal of Clinical Microbiology, 47(3):823-826.
World Health Organization (2013; retrieved Nov. 2015) "Global Tuberculosis Report," 306 pages.
Worwa, G. et al., "Allele-specific qRT-PCR demonstrates superior detection of single nucleotide polymorphisms as genetic markers for West Nile virus compared to Luminex® and quantitative sequencing", Journal of Virological Methods, Jan. 2014, 195:76-85.
Yager, P. et al. (Aug. 2008)"Point-of-care diagnostics for global health," Annual Review of Biomedical Engineering, 10:107-144.
Yager, P. et al. (Jul. 2006) "Microfluidic diagnostic technologies for global public health," Nature, 442(7101):412-418.
Yan, J. et al. (Feb. 2009) "A gold nanoparticle-based microfluidic protein chip for tumor markers," Journal of Nanoscience and Nanotechnology, 9(2):1194-1197.
Yeh, CH et al. (Jan. 2009) "An immunoassay using antibody-gold nanoparticle conjugate, silver enhancement and flatbed scanner," Microfluidics and Nanofluidics, 6(1):85-91.
Yetisen, Ali Kemal et al., "Paper-based microfluidic point-of-care diagnostic devices", Lab Chip, 2013.
Yu, J. et al., "Multi-platform assessment of transcriptional profiling technologies utilizing a precise probe mapping methodology", BMC Genomics, Sep. 2015, 16:710.
Zarakolu, P. et al. (Aug. 2002) "Preliminary evaluation of an immunochromatographic strip test for specific Treponema pallidum antibodies," Journal of Clinical Microbiology, 40(8):3064-3065.
Zentilin, L. et al., "The renaissance of competitive PCR as an accurate tool for precise nucleic acid quantification", Methods in Molecular Biology, 2010, 630:233-248.
Zhang, C. et al. (Apr. 2006) "Development of multianalyte flow-through", and lateral-flow assays using gold particles and horseradish peroxidase as tracers for the rapid determination of carbaryl and endosulfan in agricultural products, Journal of Agricultural and Food Chemistry, 54(7):2502-2507.
Zhao, W. and Van Den Berg, A. (Dec. 2008) "Lab on paper," Lab on a Chip, 8(12):1988-1991.
Zhao, WA et al. (Nov. 2008) "Paper-Based Bioassays Using Gold Nanoparticle Colorimetric Probes," Analytical Chemistry, 80(22):8431-8437.
Zhu, HY et al. (Jan. 2011) "Cost-effective and compact wide-field fluorescent imaging on a cell-phone," Lab on a Chip, 11(2):315-322.
Ziebarth, Jesse et al., "Molecular Dynamics Simulations of DNA-Polycation Complex Formation", Biophysical Journal, 2009.
Zimmermann, M. et al. (Feb. 2009) "Autonomous capillary system for one-step immunoassays," Biomedical Microdevices, 11(1):1-8.
Zimmermann, M. et al. (Jan. 2007) "Capillary pumps for autonomous capillary systems," Lab on a Chip, 7(1):119-125.
Zimmermann, M. et al. (Mar. 2005) "Continuous flow in open microfluidics using controlled evaporation," Lab on a Chip, 5(12):1355-1359.
Zimmermann, M. et al. (Sep. 2008) "Valves for autonomous capillary systems," Microfluidics and Nanofluidics, 5(3):395-402.
Zinderman, CE et al. (May 2004) "Community-acquired methicillin-resistant *Staphylococcus aureus* among military recruits," Emerging Infectious Diseases, 10(5):941-944.
Non-Final Office Action dated Apr. 20, 2020 in U.S. Appl. No. 15/135,461, 16 pages.

* cited by examiner

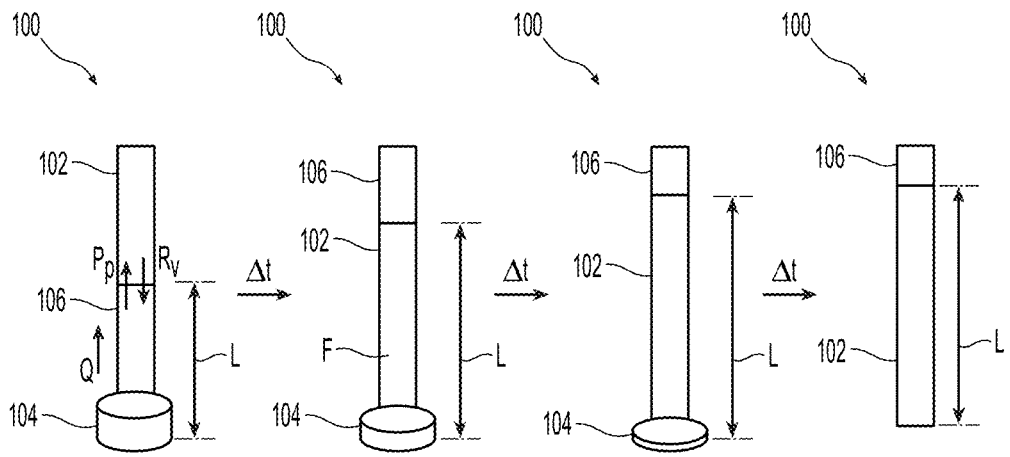
*Fig. 1A*  *Fig. 1B*  *Fig. 1C*  *Fig. 1D*
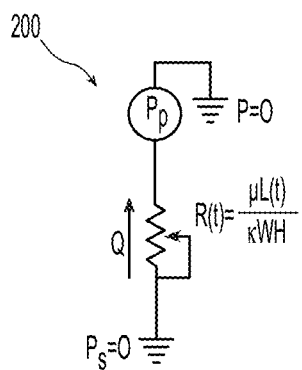
*Fig. 2*
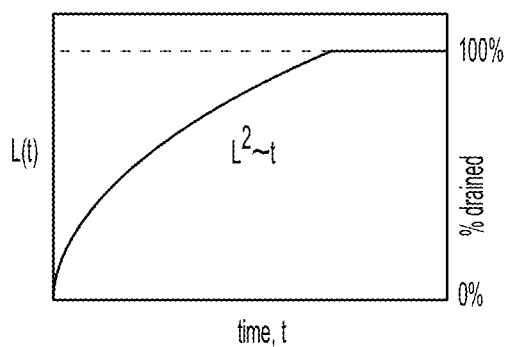
*Fig. 3*

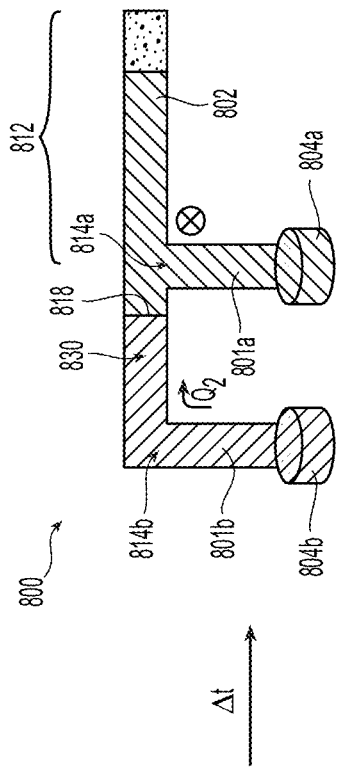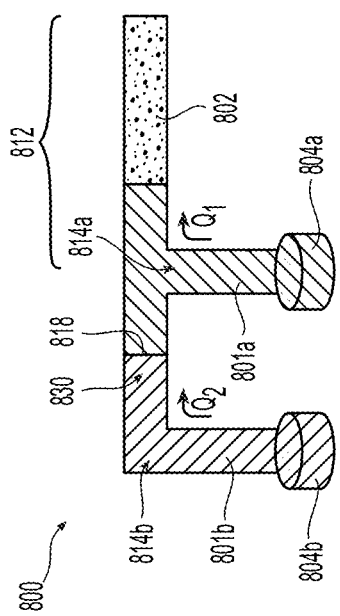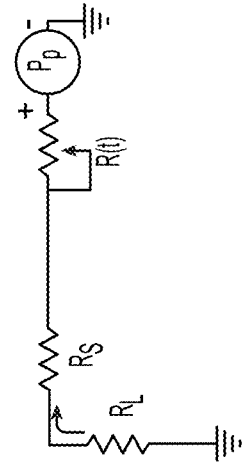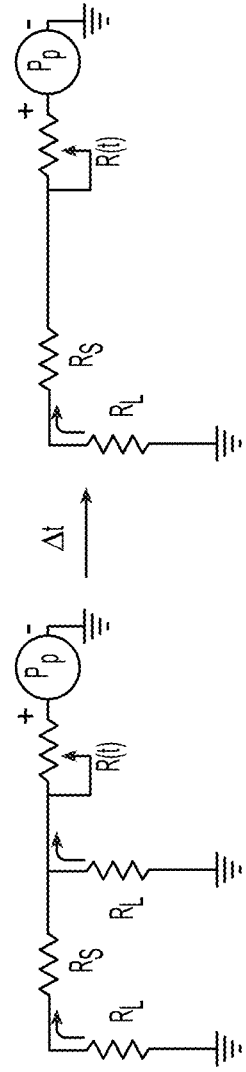
Fig. 8A
Fig. 8B
Fig. 9
Fig. 10

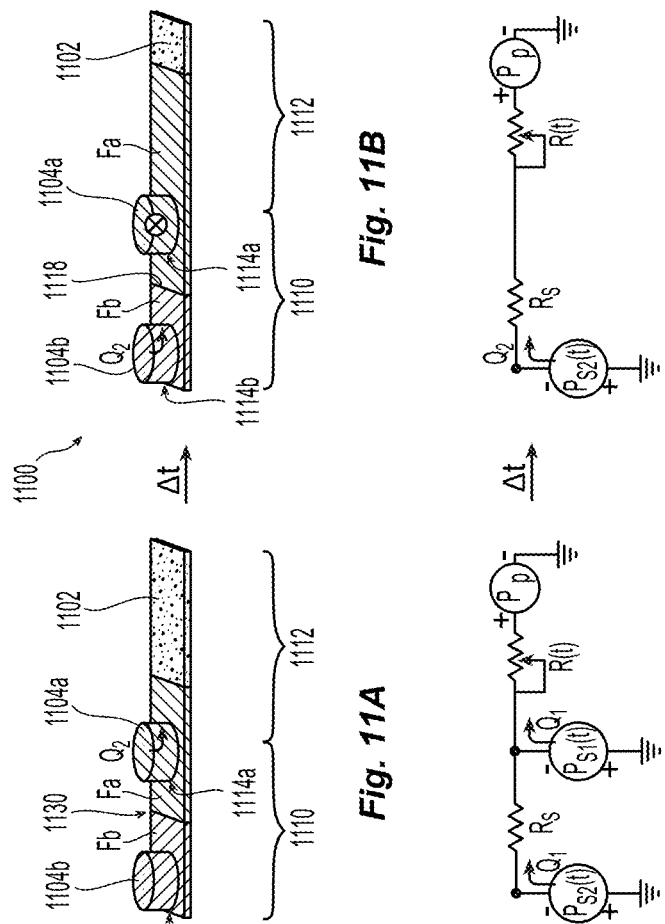
*Fig. 11A* *Fig. 11B*
*Fig. 12A* *Fig. 12B*
*Fig. 13A* *Fig. 13B*

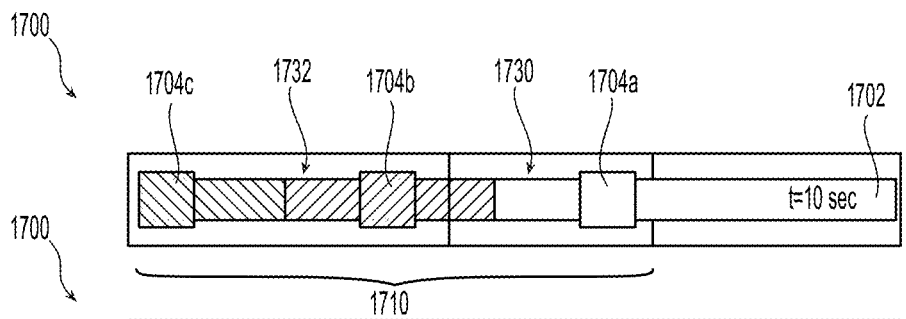
*Fig. 20A*
*Fig. 20B*
*Fig. 20C*
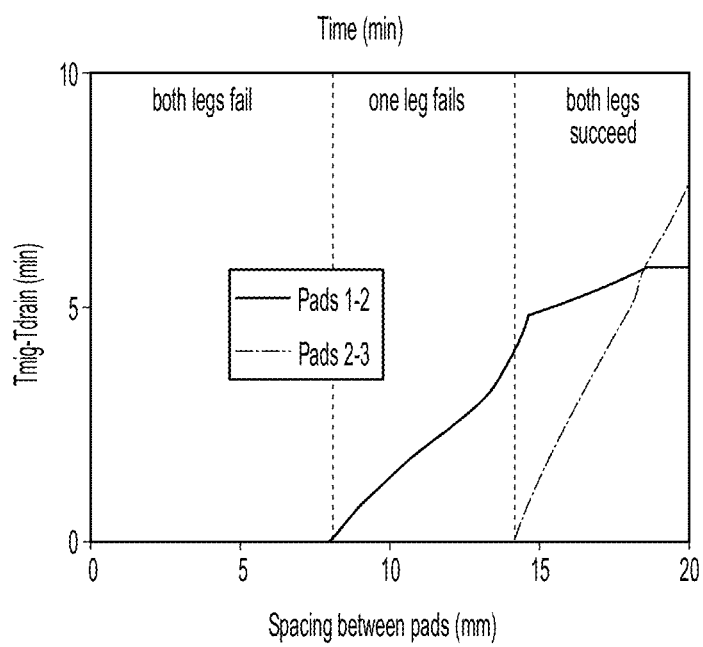
*Fig. 21*

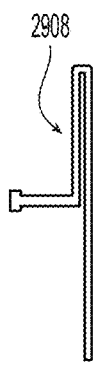 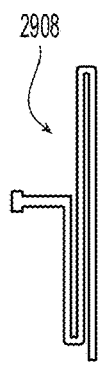 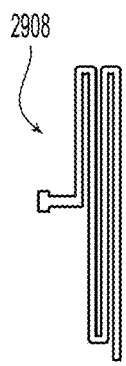 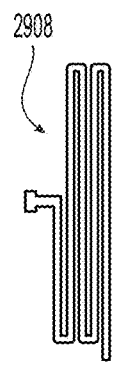 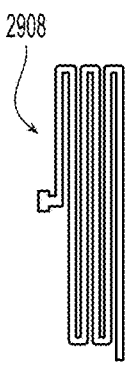
*Fig. 29A*  *Fig. 29B*  *Fig. 29C*  *Fig. 29D*  *Fig. 29E*
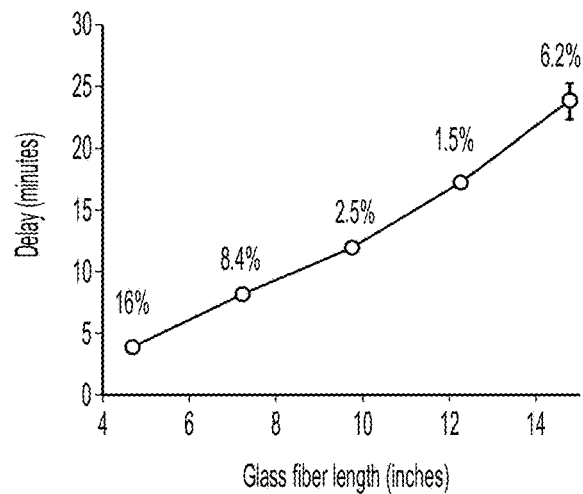
*Fig. 30*
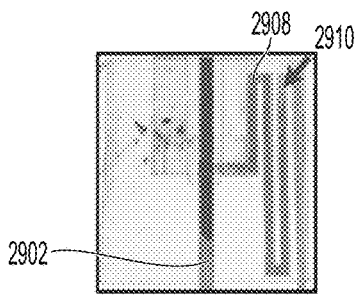 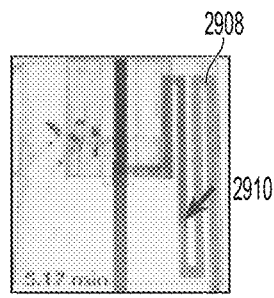 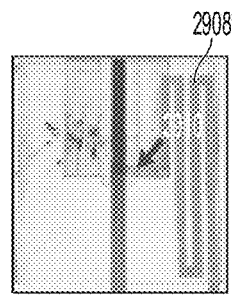
*Fig. 31A*  *Fig. 31B*  *Fig. 31C*
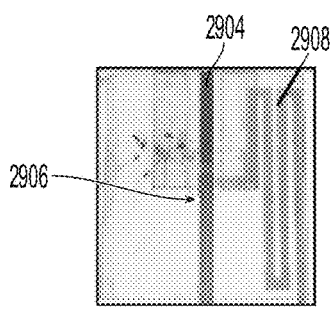 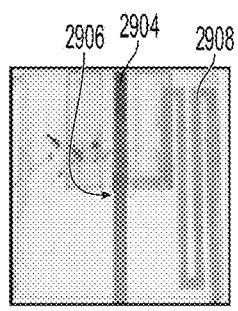 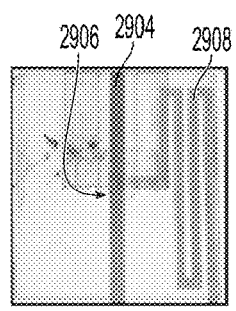
*Fig. 31D*  *Fig. 31E*  *Fig. 31F*

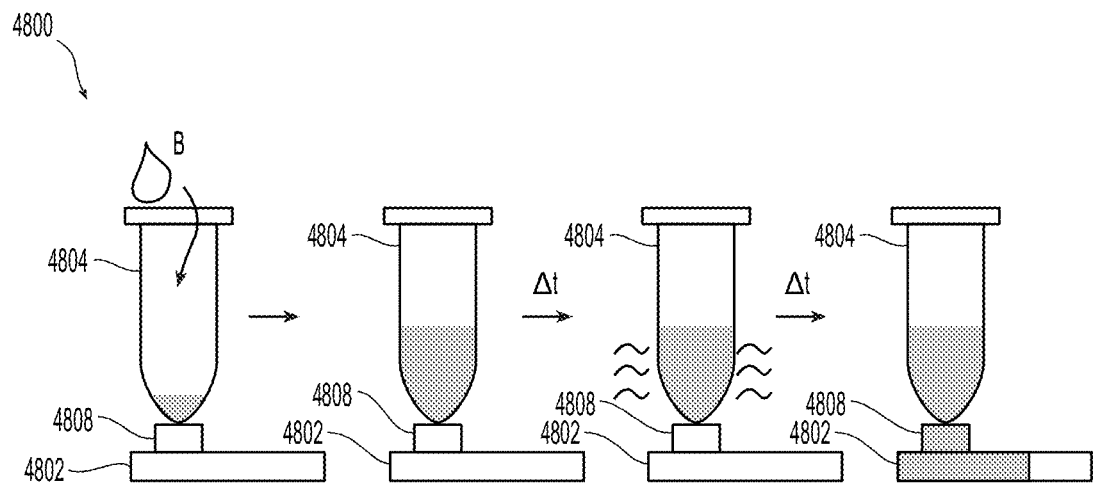
*Fig. 48A*   *Fig. 48B*   *Fig. 48C*   *Fig. 48D*
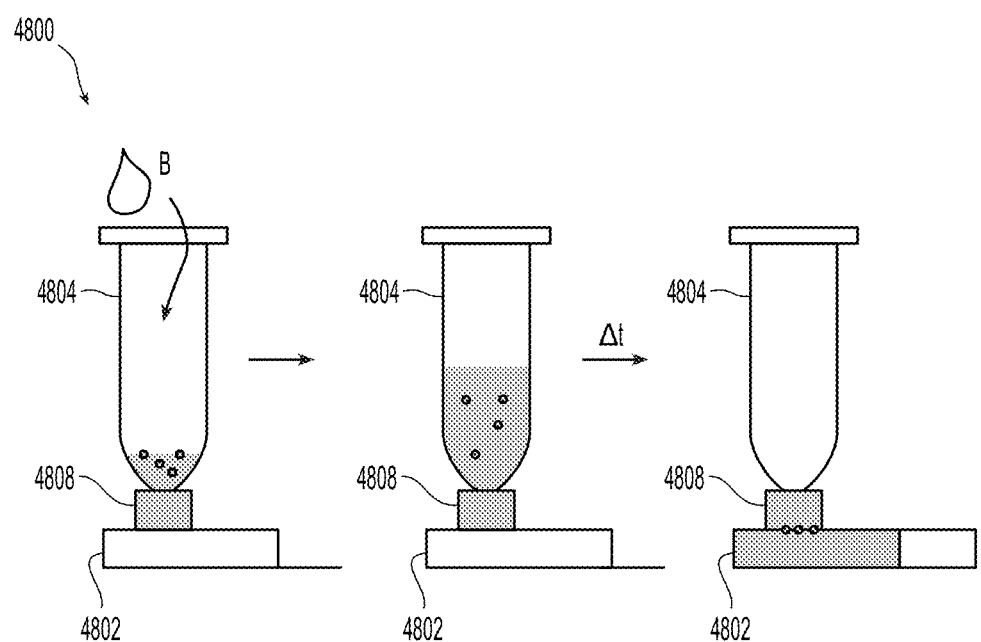
*Fig. 49A*   *Fig. 49B*   *Fig. 49C*

SEQUENTIAL DELIVERY OF FLUID VOLUMES AND ASSOCIATED DEVICES, SYSTEMS AND METHODS

CROSS-REFERENCE TO RELATED APPLICATIONS

This application is a continuation application of U.S. application Ser. No. 14/761,604, which is a 371 national stage entry of International Application No. PCT/US2014/012618, filed Jan. 22, 2014, which claims the benefit of the following applications:

(a) U.S. Provisional Application No. 61/755,134, filed Jan. 22, 2013;
(b) U.S. Provisional Application No. 61/808,106, filed Apr. 3, 2013;
(c) U.S. Provisional Application No. 61/832,356, filed Jun. 7, 2013;
(d) U.S. Provisional Application No. 61/861,055, filed Aug. 1, 2013;
(e) U.S. Provisional Application No. 61/867,941, filed Aug. 20, 2013;
(f) U.S. Provisional Application No. 61/867,950, filed Aug. 20, 2013; and
(g) U.S. Provisional Application No. 61/868,006, filed Aug. 20, 2013.

All of the foregoing applications are incorporated herein by reference in their entireties. Further, components and features of embodiments disclosed in the applications incorporated by reference may be combined with various components and features disclosed and claimed in the present application.

STATEMENT REGARDING FEDERALLY SPONSORED RESEARCH

This invention was made with government support under Grant No. HR0011-11-2-0007, awarded by the Defense Advanced Research Projects Agency. The government has certain rights in the invention.

TECHNICAL FIELD

The present technology is generally related to capillarity-based devices for performing chemical processes and associated systems and methods. In particular, several embodiments are directed toward sequential delivery of two or more fluids onto a porous wick.

BACKGROUND

Lateral flow strip tests ("LFT" or "LFTs") have been identified as a diagnostic technology well-suited for point-of-care ("POC") use in low resource settings. With fluid transport occurring due to the capillary pressure of the strip material (rather than through the use of pumps), LFTs are entirely disposable, rapid, user-friendly and affordable. Numerous LFTs have been developed and successfully used in limited-resource settings, with applications including pregnancy testing and disease diagnosis. The basic function of a LFT is to mix a substance of interest (e.g., an analyte) with a visible label (e.g., antibodies conjugated to gold nanoparticles) and capture the analyte-label complex at a detection line via an immobilized capture molecule (e.g., antibody). While the simplicity of LFTs makes them ideal for use as a POC tool, it has generally limited them to performing tests that can be carried out in a single chemical step. Moreover, the use of LFTs as a clinically relevant diagnostic tool can be limited to targets with high(er) concentrations because of limited analytical sensitivity of the LFT format.

Porous membranes are often used in conventional LFTs and flow-through cartridges. As such, flow of fluid through the LFT usually occurs by wicking through a membrane (either laterally or transversely) onto an absorbent pad. Immunoassays take advantage of such porous membrane systems to measure and analyze analyte samples. The dependence on wicking to generate flow greatly limits control over assay conditions. Specifically, lateral flow assays are often limited to a single step in which the sample (and buffer) is added to the sample pad, and the sample flows by capillary action (i.e., wicking) along the pad. Capillarity provides the force needed to provide a nearly continuous flow of fluid from one point to another, causing reagents stored in dry form to be transported along the device and to pass over regions that contain immobilized capture molecules. These devices are typically restricted to simple one-shot detection chemistries like colored nanoparticles that do not provide the sensitivity possible with multistep-detection chemistries, such as enzymatic amplification. They are also rarely quantitative.

Microfluidic systems that include open fluid channels for the flow of buffers, samples, and reagents can inherently be made much more sophisticated, and it is possible to use them to carry out a very large number of fluid-processing steps. Such microfluidic systems usually incorporate a complex disposable, which leads to unavoidably high per-test manufacturing costs and the need for expensive external pumps and valves to move fluids. While microfluidic devices can inherently be very flexible in the functions that they perform, they are also inherently complicated and expensive. Additionally, the devices that have been made that support complex function are usually quite complex themselves. For example, some polymeric laminate cartridges currently developed contain as many as 23 different layers, each of which must be separately manufactured and bonded to the others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIGS. 1A-1D are a series of time-lapsed front views of a capillary-based fluidic system.

FIG. 2 is an electrical circuit model corresponding to the fluidic system shown in FIGS. 1A-1D.

FIG. 3 is a graph showing migration of the fluid front shown in FIGS. 1A-1D as a function of time for a finite fluid source.

FIGS. 8A-8B are a series of time-lapsed views of a two-dimensional paper network configured in accordance with the present technology.

FIG. 9 is an electrical circuit model corresponding to the fluidic systems shown in FIG. 8A.

FIG. 10 is an electrical circuit model corresponding to the fluidic systems shown in FIG. 8B.

FIGS. 11A-11B are a series of time-lapsed views of a pseudo one-dimensional paper network configured in accordance with the present technology.

FIGS. 12A-12B are electrical circuit models corresponding to the fluidic system shown in FIGS. 12A-12B, assuming non-ideal fluid sources.

FIGS. 13A-13B are electrical circuit models corresponding to the fluidic system shown in FIGS. 12A-12B, assuming ideal fluid sources.

FIGS. 20A-20C are a series of time-lapsed side views of a sequential delivery device having non-ideal fluid sources showing sequential fluid delivery without leakage.

FIG. 21 is a computational model showing the difference between the time for migration and the time for draining versus fluid outlet spacing.

FIGS. 29A-29E are several embodiments of fluid delivery channels having different lengths configured in accordance with the present technology.

FIG. 30 is a graph showing the activation delay versus glass fiber length.

FIGS. 31A-31F are time-lapsed top views of a control device configured in accordance with the present technology.

FIGS. 48A-48D are front views showing a molecular assay system configured in accordance with an embodiment of the present technology.

FIGS. 49A-49C are front views showing a molecular assay system configured in accordance with an embodiment of the present technology.

DETAILED DESCRIPTION

The present technology describes various embodiments of devices, systems and methods for processing, analyzing, detecting, measuring, and separating fluids. The devices can be used to perform these processes on a microfluidic scale, and with control over fluid and reagent transport. In one embodiment, for example, the porous receiving element having an input region and a receiving region, a first fluid source and a second fluid source positioned within the input region of the receiving element; wherein the first fluid source is positioned between the second fluid source and the receiving region, and wherein, when both the first and second fluid sources are in fluid connection with the input region, the device is configured to sequentially deliver the first fluid and the second fluid to the receiving region without leakage.

Figure 70:
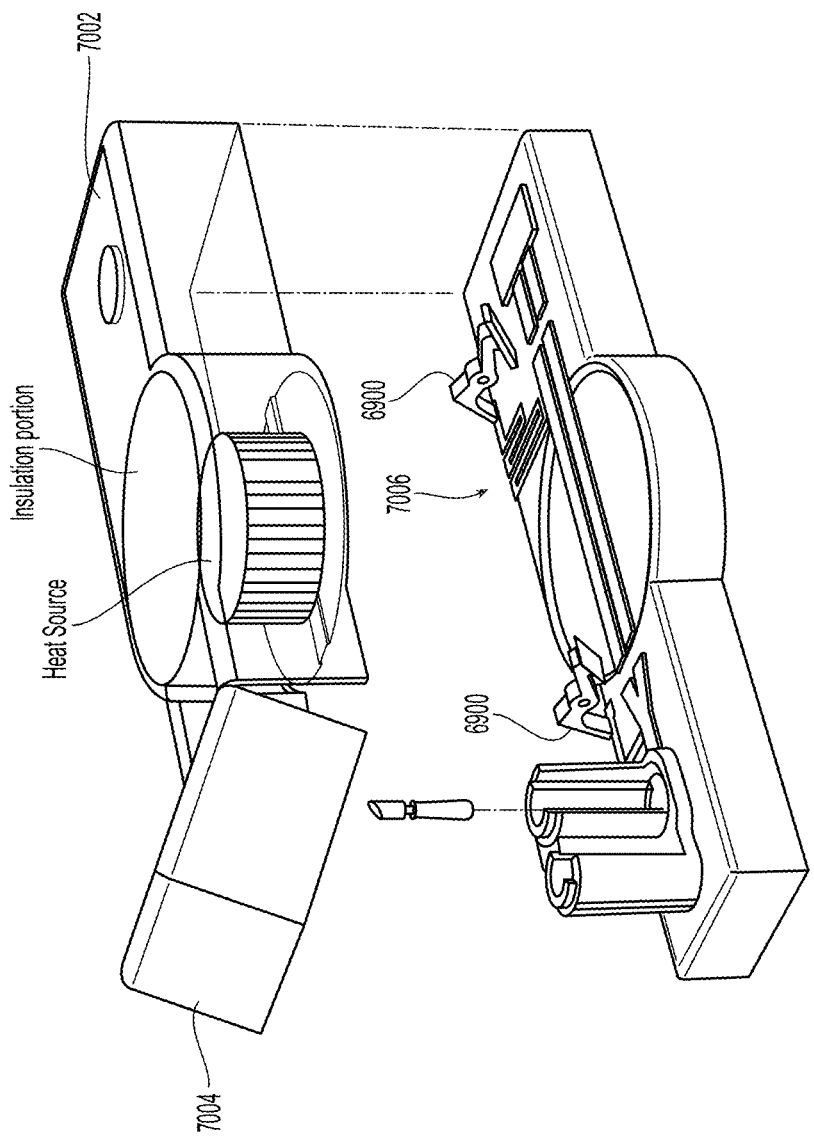
FIG. 70 is a perspective view of a detection device configured in accordance with yet another embodiment of the present technology.

Specific details of several embodiments of the technology are described below with reference to FIGS. 1A-70. Other details describing well-known structures and systems often associated with capillarity-based devices, biomedical diagnostics, immunoassays, etc. have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1A-70.

I. DEFINITIONS

As used herein, "porous element" or "porous membrane" refers to a porous membrane (e.g., a wick, pathway, leg, pad, delivery channel, etc.) through which fluid can travel by capillary action, such as paper, nitrocellulose, nylon, glass fiber, and the like. Unless the context clearly requires otherwise, a porous element can be two-dimensional or three-dimensional (when considering its height in addition to its length and width). Additionally, a porous membrane can be a single layer or may comprise two or more membranous layers. Although in some embodiments a specific term may be used (e.g., "wick," "pathway," "leg," "pad," "delivery channel," etc.), it should be understood that use of a different porous element is also within the scope of the present technology.

As used herein, "wettably distinct" means being capable of being wetted by contact with separate fluids without mixing of the fluids at the point of initial wetting. For example, two input legs are wettably distinct if they are physically separated so that each leg could be brought into contact with a separate fluid reservoir. Pathways can be made wettably distinct by a variety of means including, but not limited to, separation via distinct edges (e.g., cut as separate pathways) and separation via an impermeable barrier.

As used herein, "ideal fluid source" or "substantially ideal fluid source" refers to a fluid source that exerts negligible capillary backpressure during release into a porous matrix. One such example of an ideal fluid source is a well source. "Non-ideal fluid source" refers to a fluid source that exerts non-negligible capillary backpressure during release into a porous matrix.

As used herein, a two-dimensional paper network ("2DPN") refers to a system that includes at least two interconnected wettably distinct wicks, pathways, and/or legs. A one-dimensional paper network ("1DPN") refers to a system that only includes a single wick, pathway, or leg. A "pseudo-1DPN" refers to a single wick, pathway or leg directly coupled to one or more fluid sources (e.g., without a wettably distinct leg therebetween).

II. PHYSICAL PRINCIPLES a. Relationship Between Capillary-Driven Flow and Electrical Circuits FIG. 1A-1D are time lapsed front views showing a fluidic system 100 that includes a wick 102 fluidly connected at one end to an ideal fluid source 104. The ideal fluid source 104 contains a finite volume of a fluid F. As shown in FIGS. 1A-1D, fluid F flows from the ideal fluid source 104 to the wick 102 via capillary action. The rate Q at which the fluid F flows through the wick 102 is affected by two opposing forces: (1) the capillary pressure $P_P$ of the wick 102 that pulls the fluid F into the wick 102, and (2) the viscous resistance $R_V$ that opposes fluid flow through the pores of the wick 102. Viscous resistance $R_V$ depends on the wetted length L of the fluid column 106, and is determined by the equation $R_V = \mu L / \kappa W H$ (where $\mu$ is fluid dynamic viscosity, $\kappa$ is permeability, and W is the width of the wick 102 and H is the height of the wick 102). As more fluid F is taken up by the wick 102, the length L of the fluid column 106 increases such that the length L of the fluid column 106 is a function of time t. Since the viscous resistance $R_V$ depends on the wetted length L(t), viscous resistance $R_V$ thus also depends on time (i.e., $R_V = \mu L(t)/\kappa W H$).

The capillary-driven flow shown in FIGS. 1A-1D can also be described by analogy to simple electrical circuits. For example, as shown in the electrical circuit model 200 in FIG. 2, the pressure $P_P$ created by capillary force or gravity can be analogized to electrical voltage, the fluid flow rate Q can be analogized to electrical current, and viscous resistance $R_V$ can be analogized to electrical resistance. Atmospheric pressure (i.e., P=0) acts on all fluid-air interfaces and can be analogized to the electrical ground. The capillary backpressure $P_S$ exerted by the ideal fluid source 104 can also be represented as a ground since, for ideal fluid sources, the capillary backpressure is negligible and thus essentially zero. Furthermore, just as Ohm's Law (i.e., I=V/R) in electrical circuits relates the current I to the voltage V and resistance R, the one-dimensional form of Darcy's law (i.e., Q=P/R) similarly relates the fluid flow rate Q to the driving pressure P and viscous resistance R. The following equations can be derived from evaluating the circuit model 200:

$$Q(t) = \varepsilon W H \frac{dL(t)}{dt} = \frac{P_P}{R} = \frac{\kappa W H P_P}{\mu L(t)}; \quad \text{(Equation 1)}$$

-continued $$L^2 = \left(\frac{2\kappa P_P}{\mu\varepsilon}\right)t;$$ (Equation 2)

where ε is the void volume of the porous material.

The graph shown in FIG. 3 shows the change in wettable length over time for the fluidic system 100. The combination of a constant capillary pressure $P_P$ and the rising resistance $R_R$ during wet out causes the fluid front to slow over time (following $L^2 \sim t$) until the fluid source 104 is depleted. The scaling found in Equation 2 ($L^2 \sim t$) matches exactly the Lucas-Washburn expression describing one-dimensional driven wet-out. Accordingly, electrical analogies can be useful for understanding the basic concepts of capillary-driven flow in porous materials.

b. Non-Ideal Fluid Sources and Capillary Backpressure

The derivations based on FIGS. 1A-1D assume fluid sources comprised of ideal fluid source materials that exert negligible backpressure during the release of fluid from the source. As illustrated in FIGS. 4-7, though non-ideal fluid source materials can also be utilized, the choice of non-ideal source material can affect both the total amount of fluid released into the wick and the rate at which fluid travels through the wick.

Figure 4:
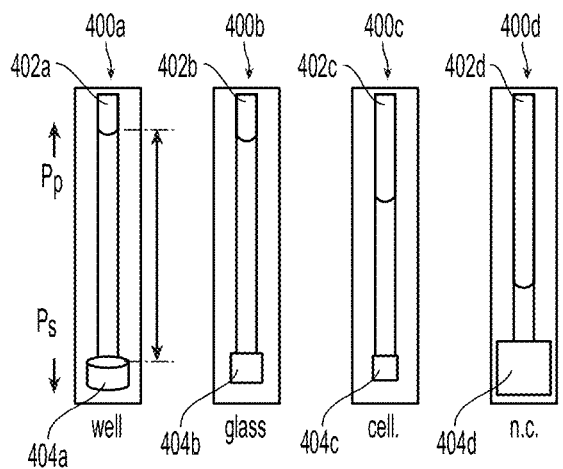
FIG. 4 is a top view of four fluidic devices, each including different source materials.
Figure 5:
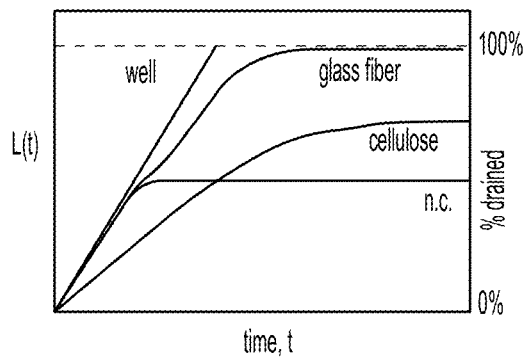
FIG. 5 is a graph showing the change in wettable length over time for each fluidic system shown in FIG. 4.

FIG. 4 is a top view of four fluidic systems 400a-d individually comprising different fluid sources 404a-d, each fluidly connected to a nitrocellulose wick 402a-d. FIG. 4 shows each fluidic system 400a-d once wicking had ceased in each system. Additionally, each fluid source 404a-d initially held the same volume of fluid. Fluidic system 400a includes a well 404a (ideal fluid source) not shown), fluidic system 400b includes a glass fiber fluid source 404b (non-ideal), fluidic system 400c includes a cellulose fluid source 404c (non-ideal), and fluidic system 400d includes a nitrocellulose fluid source 404d (non-ideal). As shown in FIG. 4, in the fluidic system 400a utilizing the well source 404a (ideal fluid source), the entire volume of fluid was released (as indicated by the wettable length L for fluidic system 400a). Out of the non-ideal fluid sources, the glass fiber source 404b also released the entire volume of fluid, yet both the cellulose fluid source 404c and nitrocellulose fluid source 404d retained a large percentage of the fluid. The graph in FIG. 5 shows that while the glass fiber fluid source 404b fully drained, the release rate was slower than that in the fluidic system utilizing the well source 404a (ideal fluid source). When the nitrocellulose fluid source 404c was used, well-like (ideal) delivery occurred until the nitrocellulose fluid source became about 50% depleted, at which point delivery quickly halted. Furthermore, although the cellulose fluid source 404c delivered a larger percentage of fluid than the nitrocellulose fluid source 404d, the cellulose fluid source 404c showed a much slower release. Accordingly, the non-ideal fluid sources 404b-d exhibited non-linear release profiles (as shown in FIG. 5) and indicate that capillary pressures can change as fluid is drained.

Figure 6:
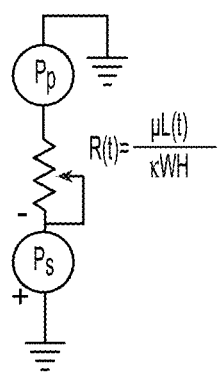
FIG. 6 is an electrical circuit model corresponding to the fluidic systems shown in FIG. 4.

FIG. 6 is an electrical circuit model 600 that describes the non-ideal fluid source behavior shown in FIGS. 4 and 5. As shown in FIG. 6, when a non-ideal fluid source is used as the fluid source, the fluid source is represented in the circuit model 600 by a voltage source rather than a ground. This is because, in contrast to ideal fluid sources, non-ideal fluid sources exhibit non-negligible capillary backpressure $P_S$ (e.g., a pressure that opposes the capillary pressure of the wick).

Using the circuit models for ideal and non-ideal sources (200, 600), the time-dependent capillary pressure of a given material can be derived based on experimentally obtainable values. For example, for a well or ideal fluid source:

$$Q^{ideal} = \varepsilon WH \frac{dL^{ideal}}{dt} = \frac{P_P}{R} = \frac{\kappa WHP_P}{\mu L^{ideal}}$$ (Equation 3)

For a non-ideal fluid source:

$$Q^{non-ideal} = \qquad \text{(Equation 4)}$$
$$\varepsilon WH \frac{dL^{non-ideal}}{dt} = \frac{P_P - P_S(t)}{R} = \frac{\kappa WH[P_P - P_S(t)]}{\mu L^{non-ideal}}$$

Taking the ratio of these two equations gives the time dependent capillary pressure of a non-ideal fluid source ($P_S(t)$) based on the length L and rate dL(t)/dt that fluid has traveled through the wick for both the ideal and non-ideal case:

$$\frac{P_S(t)}{P_P} = 1 - \frac{L(t)^{pad}\frac{dL(t)^{pad}}{dt}}{L(t)^{well}\frac{dL(t)^{well}}{dt}}$$ (Equation 5)

Accordingly, the capillary pressures of the wick material and fluid source material affect both the distance and rate at which fluid travels through the wick (L(t) and dL(t)/dt, respectively).

Figure 7:
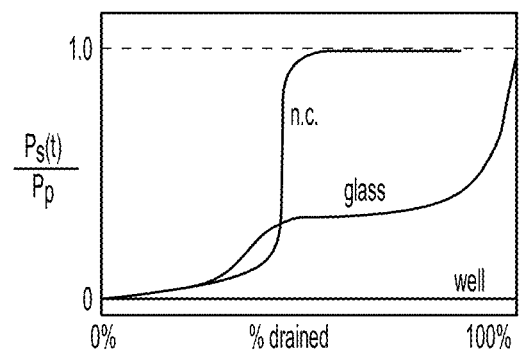
FIG. 7 is a graph showing the capillary pressure differential for the fluidic systems shown in FIG. 4.

FIG. 7 plots the capillary pressure profile during fluid release for the non-ideal fluid sources discussed with reference to FIG. 4. As shown in FIG. 7, the capillary pressure of a non-ideal source can deviate significantly from that of an ideal fluid source. In contrast to the constant negligible backpressure exerted by a well (ideal fluid source), non-ideal fluid sources such as glass fiber and nitrocellulose sources have complex capillary pressure functions that vary as they drain. For example, in the initial stages of delivery the glass fiber source 404b behaves as a well and has a very low capillary pressure. However, the capillary backpressure exerted on the fluid by the glass fiber source 404b drastically increases as more fluid is released from the glass fiber source 404b. Such behavior can be observed in the graph of FIG. 7, where the rate of fluid released from the glass fiber fluid source 404b increasingly deviates from the well source 404a over time. The graph also shows that fluid release from the nitrocellulose fluid source 404d initially occurs with little capillary backpressure until reaching a critical depletion level (~50%), at which point the pressure between wick and the nitrocellulose fluid source 404d equalizes. This pressure equilibration eliminates the driving force for flow and as a result, the nitrocellulose source 404d retains the remainder of its fluid (as seen in FIG. 4).

Changes in capillary backpressure shown during drainage of non-ideal fluid sources can be explained, to some extent, by the non-uniform pore distribution of many non-ideal fluid sources (e.g., glass fiber, cellulose, and nitrocellulose). For example, a material composed of small and large pores may exert a bimodal capillary backpressure $P_S$. The backpressure $P_S$ may first be low as the large pores drain but then increase when only the small pores remain filled.

III. SELECTED EMBODIMENTS OF SEQUENTIAL DELIVERY DEVICES a. 2DPNs with Ideal Fluid Sources

FIGS. 8A-8B are time lapsed side views of a sequential delivery device 800 ("the device 800") configured in accordance with the present technology. The device 800 can include a first leg 801a, a second leg 801b, and a receiving element 802. The receiving element 802 can be any porous material such as a wick, pathway, or leg, and the first and second legs 801a-b can have generally the same length. The first leg 801a can have an input end fluidly coupled to a first fluid source 804a and an outlet 814a fluidly coupled to the receiving element 802. The second leg 801b can have an input end fluidly coupled to a second fluid source 804b and a second outlet 814b coupled to the receiving element 802. The first and second fluid sources 804a-b can be ideal fluid sources (e.g., a well) and configured to hold a first and second fluid $F_a$, $F_b$, respectively. The first outlet 814a and the second outlet 814b can be spaced apart along the receiving element 802 on either side of a spacer portion 830 of the receiving element 802. The first outlet 814a can be positioned closer to a receiving region 812 of the receiving element 802 such that first outlet 814a is positioned between the second outlet 814b and the receiving region 812.

FIG. 8A shows the device 800 at an initial stage after the first and second legs 801a-b have been simultaneously fluidly coupled to their respective fluid sources. As shown in FIG. 8A, at least a portion of the first and second fluids $F_a$, $F_b$ will wick through their respective legs 801a, 801b and meet in the spacer region 830 generally at an interface 818 midway between the first and second outlets 814a, 814b. After this point, the first fluid source 804a continues to deliver the first fluid $F_a$ at a first rate $Q_1$ while the second fluid source 804b continues to deliver the second fluid $F_b$ at a second rate $Q_2$ that is slower than the first rate $Q_1$. As such, flow of the second fluid $F_b$ (i.e., the leakage flow) causes migration of the interface 818 toward the receiving region 812. Accordingly, to achieve sequential delivery of the first fluid $F_a$ and the second fluid $F_b$ (in that order), the first fluid $F_a$ must completely drain before the interface 818 breaches the first fluid outlet 814a.

FIGS. 9 and 10 show the electrical circuit models that correspond with FIGS. 8A and 8B, respectively. Solving these models (based on the electric circuit analogy principles described above) provides the following ratio of flow rates delivered by each leg 801a-b of the device 800:

$$\frac{Q_2}{Q_1} = \frac{1}{1 + \frac{R_S}{R_L}} \quad \text{(Equation 6)}$$

According to Equation 6, if the ratio is greater than 1, the second flow rate $Q_2$ is greater than the first flow rate $Q_1$ and the leakage flow (of the second fluid $F_b$) will breach the first outlet 814a before the first fluid source 804a has completely emptied. If the ratio is between 0 and 1, the first flow rate $Q_1$ is greater and the first fluid source 804a will completely empty before the interface 818 breaches the first outlet 814a. Additionally, other factors can reduce leakage flow in 2DPN models, such as the volumetric capacity of the spacer region 830, the spacer resistance $R_S$, and the leg resistance $R_L$. For example, the leakage flow can be reduced by increasing the spacer resistance $R_S$ (e.g., by increasing length or decreasing width), decreasing the leg resistance $R_L$ (e.g., by decreasing length or increasing width), and/or increasing the volumetric capacity of the spacer region 830.

b. Pseudo-1DPNs with Two Fluid Sources

FIGS. 11A-11B show time-lapsed views of a sequential delivery device 1100 ("the device 1100") configured in accordance with the present technology. As shown in FIGS. 11A-11B, the device 1100 can include a plurality of fluid sources (individually referred to as a first fluid source 1104a and a second fluid source 1104b) and a receiving element 1102. The receiving element 1102 can be any porous material such as a wick, pathway, or leg and can have an input region 1110 and a receiving region 1112. For example, the first fluid outlet 1114a can be positioned between the second fluid source outlet 1114b and the receiving region 1112. The fluid sources 1104a, 1104b can each have an outlet 1114a, 1114b positioned within the input region 1110 of the receiving element 1102. As such, the fluid sources 1104a, 1104b are configured to be fluidly connected to the receiving element 1102. The fluid source outlets 1114a, 1114b are separated along the receiving element 1102 by a spacer region 1130.

FIG. 11A shows the device 1100 at an initial stage after the first and second fluid sources 1104a-b have been simultaneously fluidly coupled to the input region of the receiving element 1102. As shown in FIG. 11A, regardless of the type of fluid source, at least a portion of the first and second fluids $F_a$, $F_b$ will wick into the input region 1110 and meet in the spacer region 1130 generally at an interface 1118 midway between the first and second outlets 1114a, 1114b. Although a small amount of diffusive mixing may occur between the fluids at the interface 1118 the fluids do not substantially mix at the interface 1118 such that a distinctive boundary line is apparent between the first and second fluids $F_a$, $F_b$. After this point, the first fluid source 1104a continues to deliver the first fluid $F_a$ at a first rate $Q_1$ while the second fluid source 1104b continues to deliver the second fluid $F_b$ at a second rate $Q_2$ that is slower than the first rate $Q_1$. As such, flow of the second fluid $F_b$ (i.e., the leakage flow) causes migration of the interface 1118 toward the receiving region 1112 (and thus the first fluid source). Accordingly, to achieve sequential delivery of the first fluid $F_a$ and the second fluid $F_b$ (in that order) without leakage, the first fluid $F_a$ must completely drain before the interface 1118 breaches the first fluid outlet 1114a (as shown in FIG. 11B).

Whether the leakage flow $Q_2$ overcomes the first flow $Q_1$ depends at least in part on the type of fluid sources (e.g., ideal or non-ideal). FIGS. 12A and 12B show the corresponding electrical circuit models for embodiments where the fluid sources 1104a, 1104b are non-ideal fluid sources. Solving these circuits provides:

$$Q_2 = \frac{P_{S1} - P_{S2}}{R_S}; \quad \text{(Equation 7)}$$

$$Q_1 = \frac{P_P - P_{S1}}{R(t)}; \text{ and} \quad \text{(Equation 8)}$$

$$\frac{Q_2}{Q_1} = \frac{R(t)[P_{S1} - P_{S2}]}{R_S[P_P - P_{S1}]} \quad \text{(Equation 9)}$$

According to Equations 7-9, when non-ideal fluid sources are used in pseudo-1DPN models, the second or leakage flow rate $Q_2$ is a function of the pressure differential between the first and second fluid sources 1104a, 1104b and the spacer region 1130 resistance $R_S$. Thus, the potential for leakage (e.g., the first-second interface 1118 breaches the first fluid outlet 1114a before the first fluid has completely drained) to occur will depend on the capillary backpressure $P_S$ of the non-ideal fluid source material and how the capillary backpressure $P_S$ changes as fluid is drained (see FIGS. 4-7). As with the 2DPN sequential delivery device 800 described above with reference to FIGS. 8-10, leakage caused by non-ideal fluid sources can be reduced by increasing the spacer resistance ($R_S$) (e.g., by increasing the length of the spacer region).

FIGS. 13A and 13B show the corresponding electrical circuit models for embodiments where the fluid sources 1104a, 1104b are ideal fluid sources. As shown, the capillary backpressure $P_S$ exerted by the first and second fluid sources 1104a, 1104b is negligible such that $P_{S1}=P_{S2}=0$. Modifying Equations 7-9 to reflect this distinction between ideal and non-ideal fluid sources, the leakage flow $Q_2$ is zero since no pressure differential acts between the first and second fluid sources 1104a, 1104b. Accordingly, unlike the case of non-ideal fluid sources, it is believed that ideal fluid sources in pseudo-1DPN models give clean (i.e., leakage-free) sequential delivery even for small spacing between fluid source outlets (e.g., small spacer region). Smaller spacing can reduce the total time for delivery. Moreover, ideal fluid sources in the pseudo-1DPN format should provide leakage free sequential delivery regardless of the volumes of fluid being applied. By contrast, the 2DPN format and/or the pseudo-1DPN format with non-ideal fluid sources must be redesigned to accommodate any volume changes.

c. Pseudo-1DPNs with Three Ideal Fluid Sources

Figure 14:
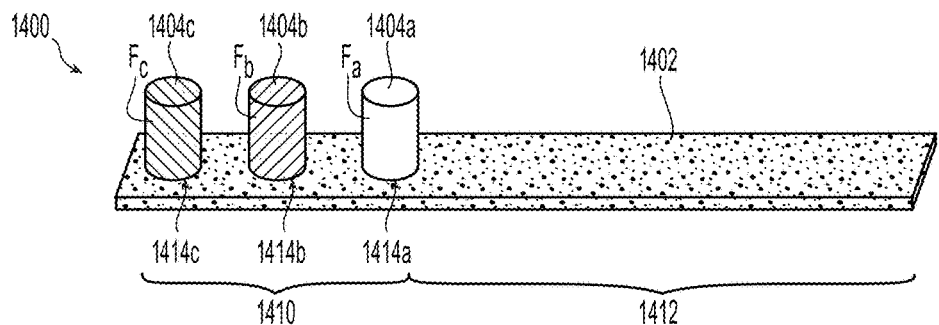
FIG. 14 is a perspective side view of a sequential delivery device having ideal fluid sources configured in accordance with an embodiment of the present technology.

FIG. 14 is a perspective side view of a sequential delivery device 1400 including a plurality of ideal fluid sources configured in accordance with the present technology. As shown in FIG. 14, the fluidic device 1400 can include a first fluid source 1404a, a second fluid source 1404b, a third fluid source 1404c, and a receiving element 1402. The receiving element 1402 can be any porous material such as a wick, pathway, or leg and can have an input region 1410 and a receiving region 1412. The fluid sources 1404a-1404c can each have an outlet 1414a-c positioned within the input region 1410 of the receiving element 1402. As such, the fluid sources 1404a-1404b are configured to be fluidly connected to the receiving element 1402. Although three fluid sources 1404a-c are shown in FIG. 14, in other embodiments the fluidic device 1400 can have less than three fluid sources (e.g., two fluid sources) or more than three fluid sources (e.g., four, ten, twenty, etc.).

The first, second and third fluid sources 1404a-c can be wells configured to hold a finite volume V of fluid. For example, in the illustrated embodiment, the first fluid source 1404a contains a first fluid $F_a$ having a first fluid volume $V_a$, the second fluid source 1404b contains a second fluid $F_b$ having a second fluid volume $V_b$, and the third fluid source 1404c contains a third fluid $F_c$ having a third fluid volume $V_c$. The first, second and third fluids $F_a$, $F_b$, $F_c$ (or a subset thereof), can be the same or different, and the first, second and third fluid volumes $V_a$, $V_b$, $V_c$ (or a subset thereof) can be the same or different. In some embodiments, for example, the fluid volumes can be between about 1 μL and 200 μL. In a particular embodiment, the fluid volumes can be between about 10 μL and 100 μL, or in some embodiments, between about 50 μL and 150 μL. The wells can be generally cylindrical and can have a diameter between about 0.1 mm and about 10 mm. In some embodiments, the wells can have a diameter between about 3 mm and about 5 mm. For ease of description, each fluid is depicted by a different fill pattern; such a depiction does not reflect on the composition or properties of the fluid.

The input region 1410 of the receiving element 1402 can generally comprise the portion of the receiving element 1402 adjacent the fluid source outlets 1414a-c. Although in the illustrated embodiment the main body of the fluid sources 1404a-c are also shown adjacent to the receiving element 1402, in other embodiments the main body of the fluid sources 1404a-c can be positioned a distance from the receiving element 1402. For example, in some embodiments the reservoir portion of the fluid source can be fluidly coupled to the receiving element 1402 via a connector (e.g., a pathway, a wick, tubing, etc.) (not shown).

As shown in FIG. 14, the fluid source outlets 1414a-c can be arranged in a line along the input region 1410. For example, the first fluid source outlet 1414a can be positioned closer to the receiving region 1412 than the second and third fluid source outlets 1414b, 1414c such that the first fluid source outlet 1414a is between the second and third fluid source outlets 1414b, 1414c and the receiving region 1412. The second fluid source outlet 1414b can be positioned closer to the receiving region 1402 than the third fluid source outlet 1414c such that the second fluid source outlet 1414b is located between the third fluid source outlet 1414c and the receiving region 1412, as well as between the first and third fluid source outlets 1414a, 1414c. The first, second, and third outlets 1414a-c can be separated by the same or different distances (measured between the perimeters of the outlets). In a particular embodiment, at least two of the outlets are separated by less than 10 mm, and in some embodiments, by less than 5 mm (e.g., 1 mm).

Figure 15A:
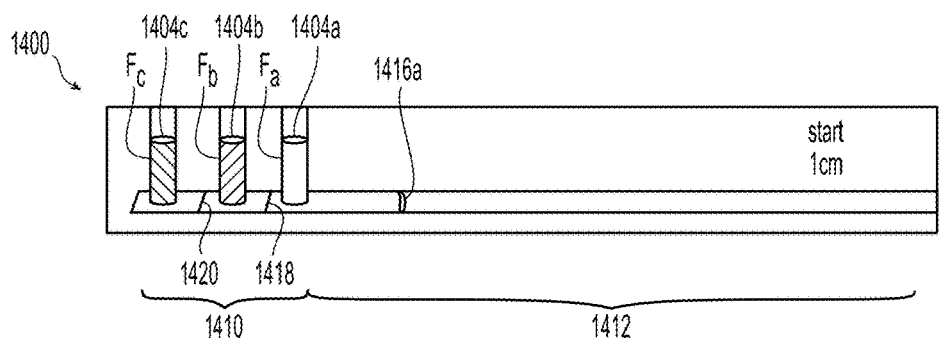
FIGS. 15A-15D are a series of time-lapsed side views of the sequential delivery device shown in FIG. 14.

FIGS. 15A-15D are time lapsed views of the fluidic device 1400 once the fluid sources 1404a-c have simultaneously been placed in fluid communication with the input region 1410. FIG. 15A shows the state of the device 1400 after the fluid sources 1404a-c have been connected to the input region 1410 and at least a portion of the first, second and third fluids $F_a$, $F_b$, $F_c$ empty into the input region 1410 (e.g., after the "wet-out" period). Soon thereafter, a first-second interface 1418 forms between the first and second fluids $F_a$, $F_b$, and a second-third interface 1420 forms between the second and third fluids $F_b$, $F_c$. Although a small amount of diffusive mixing occurs between the fluids at the interfaces 1418, 1420, the fluids do not substantially mix at the interfaces 1418, 1420 such that a distinctive boundary line is apparent between the two fluids. Although the interfaces 1418, 1420 may slowly migrate towards the receiving region 1412, the first-second interface 1418 remains proximal of the first fluid outlet 1404a and the second-third interface 1420 remains proximal of the second fluid outlet 1404b while the first fluid $F_a$ completely empties into the receiving element 1402. Likewise, the height of the second and third fluids $F_b$, $F_c$ within the second and third fluid sources 1404b, 1404c, respectively, remains relatively constant while the first fluid $F_a$ drains.

Figure 15B:
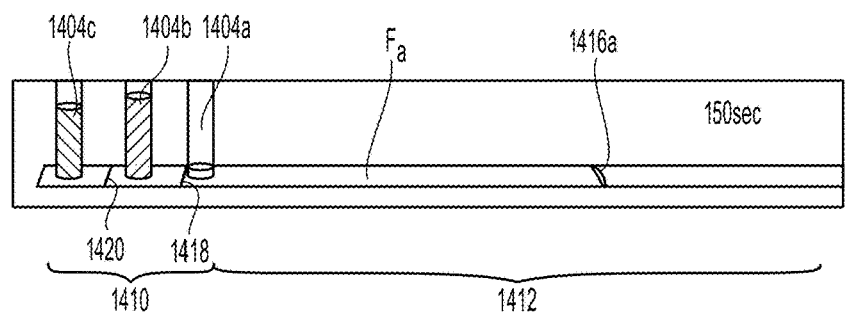
Figure 15C:
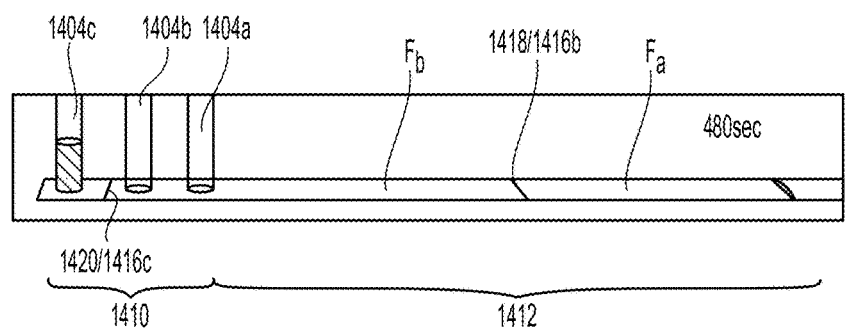
Figure 15D:
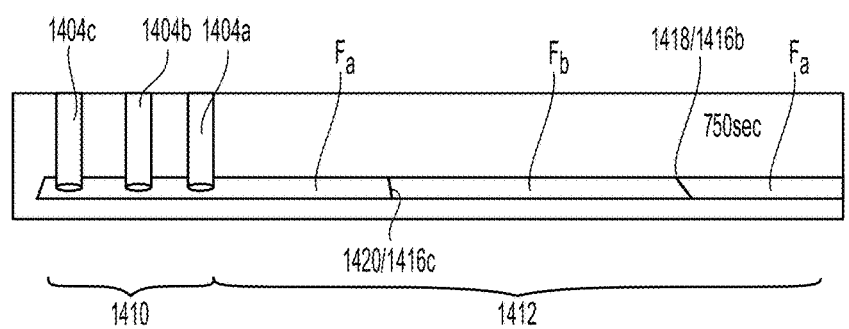

As the first fluid $F_a$ empties, the first fluid front 1416a moves distally along the receiving region 1412. Once the first fluid $F_a$ has emptied, the remaining volume of fluid $F_b$ in the second fluid source 1404b releases and empties into the receiving element 1402, as shown in FIGS. 15B and 15C. As the second fluid $F_b$ empties, the first and second fluid fronts 1416a, 1416b move distally along the receiving region 1412. While the second fluid $F_b$ drains, the second-third interface 1420 remains proximal of the second fluid outlet 1404b. Once the second fluid $F_b$ has emptied, the remaining volume of fluid $F_c$ in the third fluid source 1404c releases and empties into the receiving element 1402, as shown in FIGS. 15C and 15D. Accordingly, the device 1400 sequentially delivers the first, second, and third fluids $F_a$, $F_b$, $F_c$ to the receiving region 1412 without substantial mixing of the first, second, and third fluids $F_a$, $F_b$, $F_c$ at the interfaces 1418, 1420 and without leakage of an upstream fluid into a downstream fluid source (e.g., the first-second 1418 interface breaching the first outlet 1414a before the first fluid $F_a$ has completely emptied, the second-third interface 1420 breaching the second outlet 1414b before the second fluid $F_b$ has completely emptied, etc.).

d. Pseudo-1DPN's with Three Non-Ideal Fluid Sources

Figure 17:
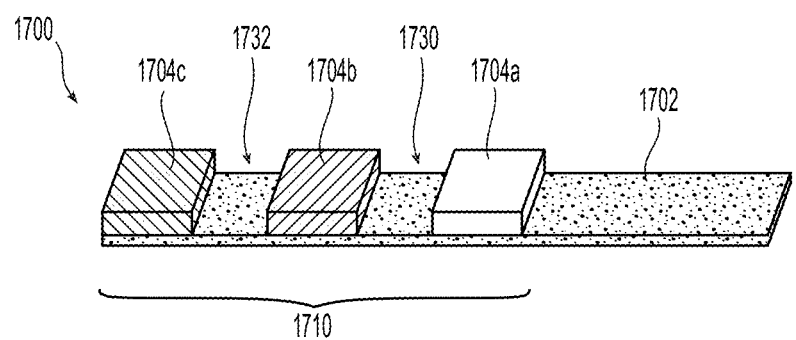
FIG. 17 is a perspective side view of a sequential delivery device having non-ideal fluid sources configured in accordance with an embodiment of the present technology.

FIG. 17 is a side perspective view of a sequential delivery device 1700 including a plurality of non-ideal fluid sources configured in accordance with the present technology. The sequential delivery device 1700 can be generally similar to the sequential delivery device 1400 except as detailed below. The non-ideal fluid sources 1704a-c can individually comprise a porous membrane (e.g., a pad) made of a non-ideal fluid source material, such as nitrocellulose, cellulose, glass fiber, and the like. Some or all of the fluid sources 1704a-c can comprise the same non-ideal fluid source material or different non-ideal fluid source materials. As shown in FIG. 17, the fluid sources 1704a-c can be positioned adjacent the receiving element 1702 such that the main body of the fluid sources 1704a-c are in direct contact with the receiving element 1702 along the input region 1710.

Figure 18A:
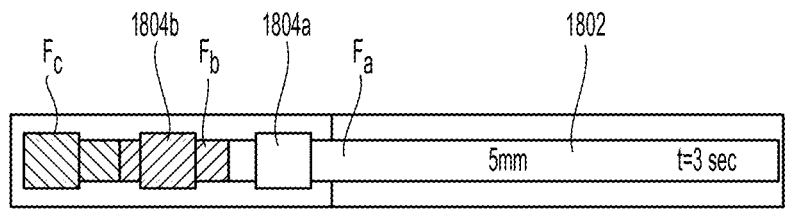
FIGS. 18A-18C are a series of time-lapsed side views of a sequential delivery device having non-ideal fluid sources illustrating leakage flow due to inadequate source spacing.
Figure 18B:
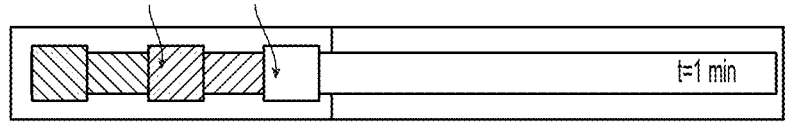
Figure 18C:
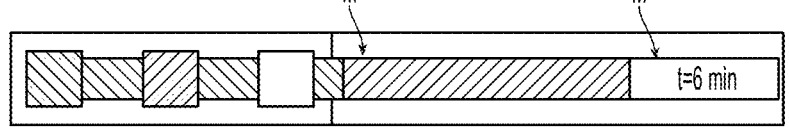
Figure 19:
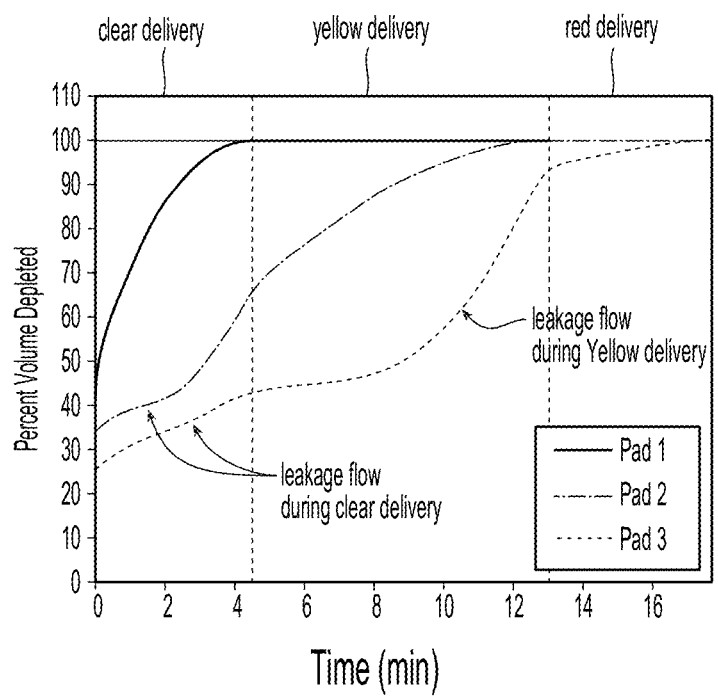
FIG. 19 is a computational model showing the percentage of fluid volume depleted versus time for the fluid flow shown in FIGS. 18A-18C.

As discussed above with reference to FIGS. 12A-12B, the capillary backpressures of non-ideal fluid sources create the potential for leakage to occur during fluid delivery. Such a leakage potential, however, can be reduced and/or eliminated by appropriate device design. By way of example, FIGS. 18A-18C are time-lapsed views showing fluid leakage during delivery due to inadequate source spacing. After wet-out, the second and third fluids $F_b$, $F_c$ continue to migrate, reaching the next downstream source (1804a, 1804b, respectively) before the source has completely drained. Such leakage causes unwanted mixing M to occur in both the second fluid source 1804b (i.e., at t=1 min) and the receiving element 1802 (exhibited by the long, extended second and third fluid fronts seen at t=6 min). Additionally, FIG. 19 shows a computational model that predicts leakage of the second and third fluids $F_b$, $F_c$ during delivery.

In contrast, FIGS. 20A-20C show time-lapsed views of the sequential delivery device 1700 providing sequential delivery without leakage. Although the fluid sources 1704a-c, fluids F, and receiving element 1702 are generally the same as those referred to in the failed example shown in FIGS. 18A-18C, the fluid sources 1704a-c in FIGS. 20A-20C are separated by a greater distance than in FIGS. 18A-18C. In other words, by increasing the length of the spacer regions 1730, 1732, no leakage occurred at the first or second fluid sources 1704a, 1704b. As a result, no obvious mixing of fluids occurs in either the fluid sources 1704a-c or at the fluid interfaces.

FIG. 21 shows a computational model that predicts device behavior given a specific spacer region length/resistance. The times $T_{mig}$ and $T_{drain}$ are used to determine device success. In the model, $T_{mig}$ is the time it takes for fluid from one pad to migrate from the middle of the spacer region (where initial wet-out has terminated) to the left boundary of the subsequent pad. $T_{drain}$ corresponds to the time required for this 'subsequent pad' to release all of its fluid. A successful device will have non-negative $T_{mig}-T_{drain}$ values for all pairs of pads. For example, relating this model to FIG. 17, $T_{mig}$ (second fluid $F_b$)$-T_{drain}$ (first fluid $F_a$) and $T_{mig}$ (third fluid $F_c$)$-T_{drain}$ (second fluid $F_b$) must both be greater than or equal to zero for the device 1700 to provide leakage-free sequential delivery. The plot of FIG. 21 is separated into three distinct regions: "both legs fail" (no clean delivery), "one leg fails" (clean delivery between the first and second fluid sources 1704a, 1704b), and "both legs succeed" (clean delivery between all sources 1704a-c). As predicted by the circuit model, increasing resistance within the spacer regions 1730, 1732 decreases the flow ratio between sources 1704a-c and improves the likelihood of leakage-free sequential delivery.

e. Devices and Methods for Fluidly Coupling Ideal Fluid Sources to a Porous Receiving Element Sequential delivery devices comprising ideal fluid sources of the present disclosure include devices wherein the substantially ideal fluid sources are not initially in fluid contact with the receiving element. In such devices, the fluid outlets can be separated from the receiving element by a fluid impermeable barrier. The device can further include a release element configured to disable the barrier. For example, in some embodiments, the device can include a release element in the form of a puncture element positioned adjacent the fluid source outlet. When pressure is applied to the fluid source and/or puncture element (or extension thereof), the puncture element punctures the fluid impermeable barrier, thereby placing the receiving element and the fluid source in fluid communication. In a particular embodiment, the device can include a release element in the form of a moveable barrier, such as a Teflon strip. The moveable barrier can be pulled or pushed out of position between the fluid outlet and the receiving element, thereby fluidly coupling the receiving element and the fluid source.

In some embodiments, the device includes multiple release elements, each configured to act on a corresponding fluid impermeable barrier. In other embodiments, the device can include a single release element configured to act on multiple barriers simultaneously.

Figure 22A:
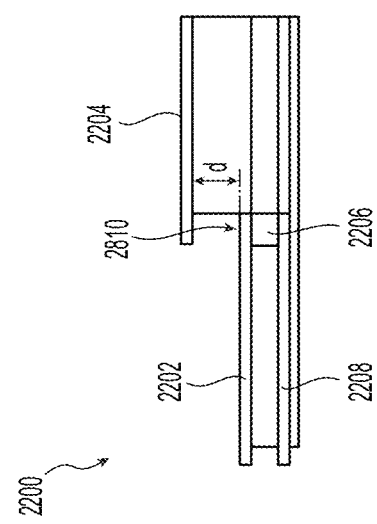
FIGS. 22A-22B are side views of a control device before and after activation configured in accordance with the present technology.
Figure 22B:
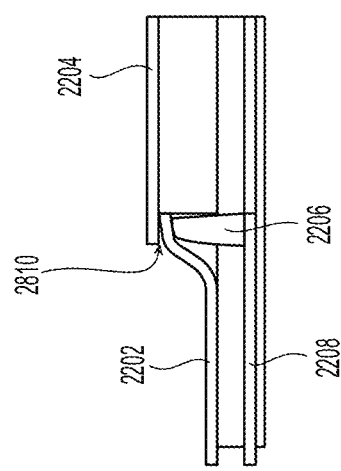

IV. SELECTED EMBODIMENTS OF DEVICES. SYSTEMS AND METHODS FOR CONTROLLING FLUID FLOW ON PAPER NETWORKS a. Actuatable Control Devices Performing integrated processes on 2DPNs (e.g., nucleic acid isolation, nucleic acid amplification, etc.) requires advanced fluid control techniques. FIGS. 22A-22B are side views of a control device 2200 configured in accordance with the present technology shown in the "off" and "on" positions, respectively. The control device 2200 can be configured to fluidly connect a first pathway 2202 and a second pathway 2204 separated by a distance d. The control device 2200 can include an expandable member 2206 fluidly coupled to a fluid delivery channel 2208 (e.g., a glass fiber pathway). The expandable member 2206 can be a polymer (e.g., sodium polyacrylate) or other material that expands when in contact with a fluid (e.g., deionized water). The control device 2200 can be positioned at or near a transfer portion 2210 of the first pathway 2202. The transfer portion 2210 can be aligned with at least a portion of the second pathway 2204. In some embodiments, while in the unexpanded state, the expandable member 2206 is in contact with the first pathway 2202. In other embodiments, when in the unexpanded state, the expandable member 2206 is adjacent, but not in contact with, the first pathway 2202. Regardless, when the activating fluid (not shown) flows through the delivery channel 2208 and contacts the expandable member 2206, the expandable member 2206 expands at least partially in the direction of the second pathway 2204, as shown in FIG. 22B. As the expandable member 2206 expands, the member 2206 pushes the transfer portion 2210 of the first pathway 2202 towards the second pathway 2204 until the first pathway 2202 contacts and is fluidly coupled with the second pathway 2204.

Figure 24:
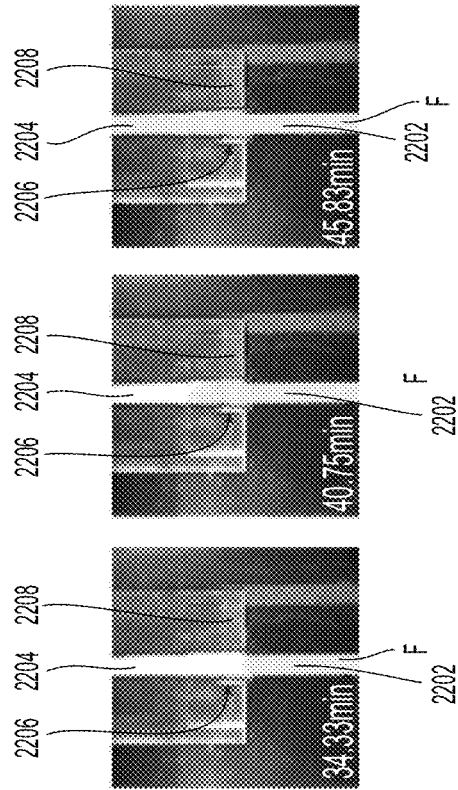
FIG. 24 is a series of time lapsed side views of a control device after activation configured in accordance with the present technology.
Figure 23:
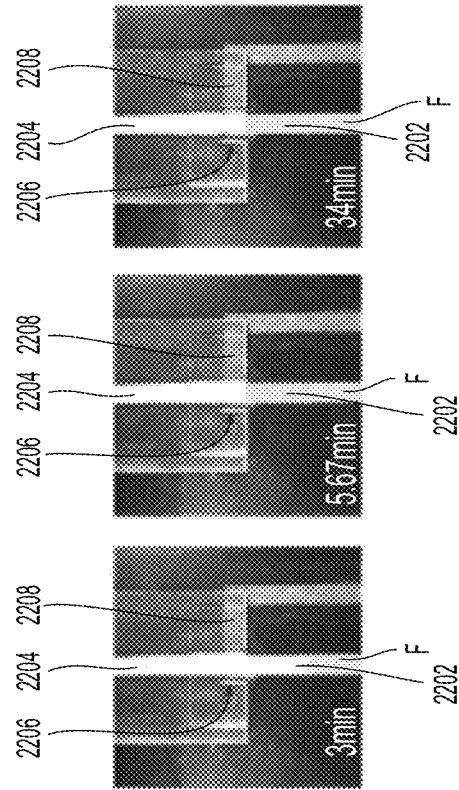
FIG. 23 is a series of time lapsed side views of a control device before activation configured in accordance with the present technology.

FIG. 23 is a series of time lapsed views showing the effect of the expandable member 2206 in a non-expanded state. As shown in FIG. 23, a fluid F wicks through the first pathway 2202 until reaching the expandable member 2206 in an unexpanded configuration. As such, the fluid F remains on the first pathway 2202 only and is not transferred to the second pathway 2204. FIG. 24 is a series of time lapsed views showing the transfer of a fluid F from the first pathway 2202 to the second pathway 2204 once an activating fluid reaches the expandable member 2206 and the expandable member 2206 expands to fluidly connect the first and second pathways 2202, 2204.

Figure 25A:
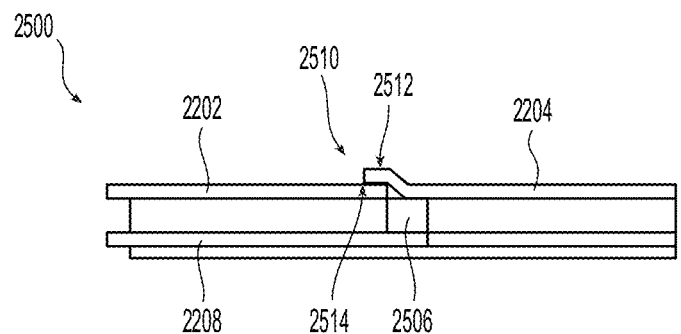
FIGS. 25A-25B are side views of a control device before and after activation configured in accordance with the present technology.
Figure 25B:
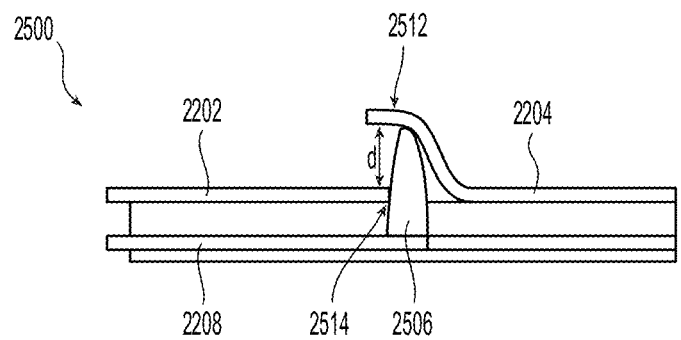

FIGS. 25A-25B are side views of another embodiment of a control device 2500 configured in accordance with the present technology shown in the "on" and "off" positions, respectively. In contrast to the control device 2200 shown in FIGS. 22A-24, the control device 2500 can be configured to fluidly disconnect the first and second pathways 2202, 2204 by separating the pathways 2202, 2204 by a distance d. The control device 2500 can include an expandable member 2506 and fluid delivery channel 2208 generally similar to the expandable member 2206 and fluid delivery channel 2208 shown in FIGS. 22A-24. The expandable member 2506 can be positioned at or near a connecting portion 2510 of the first and second pathways 2202, 2204. For example, the connecting portion 2510 can be where the first pathway connecting end 2514 overlaps or abuts a second pathway connecting end 2512. In some embodiments, while in the unexpanded state, the expandable member 2506 is in contact with the first and/or second pathways 2202, 2204. In other embodiments, when in the unexpanded state, the expandable member 2506 is adjacent, but not in contact with, the first and/or second pathways 2202, 2204. Regardless, when the activating fluid (not shown) flows through the delivery channel 2208 and contacts the expandable member 2506, the expandable member 2506 expands at least partially in the direction of the connecting portion 2510, as shown in FIG. 25B. As the expandable member 2506 expands, the member 2506 pushes the second pathway connecting end 2512 out of contact with the first pathway connecting end 2514 (or vice versa), thereby fluidly disconnecting the first and second pathways 2202, 2204.

Figure 26A:
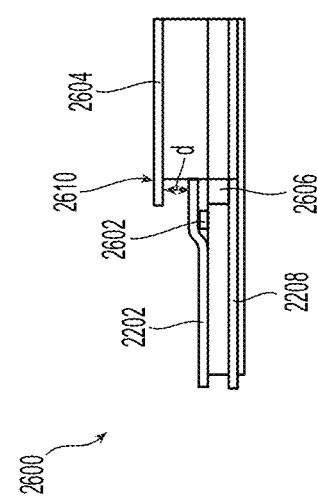
FIGS. 26A-26B are side views of a control device before and after activation configured in accordance with the present technology.
Figure 26B:
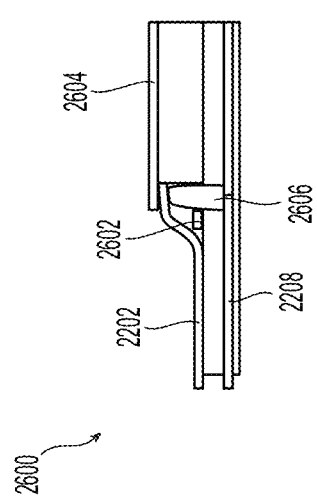

FIGS. 26A-26B are side views of another embodiment of a control device 2600 configured in accordance with the present technology shown in the "first" and "second" positions, respectively. The control device 2600 can include an expandable member 2606 and a fluid delivery channel 2208 generally similar to the expandable member 2206 and fluid delivery channel 2208 shown in FIGS. 22A-24. When in the first position, the expandable member 2606 is in an unexpanded state and allows fluid to flow from a first pathway 2202 to a second pathway 2602 (referred to as a "first route R1," best shown in FIG. 27). When in the second position, the expandable member 2606 is in an expanded state which disconnects the first route R1 and fluidly connects the first pathway 2202 to a third pathway 2604 (referred to as a "second route R2," best shown in FIG. 28) initially separated by a distance d. As such, the control device 2600 is configured to divert the flow of fluid from the first route R1 to the second route R2.

As shown in FIG. 26A, the expandable member 2606 can be positioned at or near an aligned portion 2610 of the first and third pathways 2202, 2604. In some embodiments, while in the unexpanded state, the expandable member 2606 is in contact with the first and/or second pathways 2202, 2602. In other embodiments, when in the unexpanded state, the expandable member 2606 is adjacent, but not in contact with, the first and/or second pathways 2202, 2602. Regardless, when the activating fluid (not shown) flows through the delivery channel 2208 and contacts the expandable member 2606, the expandable member 2606 expands at least partially in the direction of the third pathway 2604, as shown in FIG. 26B. As the expandable member 2606 expands, the member 2606 pushes the first pathway 2202 out of contact with the second pathway 2602 and into contact with the third pathway 2604, thereby fluidly disconnecting the first and second pathways 2202, 2602 and fluidly connecting the first and third pathways 2202, 2604.

Figure 27:
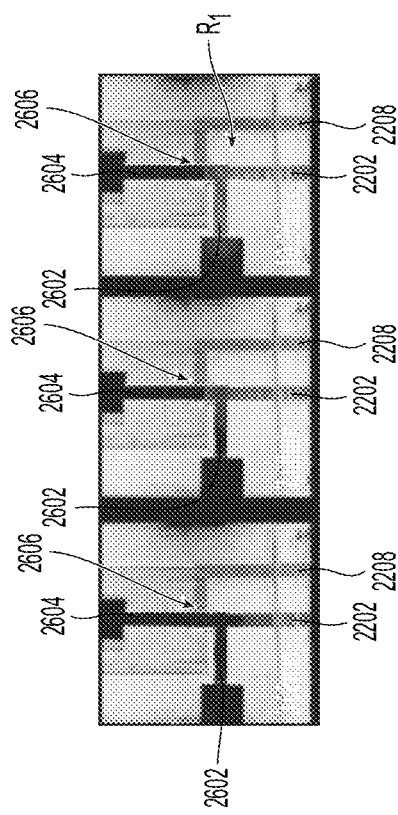
FIG. 27 is a series of time lapsed side views of a control device before activation configured in accordance with the present technology.
Figure 28:
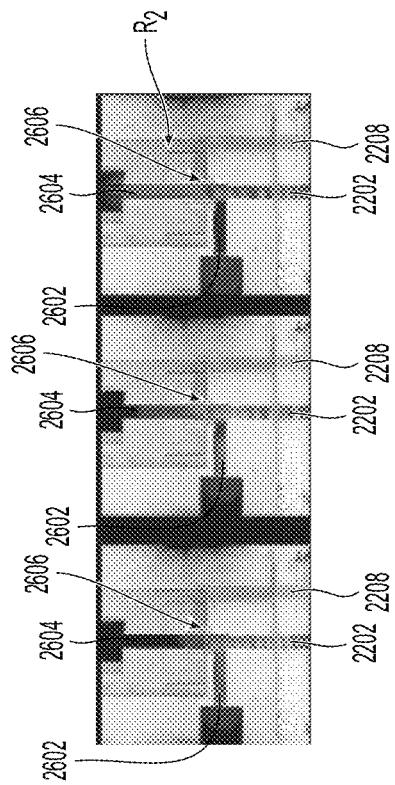
FIG. 28 is a series of time lapsed side views of a control device after activation configured in accordance with the present technology.

FIG. 27 is a series of time lapsed views showing the expandable member 2606 in a non-expanded state allowing fluid to flow only through the first route R1. As such, the fluid F remains within the first route R1 only and is not transferred to the second route R2 (FIG. 28). FIG. 28 is a series of time lapsed views showing the transfer of a fluid F from the first route R1 to the second route R2 once an activating fluid reaches the expandable member 2606 and the expandable member 2606 expands to fluidly connect the first and third pathways 2202, 2604.

In some embodiments the expandable member can be configured to fluidly connect (or disconnect) corresponding ends of two pathways, and in other embodiments the expandable member can fluidly connect (or disconnect) any portion of the first and second pathways (e.g., an end to a middle portion, a middle portion to a middle portion, a middle portion to an end, etc.). Additionally, a single expandable member can expand to simultaneously connect (or disconnect) a single first pathway to multiple second pathways, multiple expandable members can be used to connect (or disconnect) multiple first pathways to a single second pathway, and multiple expandable members can expand to connect (or disconnect) multiple first pathways to multiple second pathways. Multiple control devices can be utilized within a single fluidic device or LFT. Furthermore, in the illustrated embodiments the expandable member expands upwardly in a vertical plane; however, the expansion of the expandable member is not necessarily orientation specific, and in some embodiments the expandable member can expand in any direction (downwardly, diagonally, laterally, etc.).

b. Control of Activation Timing

Depending on the desired time for activation of the control device, the length of the delivery channel can be lengthened or shortened to increase or decrease (respectively) the time until activation of the expandable member. For example, FIGS. 29A-29D show several timing devices/delivery channels 2908 having varying lengths, and the graph in FIG. 30 shows the effect of the channel length on the delay time for activation of the expandable member 2906. As the channel length increases, so does the delay. FIGS. 31A-31C show time-lapsed top views of a delivery channel 2908 as an activation fluid F moves through the channel 2908 towards the expandable member 2906 (denoted by the movement of the fluid front 2910). As shown in FIGS. 31A-31C, the channel length can be accommodated by a serpentine configuration having multiple turns. Once the activation fluid F reaches the expandable member 2906, the fluid within the first pathway 2902 is allowed to flow into the second pathway 2904, as shown in FIGS. 31D-31F.

Figure 33:
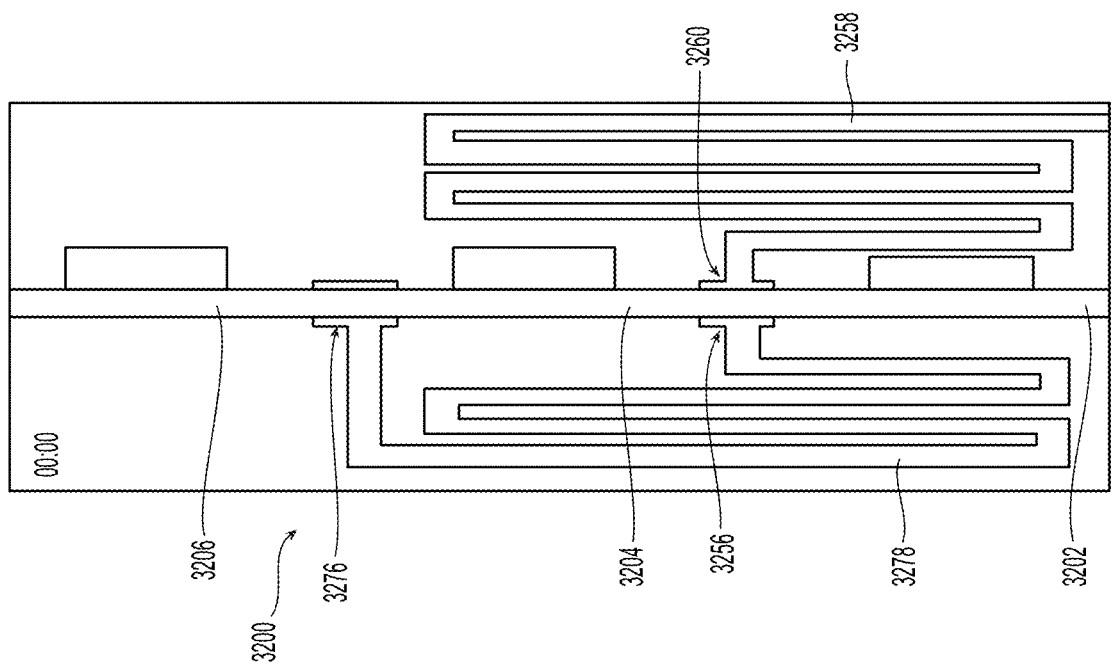
FIG. 33 is a top view of a portion of a fluidic device comprising multiple control devices configured in accordance with the present technology.
Figure 32A:
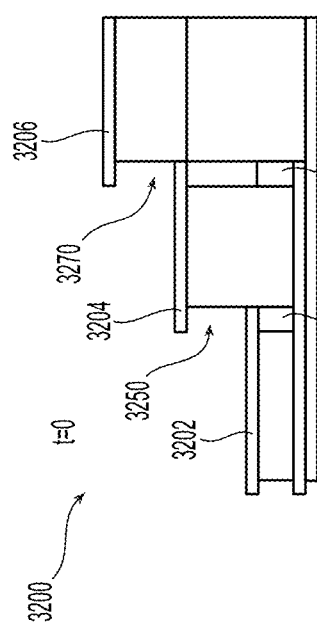
FIGS. 32A-32C are side views of a portion of a fluidic device comprising multiple control devices configured in accordance with the present technology.

In some embodiments, multiple channels having different lengths can be used to control the activation of multiple expandable members. FIGS. 32A and 33 are side and top views of one such fluidic device 3200 configured in accordance with the present technology. The fluidic device 3200 can include a first control device 3250 and a second control device 3270. The first control device 3250 can include a first expandable member 3256 aligned with a first pathway 3202 and a second pathway 3204, and the second control device 3270 can include a second expandable member 3276 aligned with the second pathway 3204 and a third pathway 3206. The first expandable member 3256 can be coupled to a first delivery channel 3258, and the second expandable member 3276 can be coupled to a second delivery channel 3278. The first and second delivery channels 3258, 3278 can be in fluid communication at or near the first expandable member 3256 via a bridge 3260. The first and second delivery channels 3258, 3278 can have the same or different lengths, depending on the desired expandable member activation timing. In the illustrated embodiment, the first delivery channel 3258 is longer than the second delivery channel 3278.

Figure 32B:
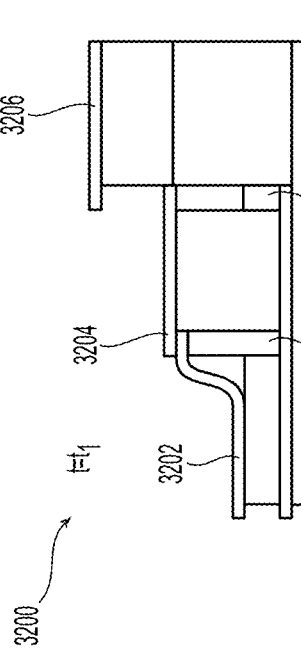
Figure 32C:
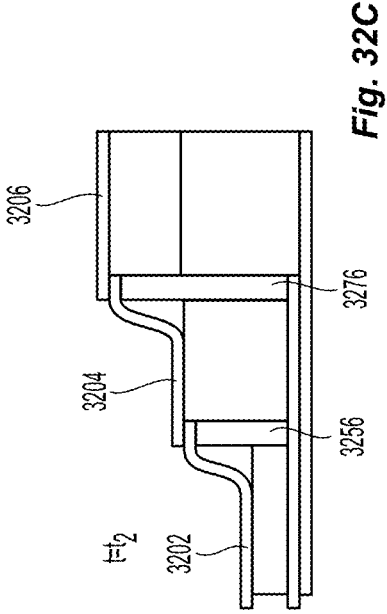

In operation, the activation fluid flows through the first delivery channel 3258 and activates the first expandable member 3256, thereby expanding the first expandable member 3256 and fluidly connecting the first and second pathways 3202, 3204 (as shown in FIG. 32B). The activation fluid then continues to flow across the bridge 3260 to the second delivery channel 3278, towards the second expandable member 3276. Eventually, the second expandable member 3276 is activated by the activation fluid, thereby expanding the second expandable member 3276 and fluidly connecting the second and third pathways 3204, 3206 (as shown in FIG. 32C).

c. Waste Removal Devices

Figure 34A:
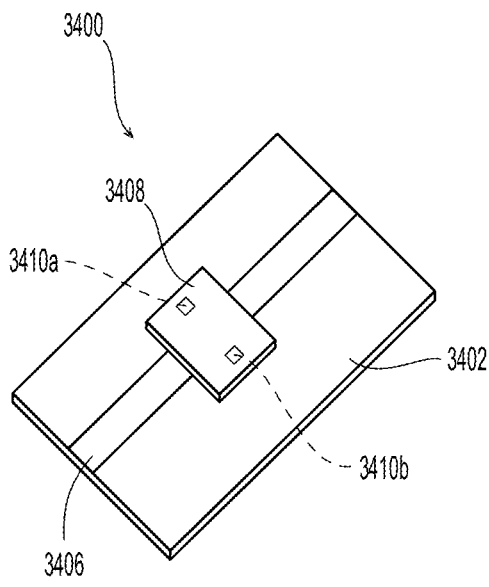
FIGS. 34A-34B are top perspective views of a waste removal system configured in accordance with the present technology.
Figure 34B:
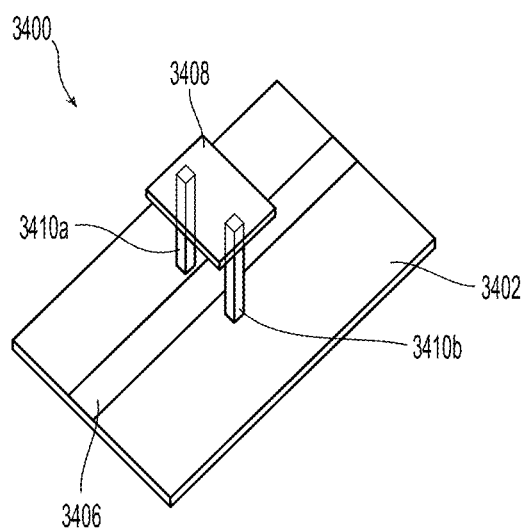

Often times it is necessary to use a waste pad at various locations along a fluidic network to collect waste. FIGS. 34A-34B show one embodiment of a waste removal device 3400 ("device 3400") configured in accordance with the present technology. The waste removal device 3400 can include a base 3402, a porous element 3406, and a waste pad 3408 (e.g., nitrocellulose, cellulose, etc.). The porous element 3406 can be positioned on the base 3402 and the waste pad 3408 can be positioned on and in fluid communication with the porous element 3406. The device 3400 can further include two expandable materials 3410a, 3410b positioned on either side of the porous element 3406. In operation, at least a portion of the fluid flowing through the porous element 3406 gets trapped within the waste pad 3408. At some point the waste pad 3408 may become saturated and/or it may become desirable to remove the waste pad 3408 from the path of fluid flow. As shown in FIG. 34B, the expandable materials 3410a, 3410b can be expanded (via an activation fluid, not shown) to push the waste removal pad 3408 away (upwardly, downwardly, laterally) from the porous element 3406. In some embodiments, the device 3400 can include less or more than two expandable materials. For example, in embodiments utilizing only one expandable material, the expandable material can be positioned at one end of the waste pad and expansion of the waste removal device angles the waste pad enough to move the waste pad out of fluid communication with the porous element (e.g., a lean-to configuration).

Figure 35A:
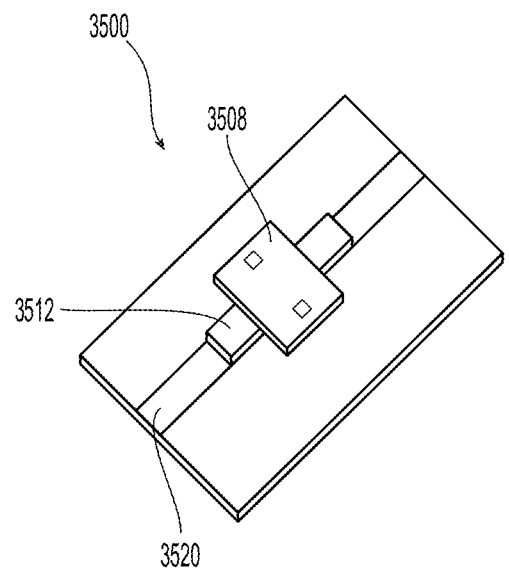
FIGS. 35A-35B are top perspective views of another embodiment of a waste removal system configured in accordance with the present technology.
Figure 35B:
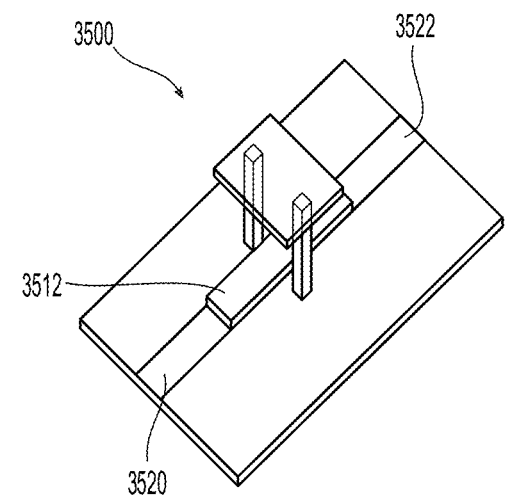

FIGS. 35A-35B show another embodiment of a waste removal device 3500 ("device 3500") configured in accordance with the present technology. The device 3500 can be generally similar to the device 3400 discussed above with reference to FIGS. 34A-34B except as described below. The device 3500 can include a first pathway 3520 fluidly coupled to a second pathway 3522 by a third pathway 3512. The waste pad 3508 can be positioned on the third pathway 3512.

The first and second pathways 3520, 3522 can have an initial internal resistance that is less than that of the third pathway 3512. For example, the first and second pathways 3520, 3522 (e.g., nitrocellulose, cellulose, etc.) can have a smaller pore size than the third pathway 3512 (e.g., glass fiber). As such, at least initially, fluid flows faster through the third pathway 3512 (relative to the first and second pathways 3520, 3522) and is wicked into the waste removal pad 3508 at a faster rate.

d. Volume-Metering Elements

Figure 36A:
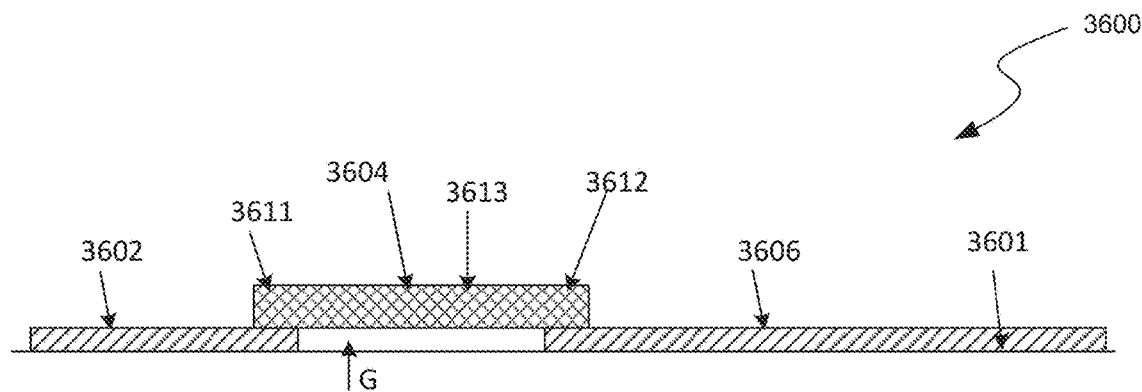
FIGS. 36A-36C are a series of time-lapsed side views of a pathway having a volume-metering element configured in accordance with an embodiment of the technology.
Figure 36B:
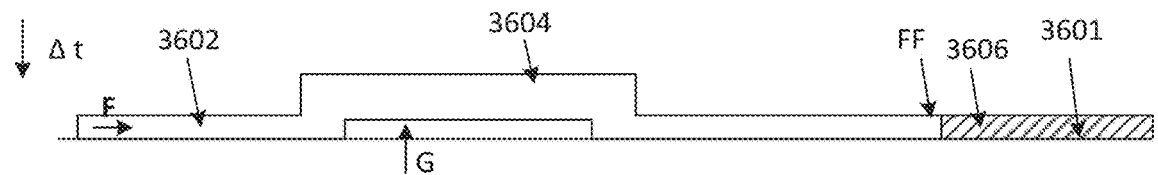
Figure 36C:
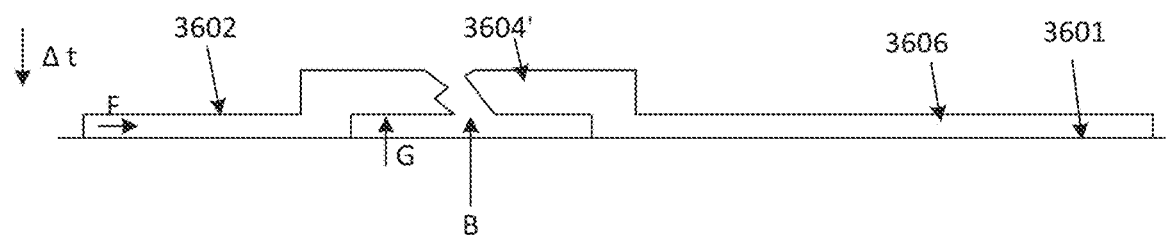

FIGS. 36A-36C are a series of time-lapsed side views of a pathway 3600 on a supporting surface 3601 configured in accordance with an embodiment of the technology. As shown in FIG. 36A, the pathway 3600 includes a first porous material or feeder material 3602 and a second porous material or delivery material 3606 connected by a volume-metering element 3604 therebetween. The volume-metering element 3604 can have a first portion 3611 in contact with the first porous material 3602, a second portion 3612 in contact with the second porous material 3606, and a third portion 3613 between the first portion 3611 and the second portion 3612 and separated from the supporting surface 3601 by a gap G. The volume-metering element 3604 can comprise a dissolvable or soluble material configured to automatically and independently control or modify a volume of fluid flow between the first material 3602 and the second material 3606. The first and second materials 3602, 3606 can include, for example, porous materials such as paper, glass fiber, polyester, nitrocellulose, cellulose, polymer membranes (e.g., cellulose acetate, cellulose esters, polysulfone, polyether sulfone, polyacrilonitrile, polyamide, polyimide, polyethylene and polypropylene, polytetrafluoroethylene, polyvinylidene fluoride, polyvinylchloride, etc.) and other suitable materials. In other embodiments, however, the first material 3602 and/or second material 3606 may include different materials and/or have a different arrangement.

Referring next to FIG. 36B, when fluid F is added to the first material 3602, the fluid F wicks (e.g., by capillarity force) from the first material 3602 to the volume-metering element 3604 to the second material 3606. As such, the volume-metering element 3604 initially functions as a bridge connecting the first material 3602 and the second material 3606. Over time, the fluid F dissolves the soluble material comprising the volume-metering element 3604 so that once a precise volume of fluid F passes through the element 3604, the element 3604 or at least a portion of the element 3604 breaks B (as shown in FIG. 36C) and permanently disconnects the first material 3602 from the second material 3606. As discussed in greater detail below with reference to FIGS. 37-39, the delivered volume can be precisely tailored by adjusting one or more pathway parameters, such as the cross-sectional area of the volume-metering element 3604, the material composition of the volume-metering element 3604, the flow rate of fluid into the element 3604 from the first material, the choice of first material 3602, and/or the choice of second material 3606.

Figure 37:
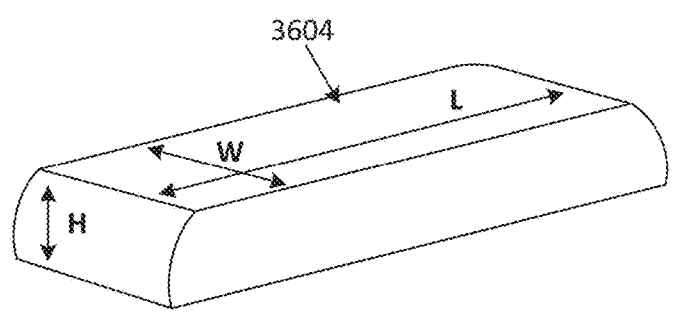
FIG. 37 is a perspective view of a volume-metering element configured in accordance with an embodiment of the present technology.

FIG. 37 is a perspective view of the volume-metering element 3604 configured in accordance with the present technology. As shown in FIG. 37, the volume-metering element 3604 can have a generally rectangular shape. In some embodiments, the volume-metering element 3604 may be made of one or more sugars. For example, the volume-metering element can comprise one or more monosaccharides (e.g., mannose, dextrose, fructose, galactose, etc.), disaccharides (e.g., trehalose, sucrose, lactose, maltose, etc.), sugar alcohols (e.g., mannitol, xylitol, sorbitol, etc.), polysaccharides (e.g., dextrans, maltodextrin, starch, etc.), one or more dextran derivatives (dextran sulfate) and/or other suitable sugars. Sugars are compatible with most common lateral flow assay reagents and, as a result, are often used in such assays for preservation of a dried gold label conjugated to antibody. In some embodiments, for example, volume-metering elements 3604 composed of high concentrations of sugar solutions can be used with the generation of a downstream lateral flow assay signal in a lateral flow format. In particular embodiments, for example, the volume-metering element 3604 can include partially or fully saturated solutions of trehalose spiked with antigen and applied to a lateral flow strip containing dried gold label conjugated to antibody and patterned with PfHRP2 capture antibody downstream. In other embodiments, however, the volume-metering element 3604 can have any suitable shape (e.g., square, circle, oval, octagon, ellipse, etc.), size, or configuration, and can be made of any solvent soluble composition capable of bridging a physical gap between two or more porous matrices and predictably dissolving and separating as described in the present disclosure. For example, in some embodiments the volume-metering element 3604 can comprise a salt, alginate, and/or carrageenan.

The volume-metering element 3604 can have a material composition, length L, width W, height H and/or cross-sectional area designed to pass a pre-defined volume of fluid before dissolving and breaking the fluid connectivity of the pathway 3600. For example, in some embodiments the volume-metering element 3604 can have a length L between about 6.5 and 8.5 mm (e.g., about 7.5 mm), a width W between about 2 mm and about 4 mm (e.g., about 3 mm), and a height H between about 0.1 mm and about 1.0 mm (e.g., about 0.2 mm, 0.3, 0.4 mm, 0.5 mm, 0.6 mm, etc.). The approximate volume of fluid passed by the volume-metering element 3604 can be measured using the location of the fluid front FF (FIG. 36B) within the second material 3606 at the time of element 3604 disconnection or shut-off. The volume delivered, V, at each time point, t, can be approximated by the equation $V(t)=(P*h*A*t)$, where P is the porosity of the second material 3606, h is the height of the second material, and A is the area occupied by the fluid F parallel to flow.

Figure 38:
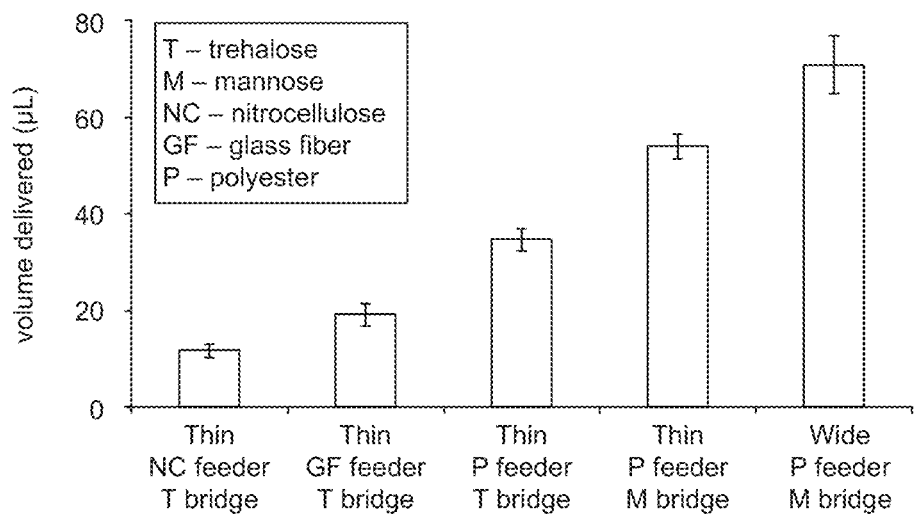
FIGS. 38 and 39 are graphs illustrating volumes of fluid delivered for various volume-metering elements configured in accordance with embodiments of the technology.
Figure 39:
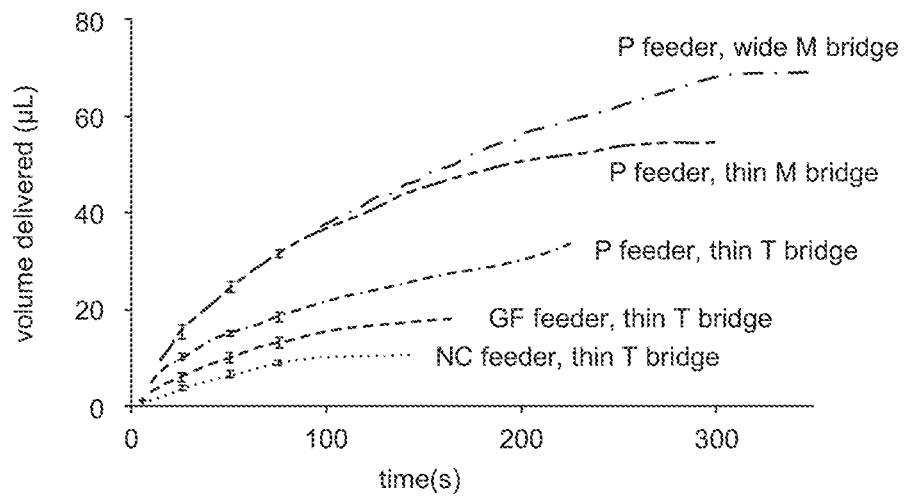

As previously mentioned, the passable volume allowed by the volume-metering element 3604 can be tailored by adjusting one or more pathway parameters. FIG. 38, for example, is a graph displaying the volume of fluid delivered for each volume-metering element 3604 where the first material 3602, the cross-sectional area of the volume-metering element 3604, and the material composition of the volume-metering element 3604 were adjusted to achieve a range of volumes delivered (e.g., between about 10 μl and about 80 μl). As shown in FIG. 38 and without being bound by theory, it is generally believed that (1) a volume-metering element 3604 having a greater width W will pass a greater volume than a volume-metering element having a smaller width W, (2) the material composition of the volume-metering element 3604 can affect the passable volume (e.g., all else generally equal, mannose can pass a larger volume than trehalose), and (3) the material composition of the first or feeder material can affect the passable volume (e.g., all else generally equal, glass passes a great volume than polyester that passes a greater volume than nitrocellulose). FIG. 39 is a graph displaying the change in volume of fluid delivered over time for each of the combinations of pathway parameters shown in FIG. 38. As shown, the volume of fluid exiting the volume-metering element 3604 is affected by the flow-rate of fluid entering the element 3604 from the first or feeder material. It will be appreciated that the specific examples illustrated in FIGS. 38 and 39 are merely representative of particular embodiments of the present technology, and that the first material 3602, the second material 3606, and/or volume-metering element 3604 may have different arrangements and/or different features in other embodiments.

Figure 40A:
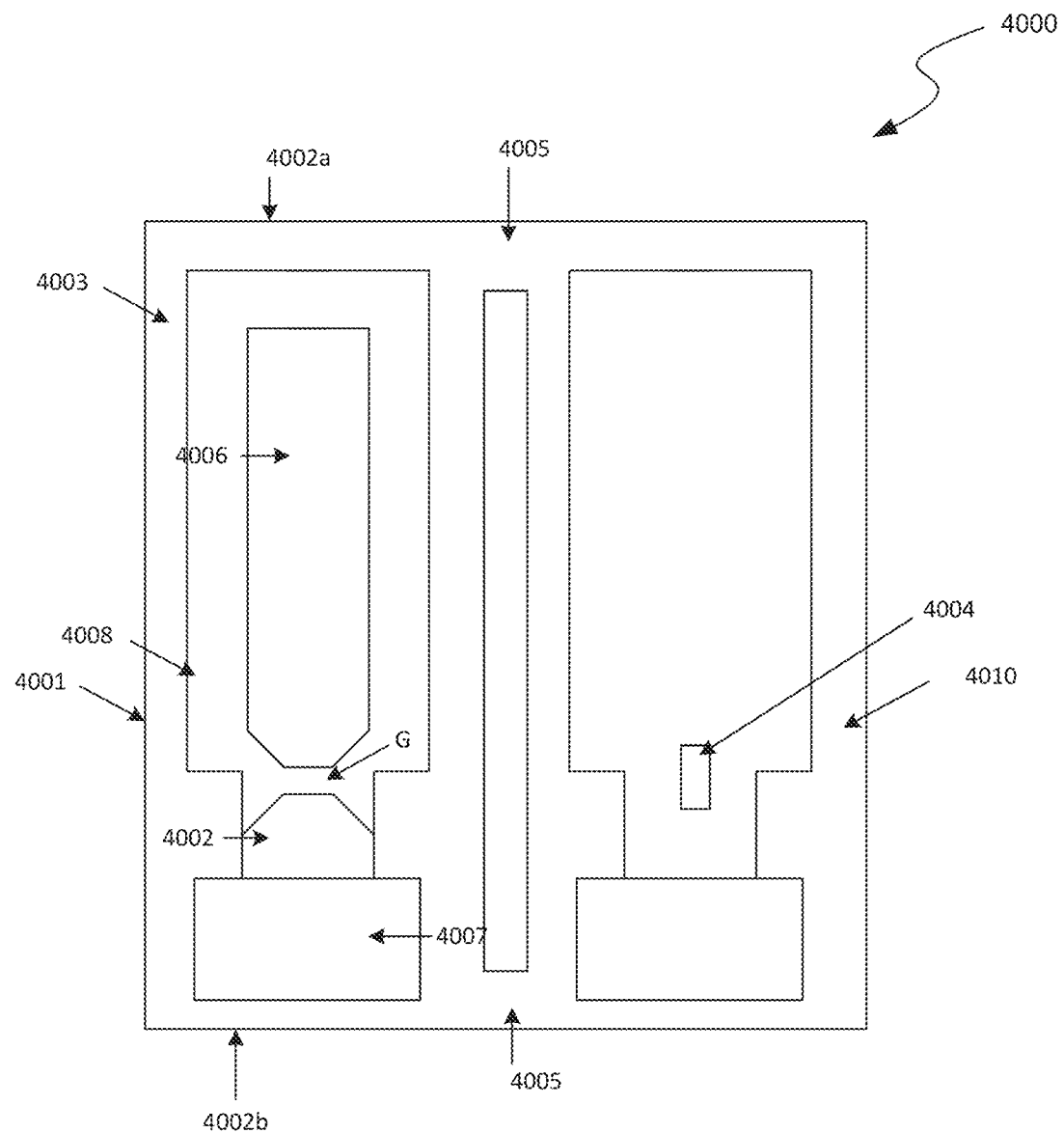
FIG. 40A is a top view of a capillarity-based device in the open position configured in accordance with an embodiment of the technology.
Figure 40B:
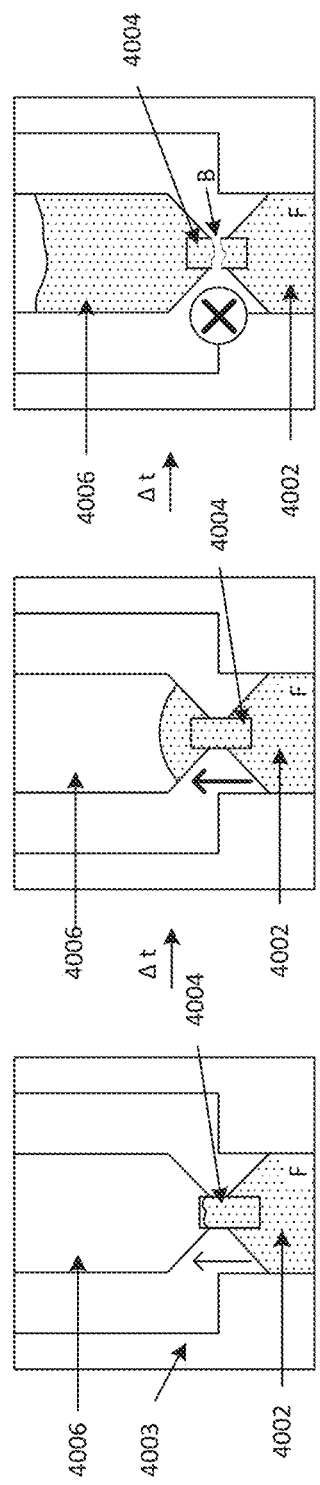
FIG. 40B is a series of time-lapsed top views of the capillarity-based device of FIG. 40A in the closed position and after fluid has been added configured in accordance with an embodiment of the technology.

FIG. 40A is a top view of a microfluidic device or analyzer 4000 configured in accordance with an embodiment of the present technology. The device 4000 can include a thin, foldable housing 4002 moveable between an open position (FIG. 40A) and a closed position (a portion of which is shown in FIG. 40B). The housing 4003 can have a first end 4002a opposite a second end 4002b, and a bottom layer 4008 and a top layer 4010 connected by one or more flexible connectors or hinges 4005. The bottom layer 4008 of the housing 4003 can support at least a portion of one or more fluid pathways 4001 and the top layer 4010 can have a volume-metering element 4004 removably attached thereto. It should be noted that although various aspects of the device 4000 are described as "top" or "bottom," such descriptors are for illustrative purposes only and do not limit the device 4000 or any component thereof to a specific orientation.

The fluid pathway 4001 can include a first material 4002 separated from a second material 4006 by a gap G. The first and second materials 4002 and 206 may be generally similar to the first and second materials 3602 and 3606 described above, or they may have a different configuration. In some embodiments, the pathway 4001 can optionally include a fluid source 4007 adjacent to the first material 4002 proximate the first end 4002a of the housing 4003. The fluid source 4007 can be configured to receive and contain a volume of fluid F (e.g., from a pipette) and supply at least a portion of that volume to the first material 4002 during the assay. In other embodiments, the device 4000 does not include a source 4007 and fluid is delivered directly to the first material 4002. The volume-metering element 4004 can be positioned on the top layer 4010 so that when the top layer 4010 is folded onto the bottom layer 4008 (or vice versa), the volume-metering element 4004 aligns with the gap G between the first material 4002 and the second material 4006, thereby providing a bridge between the first and second materials 4002, 4006.

In operation, fluid F is loaded into the source 4007 and the housing is moved into the closed position to bring the volume-metering element 4004 into contact with the first material 4002, thereby completing the pathway 4001. Within the pathway 4001, fluid flows by capillarity force from the source 4007 to the first material 4002, to the volume-metering element 4004, and finally to the second material 4006. FIG. 40B, for example, is a series of time-lapsed top views of the pathway 4001 after fluid F has been added to the source 4007 and the housing 4003 is placed in the closed position. As shown, once a precise volume of fluid F flows through the volume-metering element 4004, the element 4004 dissolves to the point of breaking (break B shown in FIG. 40B), thereby permanently disconnecting fluid F flow between the first material 4002 and the second material 206.

Figure 41A:
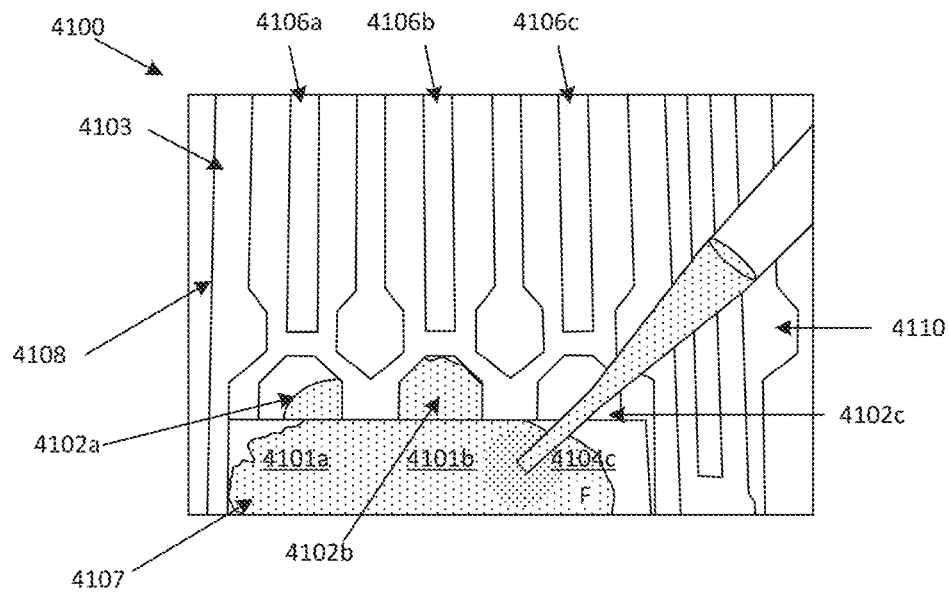
FIGS. 41A-41C and 42 show a series of time-lapsed top views of a capillarity-based device having multiple pathways configured in accordance with an embodiment of the present technology.
Figure 41B:
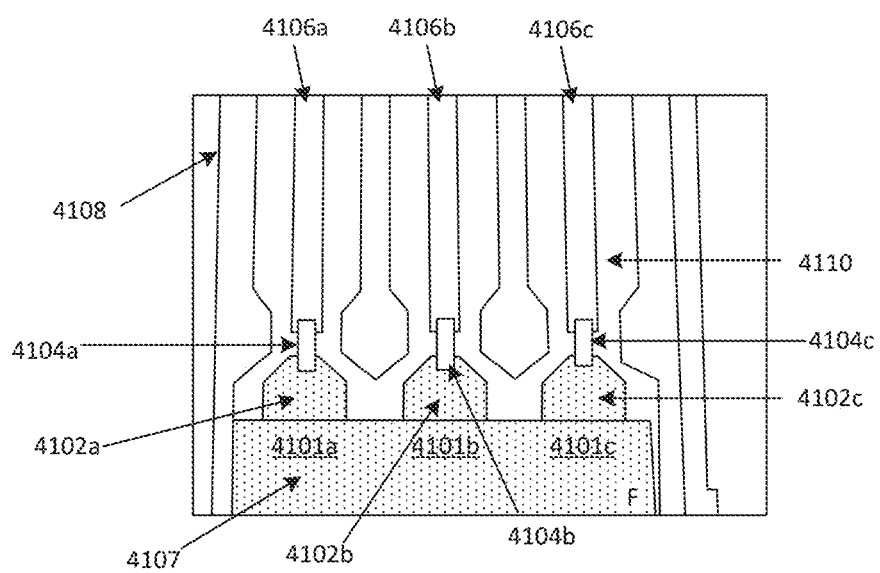

FIGS. 41A-41C and 42 show a series of time-lapsed top views of another capillarity-based device or analyzer 4100 utilizing volume-metering elements 4104 configured in accordance with the present technology to automatically dispense different fluid volumes to multiple pathways for downstream processing in a network from a single, user-filled source 4107. As shown in FIG. 41A, for example, the device 4100 can include three pathways 4101 (individually labeled at 4101a-4101c) and a single source 4107 servicing all three pathways. In other embodiments, the device 4100 can include any number of pathways (e.g., two, four, etc.) and/or a separate source for each pathway and/or subset of pathways. Each of the pathways 4101 can have different first materials 4102 (individually labeled 4102a-4102c) so that one or more of the pathways 4101a-4101c can deliver the same or a different volume to the second materials 4106 (individually labeled 4106a-4106c). For example, first material 4102a can comprise nitrocellulose, first material 4102b can comprise glass fiber, and first material 4102c can comprise treated polyester. In other embodiments, any of the pathways can have the same and/or different pathway parameters to tailor the passable volume to the particular needs of the assay.

Figure 41C:
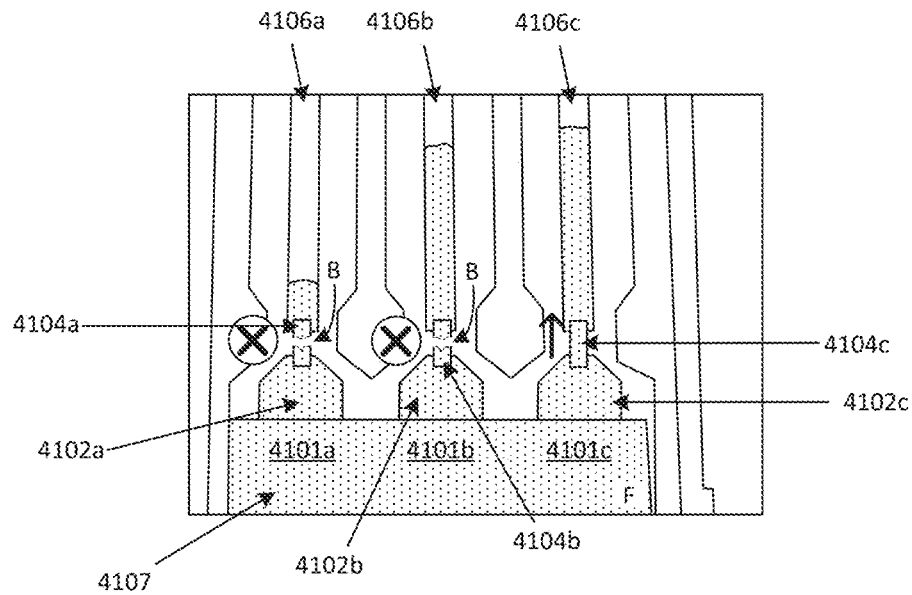
Figure 42:
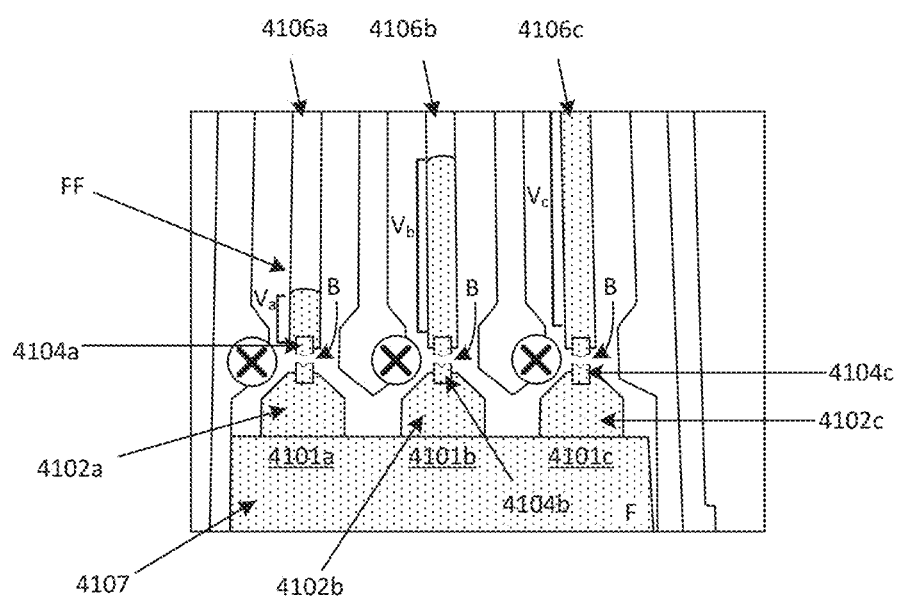

As shown in FIG. 41A, a fluid F can be added to the single source 4107 (e.g., using a plastic transfer pipette). The device 4100 can then be folded on itself, thereby connecting the first materials 4102 to the second materials 4106 via the respective volume-metering elements 4104 (individually labeled 4104a-4104c) for each pathway (shown mid-folding in FIG. 41B). As shown in FIG. 41C, the volume metering elements 4104a, 4104b attached to the nitrocellulose first material 4102a and the glass fiber first material 4102b, respectively, can disconnect or shut-off before the volume-metering element 4104c associated with the polyester first material 4102c. As shown in FIG. 42, the different final volumes delivered to the three pathways ($V_a$, $V_b$, $V_c$) can be observed in the different volumes occupied by the fluid front FF in the respective second materials 4106a, 4106b, 4106c. In one particular embodiment, for example, the three fluid volumes delivered for the described pathway configurations of FIGS. 41A-41C and 42 can be about 9.5 µL, about 22 µL, and about 31 µL for pathway 4105a, 4105b and 4105c, respectively. In other embodiments, however, different volumes of fluid may be delivered via the different pathways.

In some embodiments, a microfluidic device or analyzer configured in accordance with another embodiment of the present technology to automatically dispense different fluid volumes to multiple pathways for downstream processing in a network from a single, user-filled well is provided. For example, a bottom layer of the device can include four pathways and a single well servicing all four pathways. In other embodiments, the device can include any number of pathways (e.g., two, three, five, etc.) and/or a separate well for each pathway and/or subset of pathways. The first materials, second materials, volume-metering elements, and sources may be generally similar to the first materials, second materials, volume-metering elements, and sources described above, or they may have a different composition and/or configuration.

Each of the pathways can have different first materials and/or volume-metering element compositions so that one or more of the pathways can deliver the same or a different volume to the respective second materials. Each of the pathways can optionally include a source adjacent to and in fluid connection with the second materials. A top layer of the device can include one or more inlets adjacent to and in fluid connection with a network of pathways. The inlets can be positioned on the top layer such that when the top layer is folded onto the bottom layer (or vice versa), the sources align with the respective inlets. As a result, once the housing is folded and the sources make contact with the inlets, fluid from the sources can flow onto and through the inlets and to the network.

In operation, when fluid is added to the first materials (e.g., either directly or via the well), the fluid wicks (e.g., by capillary force) from the first materials to the respective volume-metering elements to the respective second materials to the respective sources. Depending on the prescribed passable-volume for each pathway, the time it takes the passable volume to reach the source (and the respective volume-metering element to dissolve and break) can be the same and/or different for all or a subset of the pathways.

In some embodiments, any of the pathways disclosed herein can include additional first and/or second materials in series along the same pathway connected by an additional flow-metering element (not shown). Further, in particular embodiments, a single pathway can have multiple branches (not shown) that converge and/or diverge. Examples of these and other suitable pathways and/or capillarity devices are described in International Patent Application No. PCT/US2010/061675, filed Dec. 21, 2010, titled "CAPILLARITY-BASED DEVICES FOR PERFORMING CHEMICAL PROCESSES AND ASSOCIATED SYSTEMS AND METHODS," and International Patent Application No. PCT/US2012/044060, filed Jun. 6, 2012, titled "REAGENT PATTERNING IN CAPILLARITY-BASED ANALYZERS AND ASSOCIATED SYSTEMS AND METHODS," both of which are incorporated herein by reference in their entireties.

e. Fluidic Actuators

Figure 43:
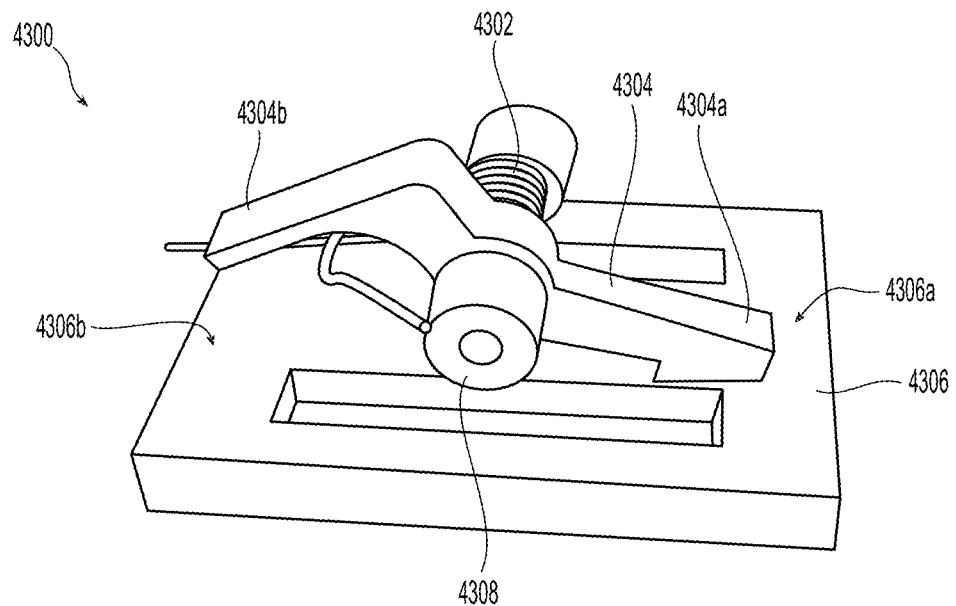
FIG. 43 is a side perspective view of an actuator configured in accordance with an embodiment of the present technology.
Figure 44:
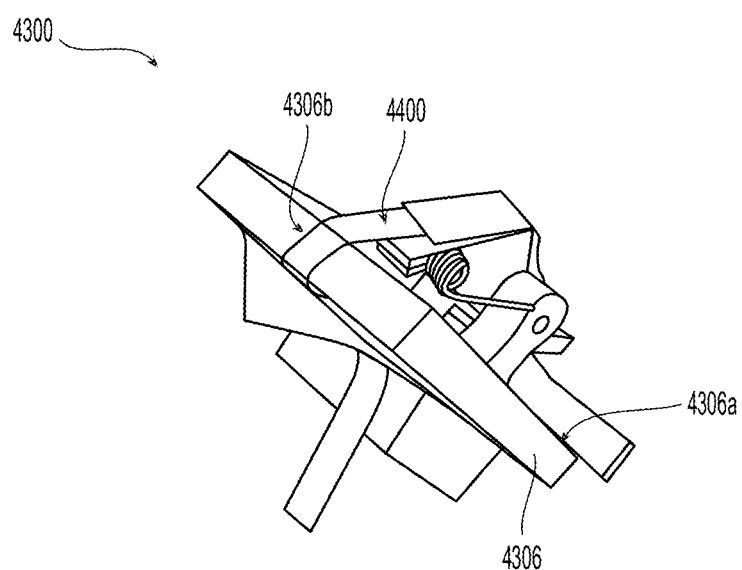
FIG. 44 is a perspective view of an actuator coupled to a dissolvable pathway configured in accordance with an embodiment of the present technology.

FIG. 43 is a side perspective view of a fluidic actuator or valve 4300 configured in accordance with the present technology. The actuator 4300 can include a base 4306 and an arm 4304 pivotally coupled to an extension 4308 protruding upwardly from the base 4306. The arm 4304 can be moveable between a first position (shown in FIG. 43) and a second position (FIG. 44). The arm 4304 can be biased into a first position (shown in FIG. 43) by a spring 4302 coupled to the arm 4304. When in the first position, a first end 4304a of the arm 4304 is in contact with a first end 4306a of the base 4306 and a second end of the arm 4304b is spaced apart from a second end 4306b of the base 4306.

Figure 45A:
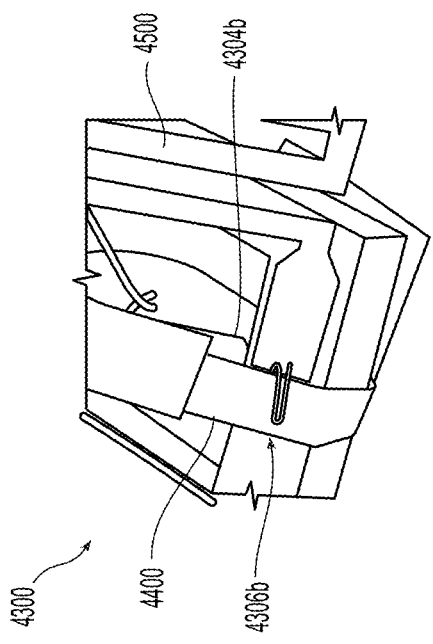
FIG. 45A is a perspective view of an actuator and a delivery channel before coupling the delivery channel to the pathway.
Figure 45B:
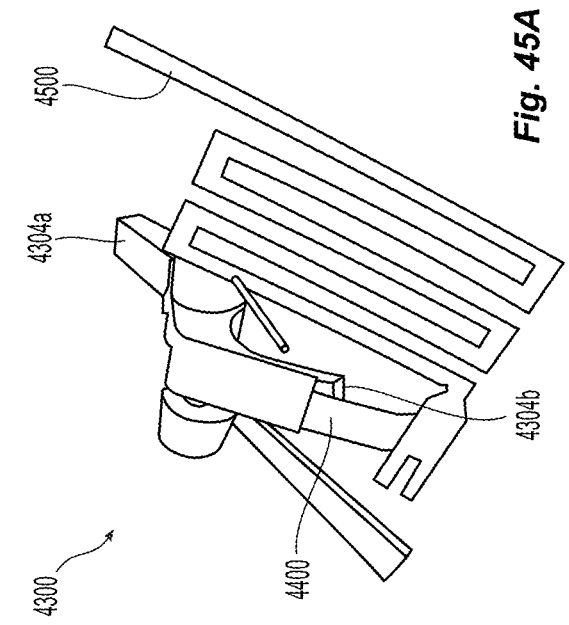
FIG. 45B is an enlarged view of an actuator showing a delivery channel coupled to the dissolvable pathway.

As shown in FIG. 44, a dissolvable pathway 4400 can be coupled to at least a portion of the arm 4304 and pulled toward the second end 4306b of the base such that the second end 4304b of the arm 4304 is forced downwardly towards the base 4306 (e.g., the second position). The dissolvable pathway 4400 can be secured to the base 4306, thereby securing the arm 4304 in the second position. Referring to FIGS. 45A and 45B, a portion of a delivery channel 4500 can be placed in fluid communication with the dissolvable pathway 4400 near the second end 4304b of the arm.

Figure 46:
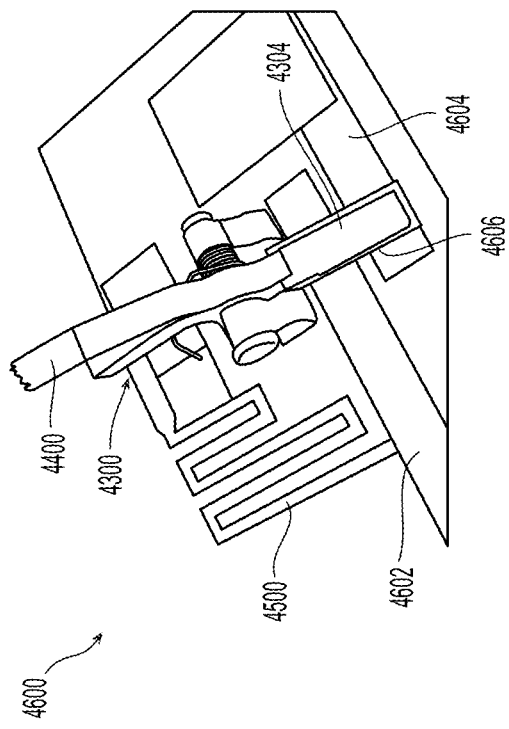
FIG. 46 is a top perspective view of a fluidic system incorporating an actuator configured in accordance with an embodiment of the present technology.

The actuator 4300 can be positioned within a fluidic system 4600 configured to activate the actuator 4300, as shown in FIG. 46. The delivery channel 4500 can be fluidly coupled to a first leg 4602, and a second leg 4604 can be positioned adjacent the first end 4304a of the arm 4304. In operation, an activating fluid can wick through the first leg 4602, into the delivery channel 4500, and eventually flow onto the dissolvable pathway 4400. The dissolvable pathway 4400 can be configured to dissolve and break upon exposure to a certain volume of fluid and/or certain fluids. When the dissolvable pathway 4400 breaks, the arm 4304 is released from the second position and the first end of the arm 4304a returns to the first position. In the first position, the second end of the arm 4304b contacts the first and second legs 4602, 4604. The second end of the arm 4304b can include a wick 4606 that contacts the first and second legs 4602, 4604, thereby fluidly coupling the first leg 4602 and the second leg 4604. As result, fluid from the first leg 4602 can transfer to the second leg 4604 (and other downstream portions of the system 4600).

Figure 47:
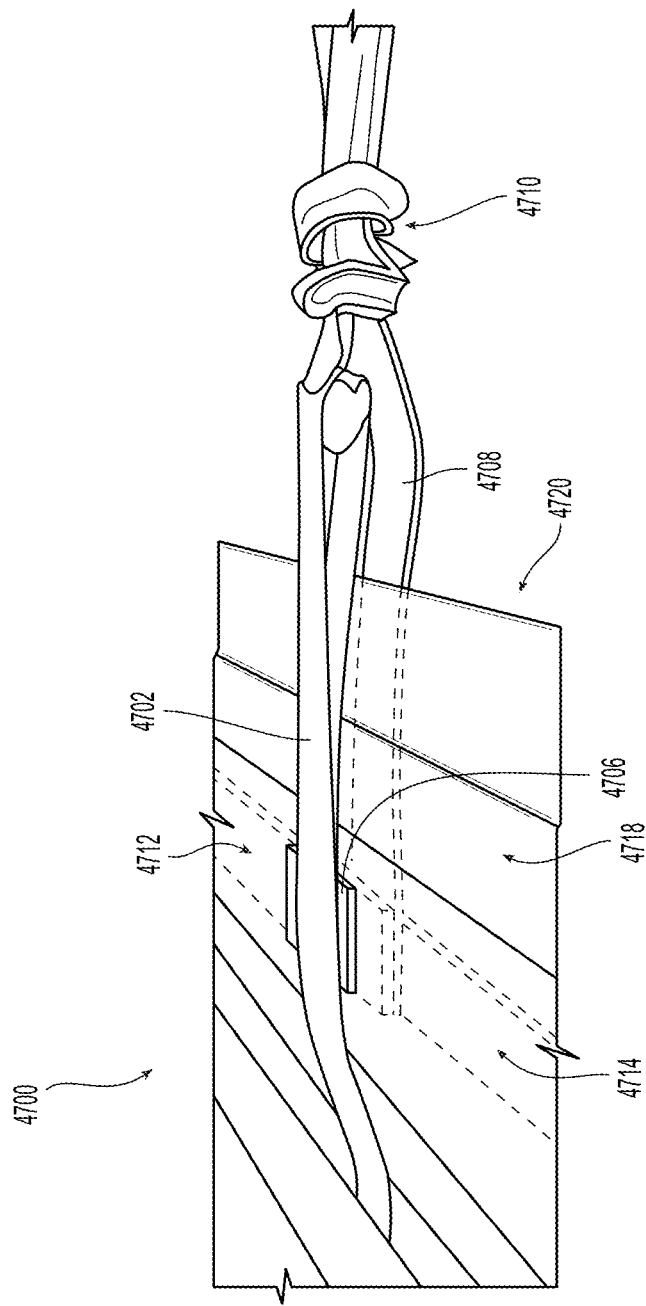
FIG. 47 is a side perspective view of an actuator configured in accordance with another embodiment of the present technology.
Figures 50A, 50B, 50C, 50D:
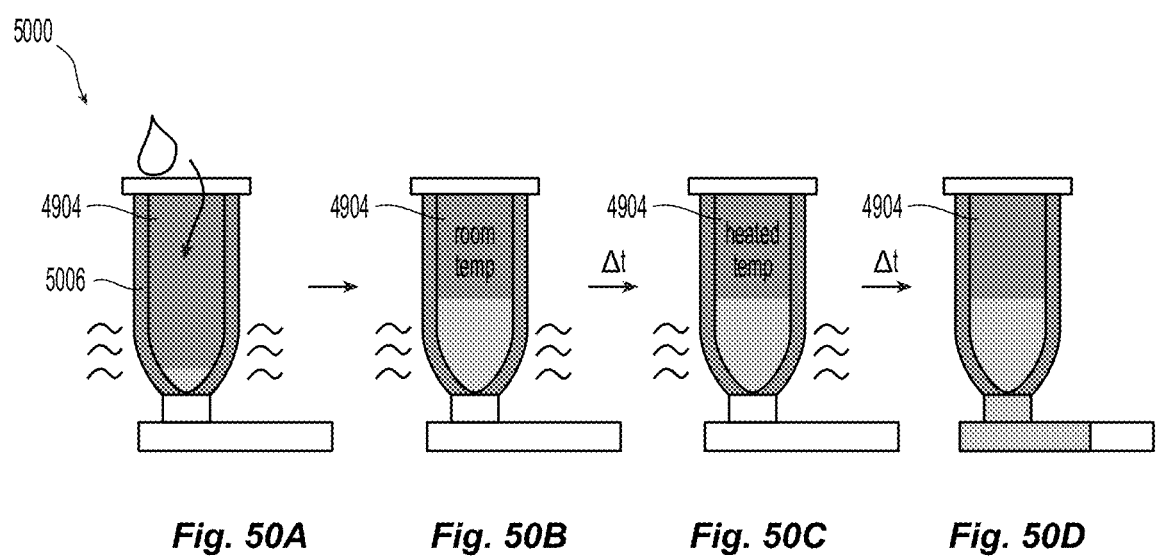
FIGS. 50A-50D are front views showing a molecular assay system including a chemical heat source configured in accordance with an embodiment of the present technology.

FIG. 47 is a side perspective view of another actuating assembly 4700 ("the assembly 4700") configured in accordance with the present technology. The assembly 4700 can include a low-friction tab 4708 (e.g., a PTFE film) that is positioned between two or more porous elements 4712, 4714. In some embodiments, a small piece of closed cell foam 4706 can be placed over the aligned portions of the porous elements 4712, 4714 and compressed to apply light pressure. In some embodiments, the assembly can include a cover 4718 (e.g., adhesive backed mylar, a PDMS mask, etc.) surrounding the porous elements 4712, 4714 to prevent or reduce unwanted evaporation. A portion of the tab 4708 can extend beyond the adhesive assembly 4720 and have two or more connecting portions (e.g., a first hole and a second hole) near its distal edge. A tensioning element 4710 (e.g., a rubberband, spring, etc.) can be coupled to the first hole, and a dissolvable pathway 4702 (e.g., dissolving cellulose paper) can be coupled to the second hole. The dissolving pathway 4702 can be secured to a fixed base (not shown). The tensioning element 4710 is then stretched and secured to a point on the fixed base, thereby adding tension to the dissolving pathway 4702. When the dissolving pathway 4702 becomes wet to a certain degree (e.g., by a delay strip (such as a delivery channel) or otherwise), the tension in the tensioning element 4710 can be transferred to the tab 4708. As the tab 4708 slides away from the aligned portions of the porous elements, the porous elements 4712, 4714 are allowed to contact each other and fluid may continue flowing from one element to another. One advantage of the system 4700 is that it provides for a low-profile delay valve. Furthermore, the system 4700 can benefit devices that require heating or insulation as it can be activated underneath insulation layers, thereby reducing heat loss.

V. SELECTED EMBODIMENTS OF DEVICES, SYSTEMS AND METHODS FOR CHEMICAL ASSAYS USING POROUS MEMBRANES a. Chemical Assays In chemical assays, enzymes are used to partially digest biological samples (e.g., a tissue sample, a cell sample, a DNA sample, etc.) before further analysis. For example, bacteriolytic enzymes are used to digest or break down bacteria. Achromopeptidase ("ACP") is an extract that contains several such bacteriolytic enzymes. ACP breaks down linkages in peptidoglycan cell walls and is especially effective at lysing gram positive organisms. In laboratory procedures, enzymes, such as ACP, are often times deactivated or otherwise separated from DNA and other analytes prior to further chemical processing and analysis. In particular, in nucleic acid amplification assays, bacteriolytic enzymes are typically separated from sample nucleic acid or deactivated, in part to prevent degradation of amplification enzymes. Deactivation is normally done by heat treatment.

FIG. 48A is a front schematic view of a system 4800 for performing a molecular assay configured in accordance with the present technology. The system 4800 can include a vessel 4804, a control element 4808 and a porous element 4802 (e.g., a pathway, wick, leg, etc.). The control element 4808 can be positioned between the vessel 4804 and the porous element 4802 and configured to selectively release the contents of the vessel 4804 into the porous element 4802. The control element 4808 can include, for example, a dissolvable barrier (e.g., sugar, salt, gel, etc.), a phase change material (e.g., a wax that melts after having been in contact with the heated contents of the vessel), a mechanical valve, or other suitable control structures.

FIGS. 48A-48D illustrate a method for performing a molecular assay using the system 4800. As shown in FIG. 48A, a user (or automated system) can deliver a biological sample B to a vessel 4804 containing one or more enzymes E (alternatively, the enzymes E can be delivered to a vessel containing a biological sample B). The enzymes E interact with and at least partially digest the sample B, thereby forming a lysis solution L. To prevent the enzymes E from performing additional, unwanted lysis on the sample B, the enzymes E can be deactivated by heating the lysis solution L to a deactivation temperature. As shown in FIG. 48C, the system 4800 can further include a heat source (not shown) configured to heat H the vessel 4804 at a predetermined temperature for a predetermined amount of time that depends on the volume and composition of the lysis solution. In some embodiments, for example, the vessel 4804 can be heated to 95° C. for 10 minutes. In some embodiments, the heat source can be an electrical heat source, and in other embodiments, the heat source can be a chemical heat source, as described in greater detail below with reference to FIGS. 50A-50D.

As shown in FIG. 48D, upon a trigger event, the control element 4808 fluidly connects the vessel 4804 and the porous element 4802, thereby releasing the lysis solution L from the vessel 4804 into the porous element 4802. In one embodiment, the control element 4808 is a dissolvable barrier configured to dissolve after exposure to a set volume of fluid. For example, the height, width, length and/or material composition of the dissolvable barrier can be selected to dissolve in a particular amount of time. Several examples of such dissolvable barriers are discussed above with reference to FIGS. 36-42. In the present system 4800, the time it takes for the barrier to dissolve can be coordinated with the desired heating time of the lysis solution L to deactivate the enzymes E. For example, if the desired enzymatic lysis takes five minutes, and the deactivation heating can take ten minutes, the dissolvable barrier can be designed to dissolve (after exposure to the lysis solution L) after fifteen minutes.

FIGS. 49A-49C illustrate a method for separating the enzymes E (shown individually for ease of description) from the lysis solution L using the system 4800. The porous element 4802 can include one or more capture agents (not shown) capable of immobilizing the enzymes E. When the control element 4808 releases the lysis solution L from the vessel 4804 to the porous element 4802, the enzymes E can become substantially immobilized to a portion of the porous element 4802 as the rest of the contents of the lysis solution L are wicked through the porous element 4802. Similarly, in some embodiments the porous element 4802 can include nucleic acid binding particles (not shown). As such, when the vessel 4804 comes into fluid contact with the porous element 4802, the enzymes E wick into the porous element 4802 while the nucleic acids (not shown) remain bound to the nucleic acid binding particles. The nucleic acid can be removed from the nucleic acid binding particles through the application of additional fluids to the porous element 4802. For example, the porous element 4802 can be impregnated with a nucleic acid binding composition, such as chitosan. Chitosan is capable of reversibly binding nucleic acids in a pH dependent manner. Additionally, the porous element 4802 can include a detection zone (not shown) capable of selectively binding and visualizing nucleic acids. In certain embodiments of the present disclosure, the porous element 4802 comprises a detection zone capable of selectively binding and visualizing peptides.

The vessel 4804, control element 4808 and/or porous element 4802 can include additional reagents and/or materials for chemical reactions, such as nucleic acid amplification, immunoassays, nucleic acid detection, and the like. Such reagents can be disposed within the system upstream of the vessel, downstream of the vessel, and/or impregnated into the porous element 4802. For example, the vessel 4804 can include nucleic acid amplification reagents that can be used in a nucleic acid amplification reaction once the heat source deactivates the enzymes E. Such nucleic acid amplification reactions include isothermal nucleic acid amplification reactions. In some embodiments, the vessel 4804, control element 4808 and/or porous element 4802 can include chemicals configured to deactivate the enzymes E (e.g., 1,10-Phenantrholine, disulfide cleavage, etc.).

FIGS. 50A-50D are front views showing a self-regulating system 5000 performing a molecular assay configured in accordance with another embodiment of the present technology. The system 5000 can be generally similar to the system 4800 described with reference to FIGS. 48A-49C except as described below. In the illustrated embodiment, the system includes a chemical heat source 5006 that surrounds the vessel 4904. The system 5000 is configured to self-regulate timing onset of heat deactivation. For example, the chemical heat source 5006 can be activated and/or powered by a chemical reaction between two or more reagents, such as MgFe and saline. The chemical heat source 5006 can include a reacting member surrounding at least a portion of the vessel 4904. The reacting member can be coupled to a timed delivery channel (not shown) (for example, discussed above with reference to FIGS. 29-31) and can be activated when an activating solution (e.g., a saline solution) flows through the delivery channel and contacts the reacting member.

In some embodiments, the heat source can comprise a phase change material. Phase change materials are capable of maintaining the vessel 4804 and/or lysis solution L at or near the temperature of the phase change. For example, where a phase change material is that which changes from a solid to a liquid, the phase change material will stay substantially at the melting temperature despite additional input of energy. Through appropriate selection of the phase change material, the system 4800 can include a heat source that maintains the vessel 4804 at the appropriate reaction temperature despite the additional application of heat from other sources, such as from a chemical reaction. In some embodiments, the heat source can be configured to maintain the contents of the vessel between 80 and 110 degrees Celsius. In a particular embodiment, the heat source is configured to maintain the contents of the vessel 4804 at approximately 100 degrees Celsius.

b. Concentration of Fluid Contents

Membrane based POC diagnostic devices often lack the ability to quickly and effectively concentrate substances/analytes/solutes/cells of interest. For example, volumes of fluids used for sample preparation steps in POC diagnostic devices (e.g., swab transfer, lysis, etc.) are generally large. However, the concentration of analytes is low, often requiring amplification or other means to reach appreciable detection sensitivities. Amplification, however, can be complicated, thus limiting many downstream applications.

Figure 51:
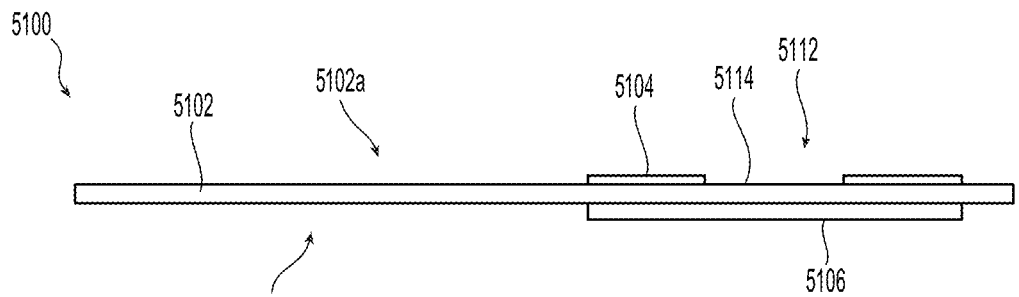
FIGS. 51-54 are side views showing various systems for selective evaporation configured in accordance with an embodiment of the present technology.

FIGS. 51-54 are cross-sectional side views of various systems for selectively evaporating fluid contents configured in accordance with the present technology. FIG. 51 shows a system 5100 that includes a porous element 5102, a mask 5014, and a heat source 5106. The porous element 5102 can have a first side 5102a and a second side 5102b. The mask 5104 can be positioned adjacent the first side 5102a and the heat source 5106 can be positioned adjacent the second side 5102b opposite the mask 5104. The mask 5104 can include an opening 5112 aligned with the heat source 5106 such that a portion 5114 of the porous element 5102 is exposed at the first side 5102a. When the porous element 5102 is heated via the heat source 5106, fluid is evaporated through the opening 5112 in the mask 5104, thereby concentrating the analytes (e.g., proteins, nucleic acids, etc.) present in the fluid within the exposed portion 5114 of the porous element 5102. For example, the analyte may be concentrated by a factor of about 100.

The mask 5104 can include one or more materials suitable for reducing evaporation, such as polydimethylsiloxane (PDMS), mylar, one or more plastics, a metalized film and the like. The mask 5104 and/or opening 5112 can have any suitable size or shape (e.g., polygon, circle, star-shaped, etc.) and the mask 5104 and/or opening 5112 can have the same shape or different shapes. In some embodiments, the system 5100 can include more than one mask positioned at different locations along the porous element 5102.

In some cases, the analytes may become further concentrated within a region smaller than the area of the exposed portion 5114 due to fluid flow driven by evaporation. Such a smaller region may form, for example, in the middle of the exposed portion 5114. Following concentration, the analytes can be drawn into other regions of the system 5100 or can be recovered using additional porous membranes placed in contact with the porous element 5102. In some embodiments, multiple materials with different properties may be stacked one on top of another (with or without masks) allowing concentration, transfer and recovery of the analyte concentrate.

Figure 52:
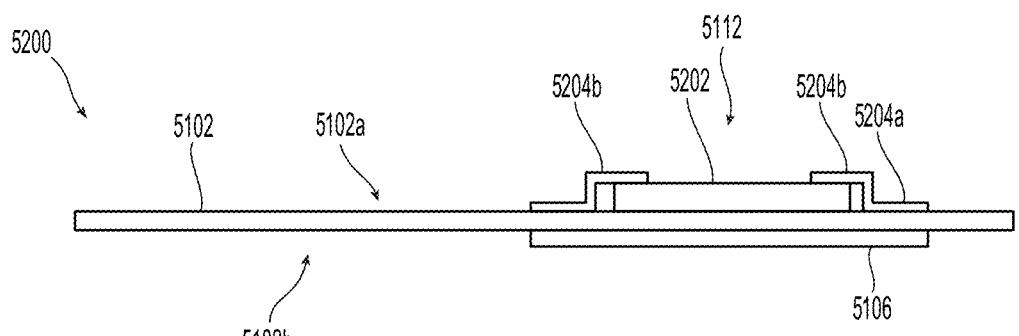
Figure 53:
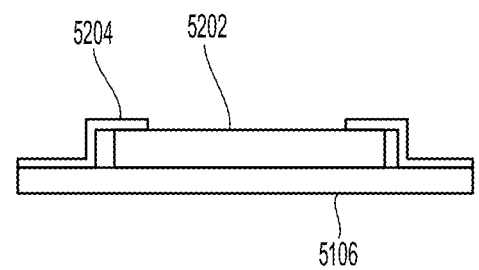

FIG. 52 shows a cross-sectional side view of a system 5200 including a second porous element 5202 (e.g., a pad) configured in accordance with another embodiment of the present technology. The second porous element 5202 can be positioned at the first side 5102a of the first porous element 5102 opposite the heat source 5106. The mask 5204 can have a first portion 5204a in contact with the first porous element 5102 and a second portion 5204b in contact with the second porous element 5202. The first portion 5204a and the second portion 5204b can be in different planes, as shown in FIG. 52. In some embodiments, the mask 5204 only contacts the first porous element 5102 or the second porous element 5202. The second porous element 5202 can be positioned on the first porous element 5102 aligned with the opening 5212 in the mask 5204. Such positioning can enhance recovery of the concentrated analyte via removal of the second porous element 5202 or by causing the second porous element 5202 to contact a different wicking material to draw out concentrated analyte.

Figure 54:
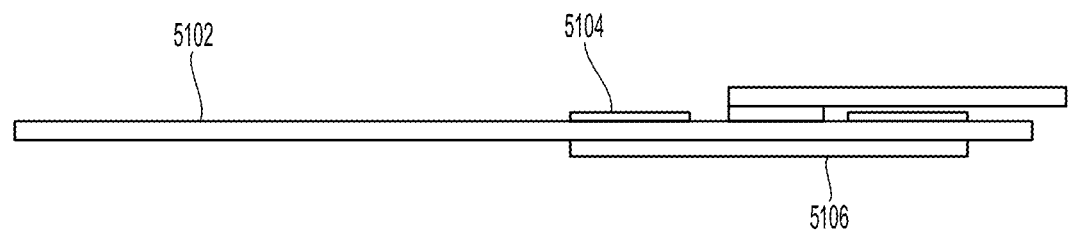

Recovery of the analyte can also be achieved by removing the exposed portion 5114 of the porous element 5102. Removal methods include punching out a portion of the exposed region, physically removing a collection material (such as a second porous element 5202), wicking the concentrated analyte into a different material (e.g., by contacting a wicking material with a portion of the evaporation region) and other suitable methods. In embodiments utilizing wicking the concentrated analyte into a different material, the fluid required to carry the analyte can be remaining source fluid, additional fluid added to the source material, or additional fluid wicked through a portion of the collection material (e.g., transverse flow from bottom to top). As shown in FIG. 54, additional porous elements can be fluidly coupled to the exposed portion 5114 and used to transfer the concentrated analyte for further analysis.

Removal procedures can be done manually or by switching mechanisms embedded in the device. For example, additional fluid sources can be fluidly contacted using paper-based control devices (see FIGS. 22-47), or a collection material can be physically disconnected from the source material and connected to a different wicking material using a mechanical switch (see FIGS. 22-47).

In any of the above described embodiments, the heat source can be an electrical heat source or a chemical heat source. In some embodiments, the system does not include any heat source. Evaporation can occur at ambient humidity, or a desiccant can be used to create reproducible (and larger) evaporation rates. The evaporation process may be carried to complete dryness or the porous element can remain wet at the end of the concentration step. Evaporation can be controlled and is dependent on a number of parameters such as time of evaporation, temperature, surface area of evaporation etc. The heating may be localized (mask region) or may cover a larger area spanning the source fluid.

It is believed that the spatial pattern of concentration can be manipulated by the properties of the material(s) used. For example, a thin material with high fluidic resistance (e.g., nitrocellulose) will tend to further concentrate analyte in a region smaller than the exposed portion due to convective flow towards the middle of the exposed portion. In contrast, a thick material with low fluidic resistance (e.g., thick cellulose) will show less effect from convective flow and will have a more uniform concentration. Properties of combined materials can also be useful for manipulating the concentration effect or the spatial concentration pattern (e.g., using a cellulose source material with a glass fiber collection material, using a nitrocellulose source material with a cellulose collection material, etc).

Since concentration acts on all constituents of the fluid, it may be important in some scenarios to strip the fluid of undesired components (e.g., salts or proteins) first if the analyte of interest are nucleotides. For example, if the desired analytes for detection are proteins, a column of silica may first be used to remove the nucleotides by binding before concentration of proteins is undertaken. In another embodiment, it may be possible to start with a dilute solution of reagents (e.g. lysis reagents) and concentrating to reach a desired concentration of those reagents that are necessary for one spot lysis. For example, the sample source (as a fluid reservoir, membrane, or source pad) can contain lysis components (e.g., surfactant, chaotropic salts) at low concentrations such that the concentration step results in lysis components at the desired concentration, and the concentration zone can be a material that allows capture of a selected component. A specific example would use chaotropic salts (e.g., guanidinium hydrochloride, guanidinium isothiocyanate; and other components as needed) at low concentration concentrated onto a solid phase extraction material (e.g., silica) to capture nucleic acids; non-analyte components (e.g., salts, proteins, lysis components) could be washed away, followed by elution (release) of the nucleic acids.

Figure 55:
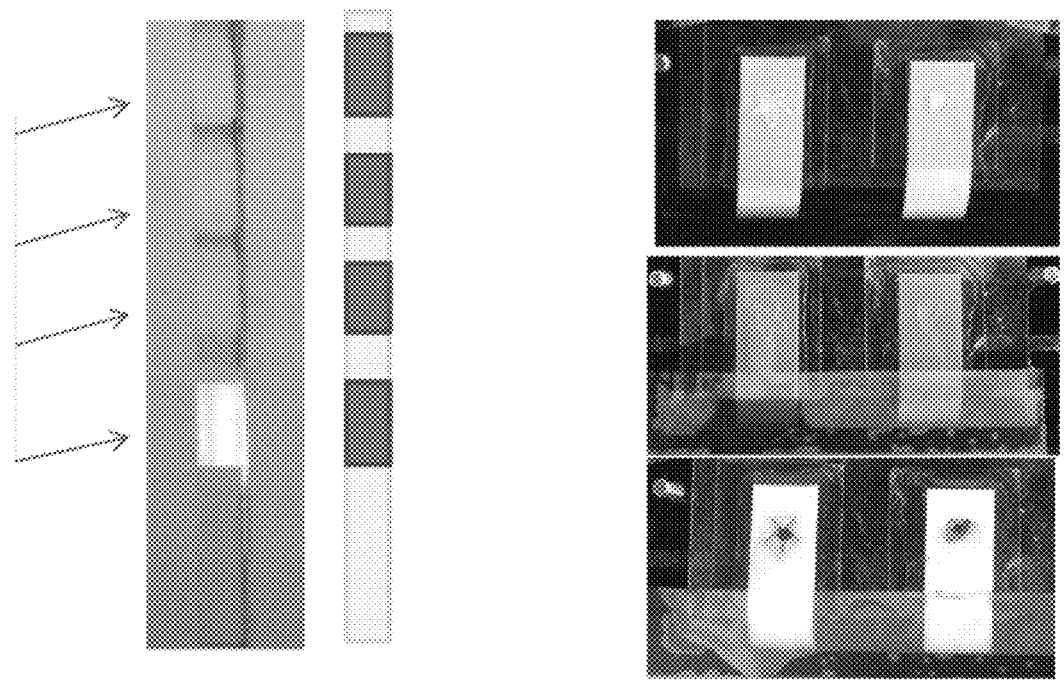
FIG. 55 is a top view showing a concentration pattern based on mask size.

In some embodiments, the masks may be placed over membranes and various labels, dyes may be patterned according to the shape of the mask. Such a low cost approach may allow for rehydration patterns that are different from what is currently obtained using standard printing achieved using expensive piezo-array printers and stripers. For example, as shown in FIG. 55, by varying the distance between the masks, it is possible to draw the dye/label/reagents into defined regions (e.g., using slow evaporation for a few hours/overnight). As shown in FIG. 55, the patterns of concentrated analyte follow the shape and size of the mask employed on the porous element. In other embodiments, more complicated patterns, such as pentagons and quadrants, can be used. Such patterns can be used to pattern materials that affect flow, such as sugars that can be used to delay fluid wicking or change flow patterns.

Figure 56:
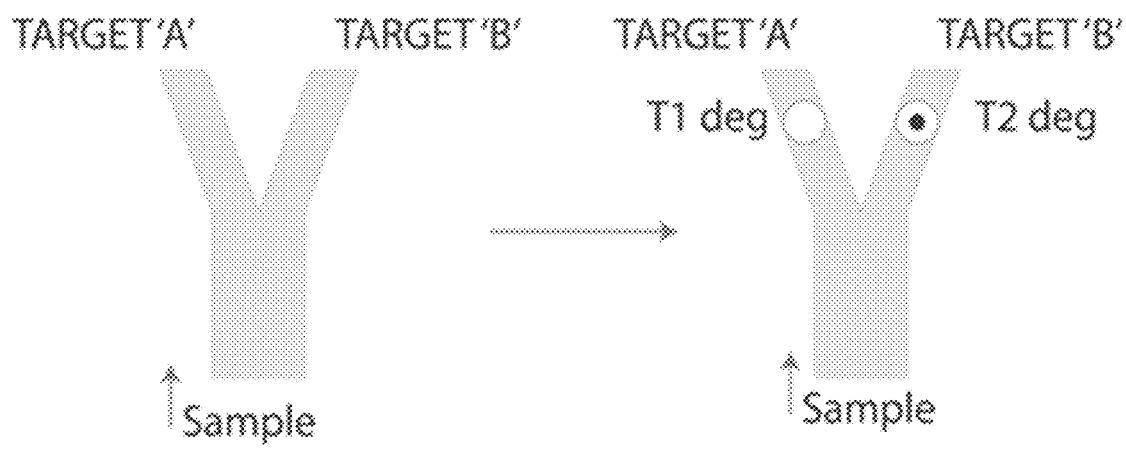
FIG. 56 illustrates top views of a device for preferential flow and concentration configured in accordance with an embodiment of the present technology.

FIG. 56 illustrates top views of a device for concentrating an analyte configured in accordance with the present technology. As shown in FIG. 56, a fixed volume of sample/fluid can be delivered into a pathway having multiple legs, each coupled to a separate heat source (not shown). By applying different temperatures to each leg, different evaporation rates are induced in the legs. As such, different flow rates are induced in each leg and the leg at the higher temperature will have the higher flow rate, and thus create a more concentrated analyte (in the illustrated embodiment, the second leg). Alternatively, different evaporation rates can be achieved using a single temperature (heated or room temperature) but changing the size of the evaporation region (e.g., the exposed region). This separation and subsequent concentration (if desired) is currently not achievable using existing methods. For example, the sample may include Target A, a high abundance gene, and Target B, a low abundance gene that requires a much larger proportion of the sample. The device can allow preferential flow of the sample/fluid into the second leg by controlling parameters such as the temperature and the evaporation rate.

VI. SELECTED EMBODIMENTS OF DETECTION DEVICES AND ASSOCIATED SYSTEMS AND METHODS

Figure 57:
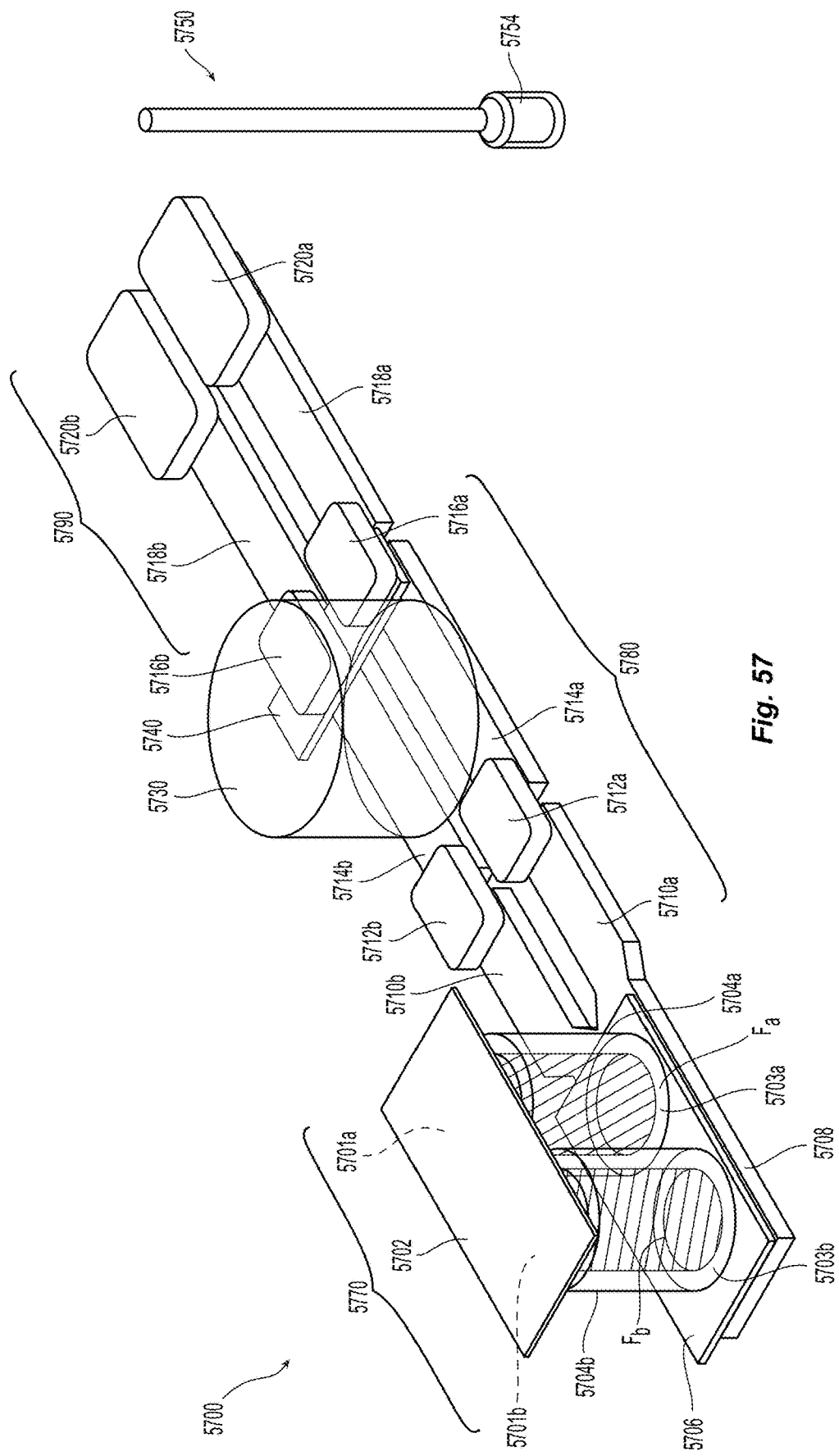
FIGS. 57-68 are perspective views of a detection device configured in accordance with an embodiment of the present technology.

FIG. 57 is a perspective view of a detection system 5700 configured in accordance with the present technology. The system 5700 can include a loading zone 5770, an amplification zone 5780, and a detection zone 5790. The loading zone 5770 can include a first barrier 5706, a first fluid source 5704a, and a second fluid source 5704b. The first and second fluid sources 5704a, 5704b can be ideal fluid sources and can be positioned such that the first fluid source 5704a is positioned between the second fluid source 5704b and the amplification zone 5780. In some embodiments, the first fluid source 5704a can contain a first fluid $F_a$ (e.g., a lysis buffer and a denaturation heater, etc.) and the second fluid source 5704b can contain a second fluid $F_b$ (e.g., a detection buffer). The first and second fluid sources 5704a, 5704b can have first and second inlets 5701a, 5701b, respectively, covered by a protective film 5702 and first and second outlets 5703a, 5703b opposite the inlets 5701a, 5701b. The outlets 5703a, 5703b can be positioned adjacent an input pathway 5708 in contact with a barrier 5706 positioned between the first pathway 5708 and the outlets 5703a, 5703b.

Figure 69:
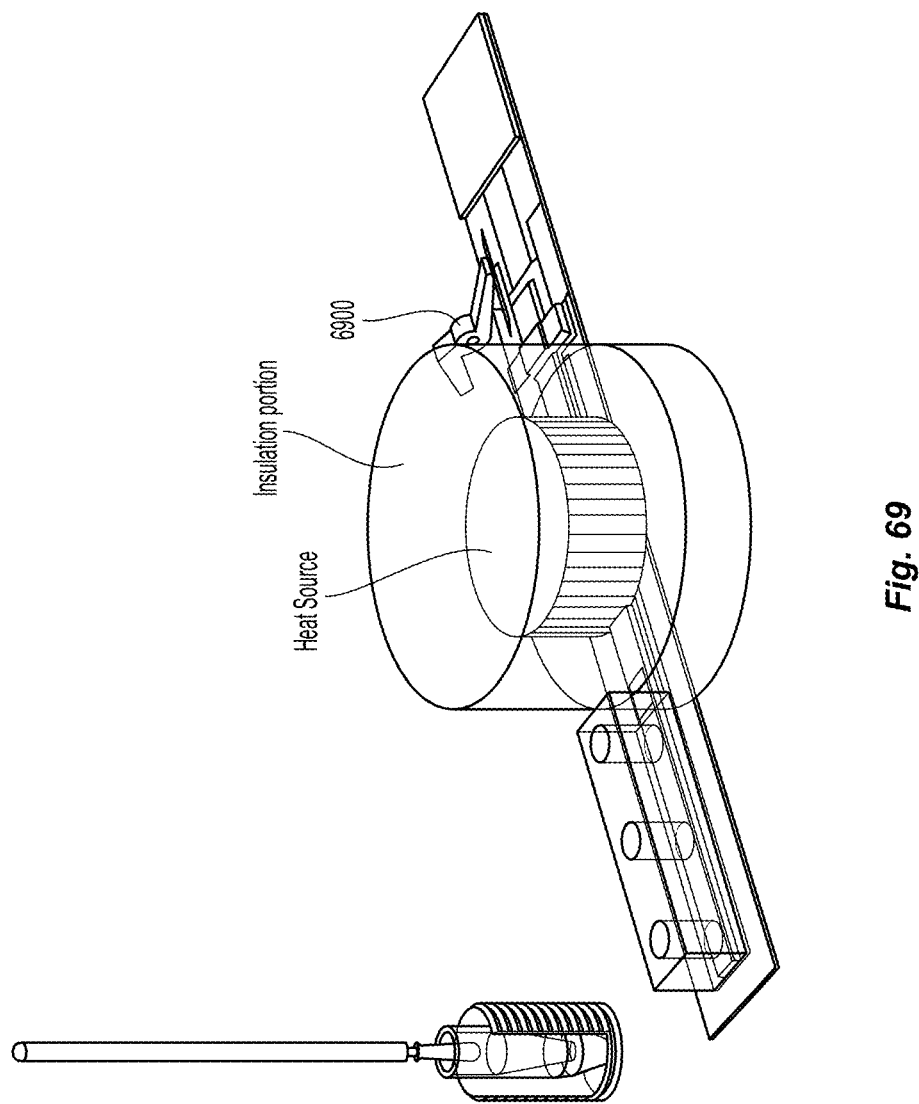
FIG. 69 is a perspective view of a detection device configured in accordance with another embodiment of the present technology.

The input pathway 5708 can branch into a first leg 5710a and a second leg 5710b. A distal portion of each of the first and second legs 5710a, 5710b can individually be fluidly coupled to first and second amplification pads 5712a, 5712b. The amplification pads 5712a, 5712b can include one or more dry (or wet) amplification reagents, such as nicking enzymes, polymerases, probes, primers, and other components utilized in isothermal amplification reactions. In some embodiments, an optional valve or barrier (not shown) can be positioned between the first and second legs 5710a, 5710b and the first and second amplification pads 5712a, 5712b, respectively. Although only two legs are shown, the system 5700 can include one leg or more than two legs. A distal portion of each of the first and second amplification pads 5712a, 5712b can individually be coupled to first and second heating legs 5714a, 5714b. A heat source 5730 can be positioned on or adjacent the heating legs 5714a, 5714b. The heat source 5730 can have an insulation portion (not shown for ease of illustration) (see FIGS. 69 and 70). A distal portion of each of the first and second heating legs 5714a, 5714b can be coupled to first and second detection pads 5716a, 5716b, and a barrier 5740 can be positioned between the distal portions of the first and second heating legs 5714a, 5714b and the first and second detection pads 5716a, 5716b. The detection pads 5716a, 5716b can include one or more dry (or wet) detection agents (e.g., capture beads). A distal portion of each of the first and second detection pads 5716a, 5716b can be coupled to first and second detection legs 5718a, 5718b, and a distal portion of each of the first and second detection legs 5718a, 5718b can be coupled to first and second waste pads 5720a, 5720b. In some embodiments, the first and second detection legs 5718a, 5718b can additionally or alternatively be coupled to additional downstream paper networks.

Figure 58:
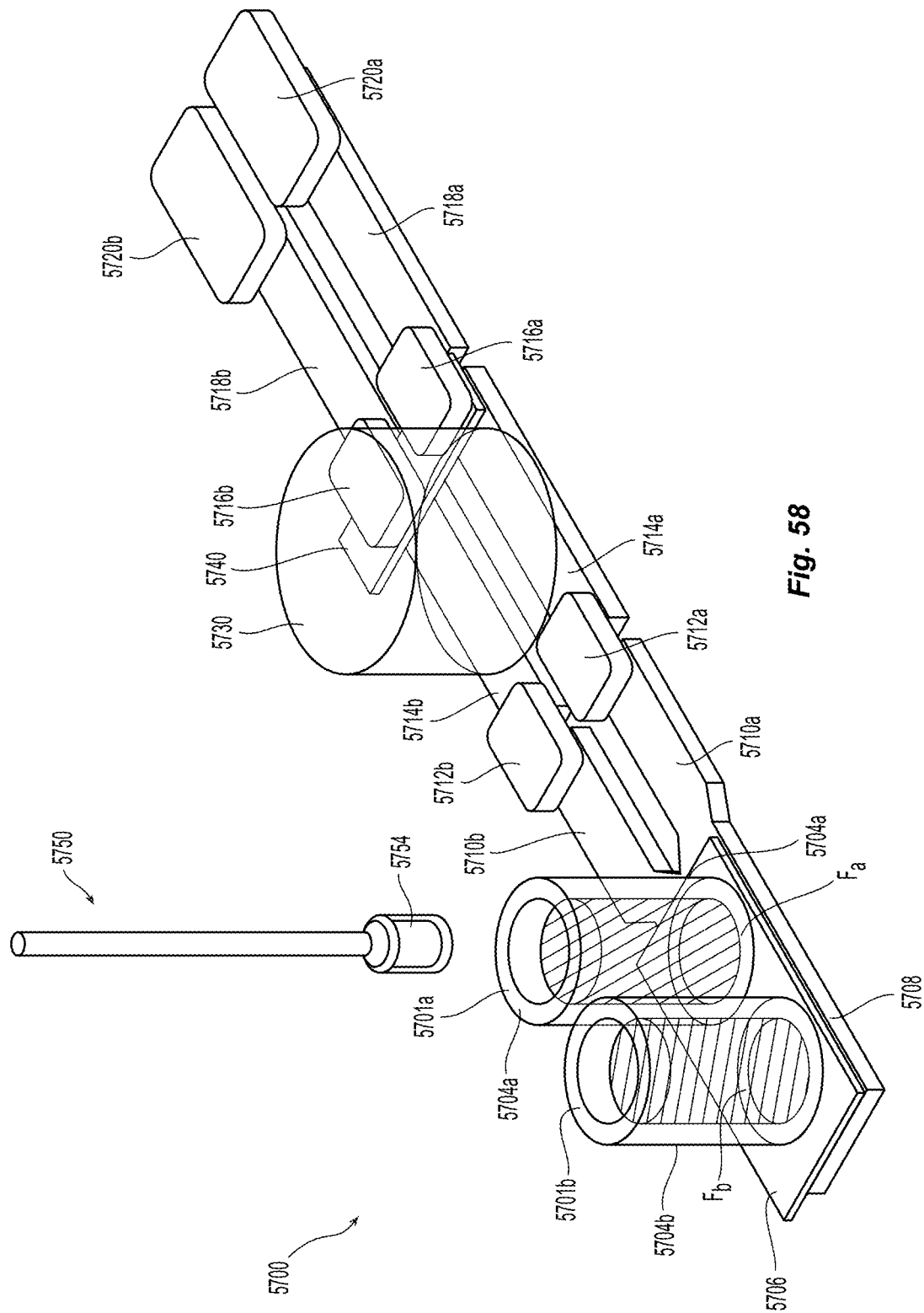
Figure 59:
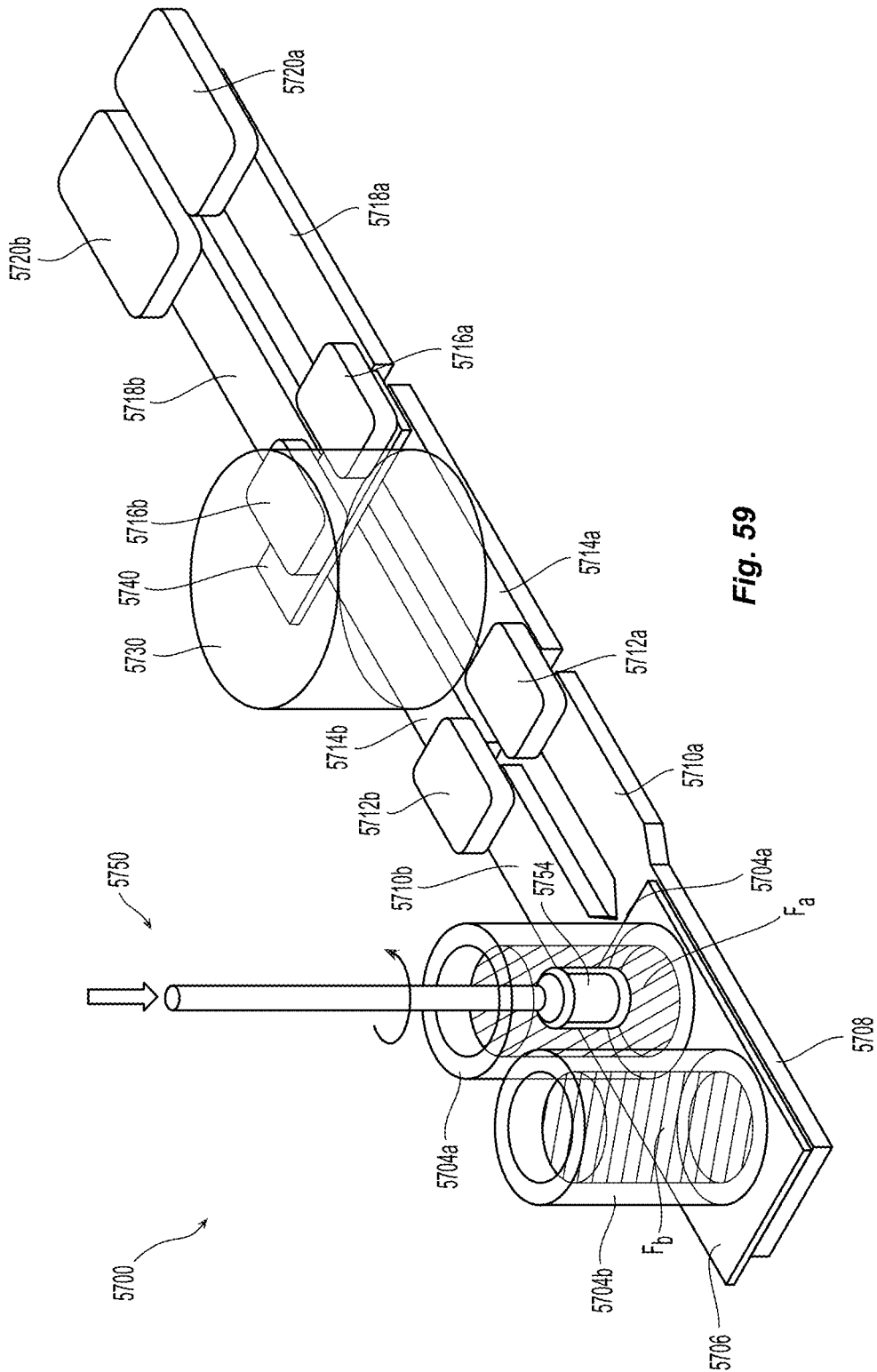

FIGS. 57-68 illustrate the system 5700 throughout various stages of the amplification and detection. As shown in FIGS. 58 and 59, the protective film 5702 covering the fluid source inlets can be removed, thus exposing the contents of the first and second fluid sources 5704a, 5704b. For example, in some embodiments, the system 5700 can be placed within a housing 7002 (see FIG. 70) and a moveable cap portion 7004 (see FIG. 70) of the housing 7002 can be opened to remove the film. In other embodiments, the film can be removed by the user or by other methods known in the art.

As shown in FIGS. 58 and 59, a sample-carrying portion 5754 of a swab 5750 can be placed within the first fluid source 5704a in contact with the first fluid $F_a$. Once inserted into the fluid source 5704a, the sample carrying portion 5754 can be can twirled (by the user or automatically) to increase surface area contact between the sample-carrying portion 5754 and first fluid $F_a$. Once sufficiently mixed, the user can close the housing cap 7004 (see FIG. 70).

Figure 60:
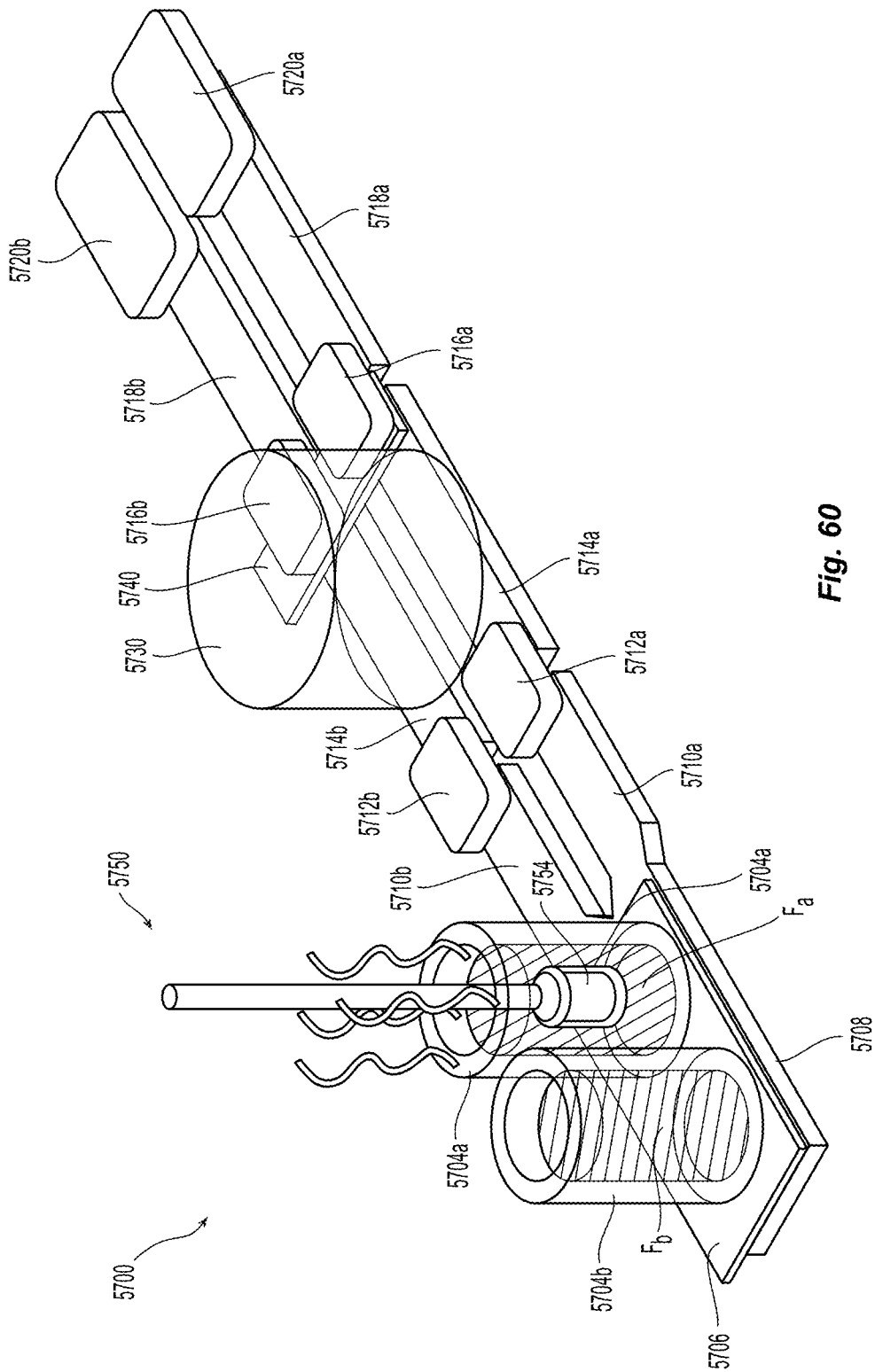
Figure 61:
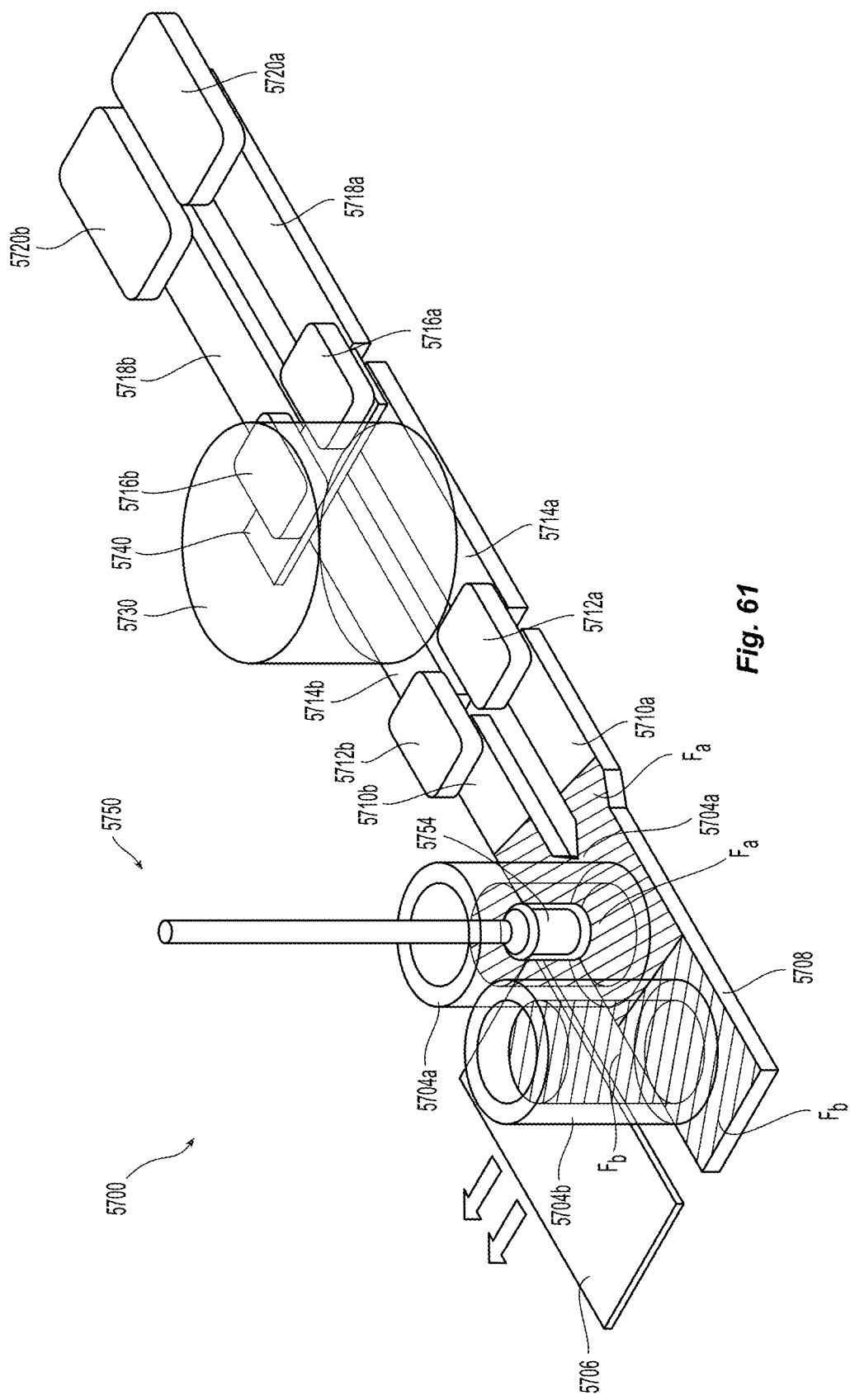
Figure 62:
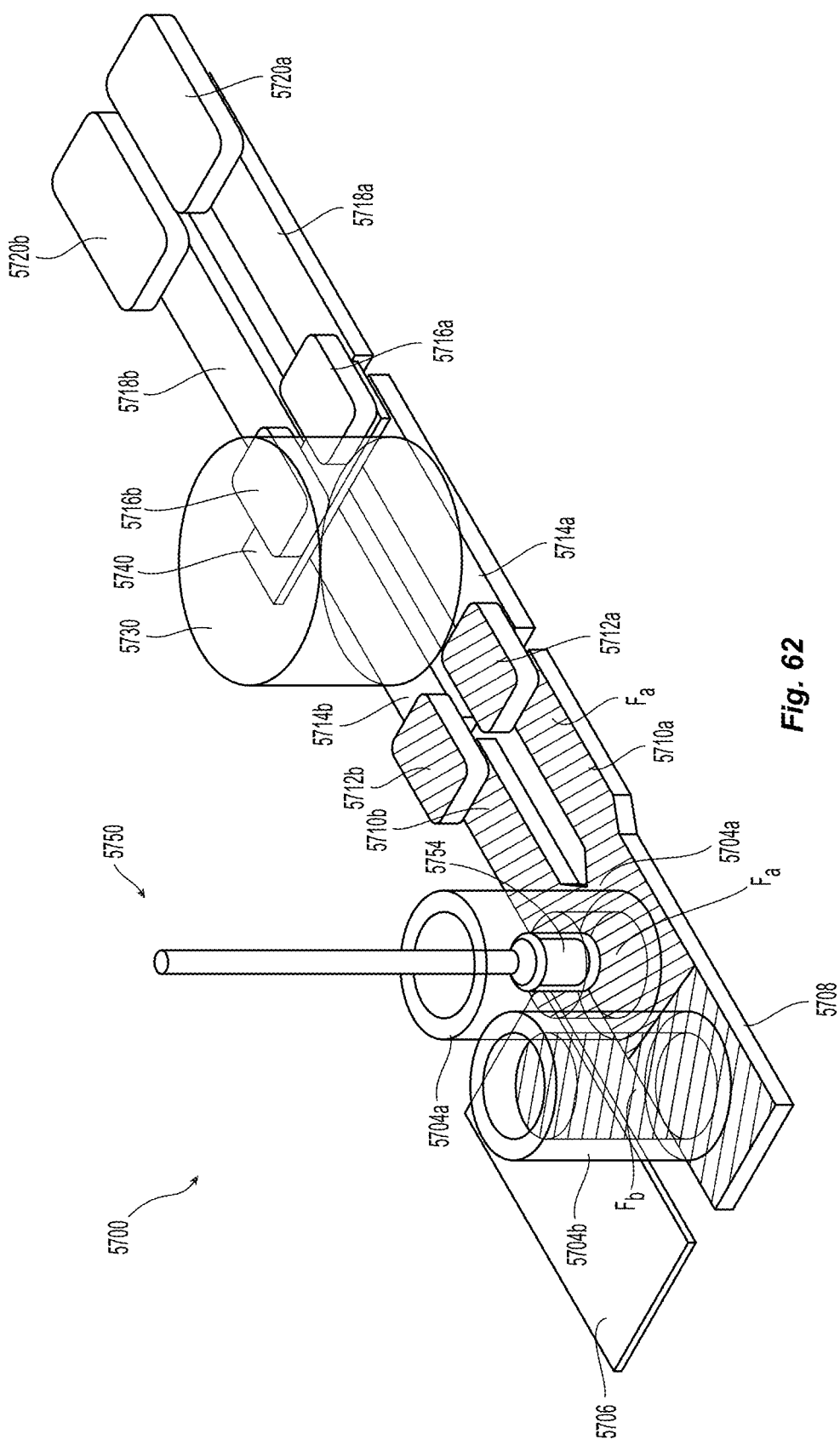

As shown in FIG. 60, the first fluid source 5704a can be heated (via a heat source (not shown) (e.g., to 100 degrees Celsius) to inactivate the enzymes in the first fluid and, for example, fragment any DNA in the sample. Next, the first barrier 5706 can be pulled outwardly (away from the fluid sources) to simultaneously fluidly connect the first and second fluid sources 5704a, 5704b to the first pathway 5708 (FIG. 61). The first fluid progresses through the first pathway and is split between the first and second legs 5710a, 5710b. The fluid then flow through the first leg and the second leg to the first and second amplification reagent pads 5712a, 5712b, respectively. Once in contact with the amplification pads 5712a, 5712b, the first fluid (e.g., the lysis solution) mixes with the amplification reagents.

Figure 16:
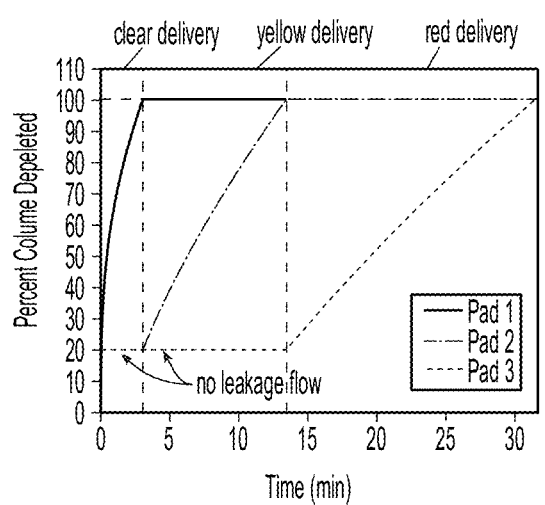
FIG. 16 is a graph showing the percentage of fluid volume depleted versus time for the sequential delivery device shown in FIG. 14.
Figure 63:
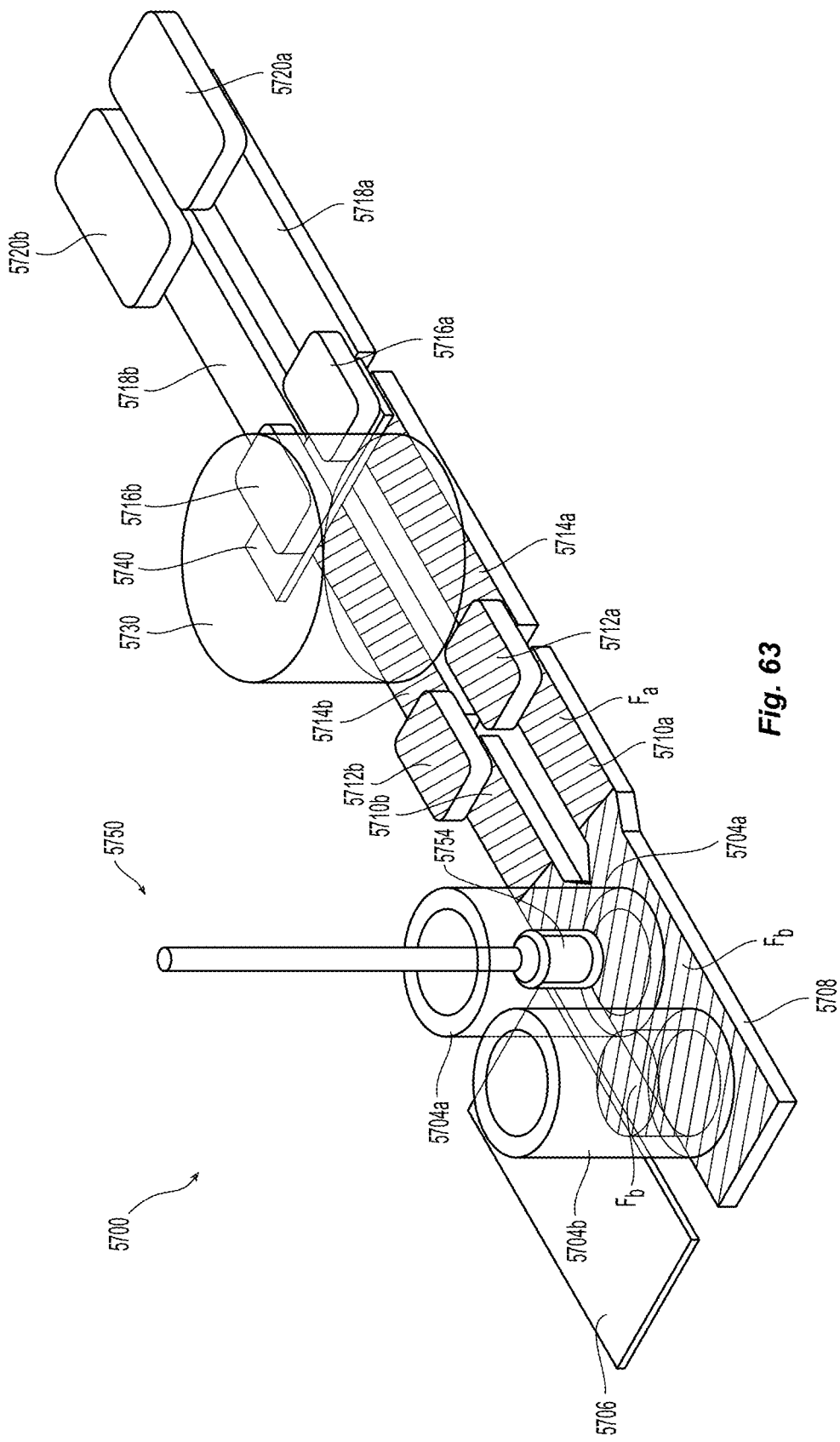
Figure 64:
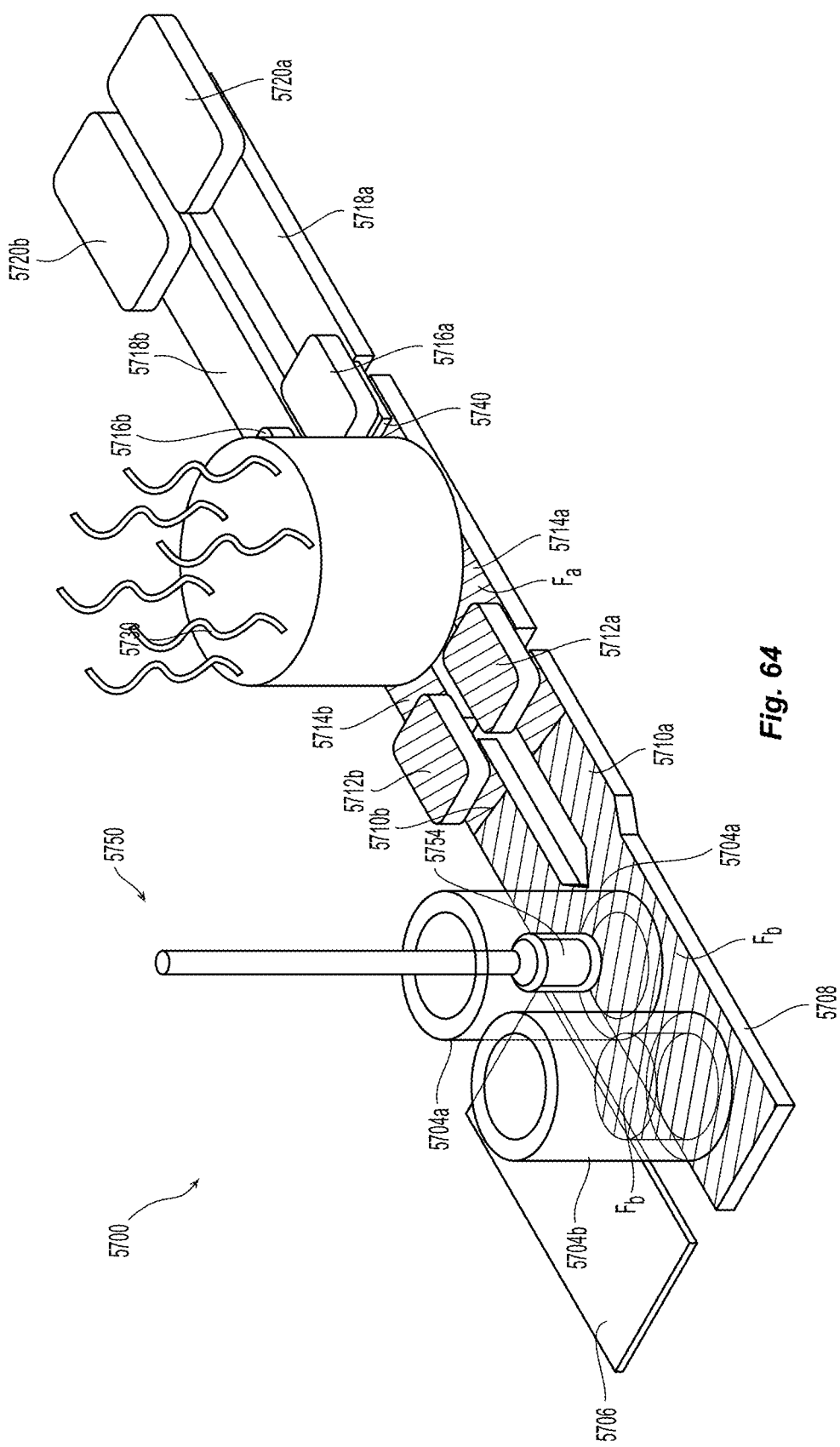
Figure 65:
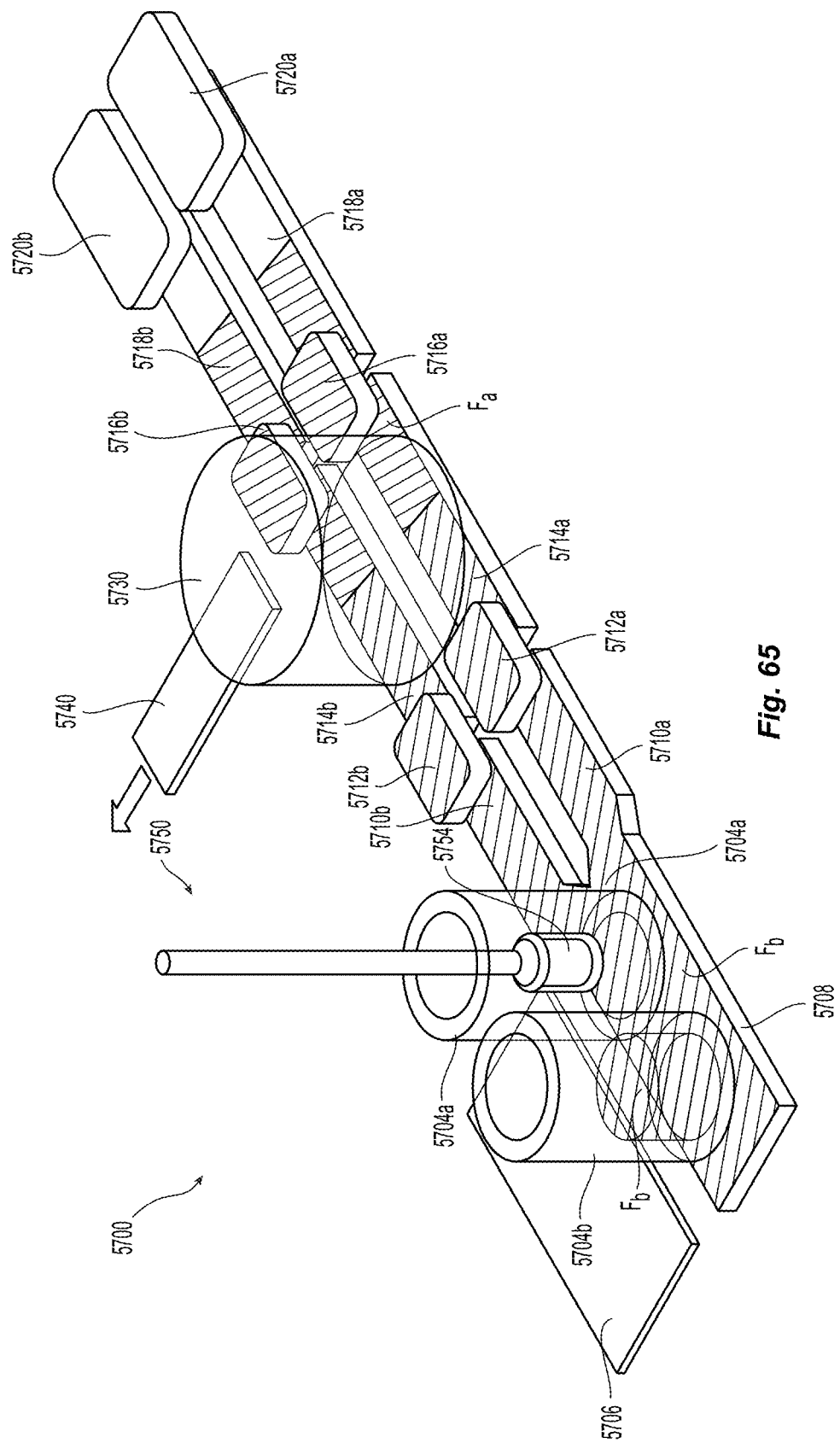

FIG. 63 shows the wicking-driven sequential delivery (discussed above with reference to FIGS. 14-16) pushes the first fluid into the heating legs 5714a, 5714b and under the heat source 5730. The heat source 5730 can then be activated, as shown in FIG. 64, to aid in the isothermal amplification (e.g., iSDA incubation, 49.5 degrees Celsius for 20 minutes.). Once the amplification is complete (e.g., after a certain time at a certain temperature), a barrier 5740 can be removed to fluidly connect the heating legs 5714a, 5714b with the detection pads 5716a, 5716b (FIG. 65). In some embodiments, the system 5700 can include a fluidic actuator 6900 (discussed above with reference to FIGS. 43-47) (see FIGS. 69 and 70) in place of or in addition to the removable barrier. The fluidic actuator 6900 can be coupled to a timing device/delivery channel 7006 (see FIG. 70) that delays the fluid coupling of the heating legs 5714a, 5714b to the detection pads 5716a, 5716b an amount of time sufficient for the isothermal amplification to occur on the heating legs 5714a, 5714b.

Figure 66:
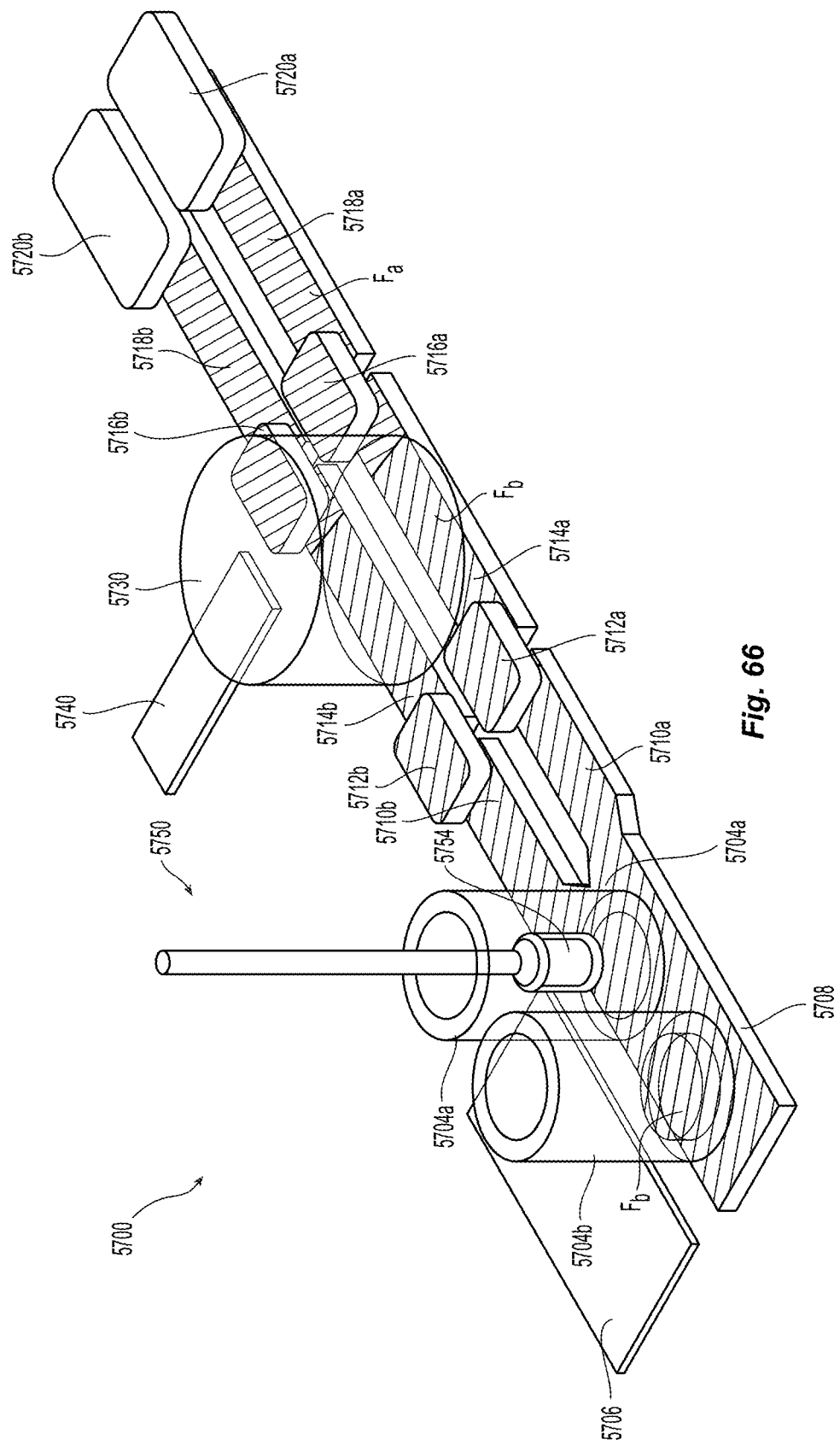
Figure 67:
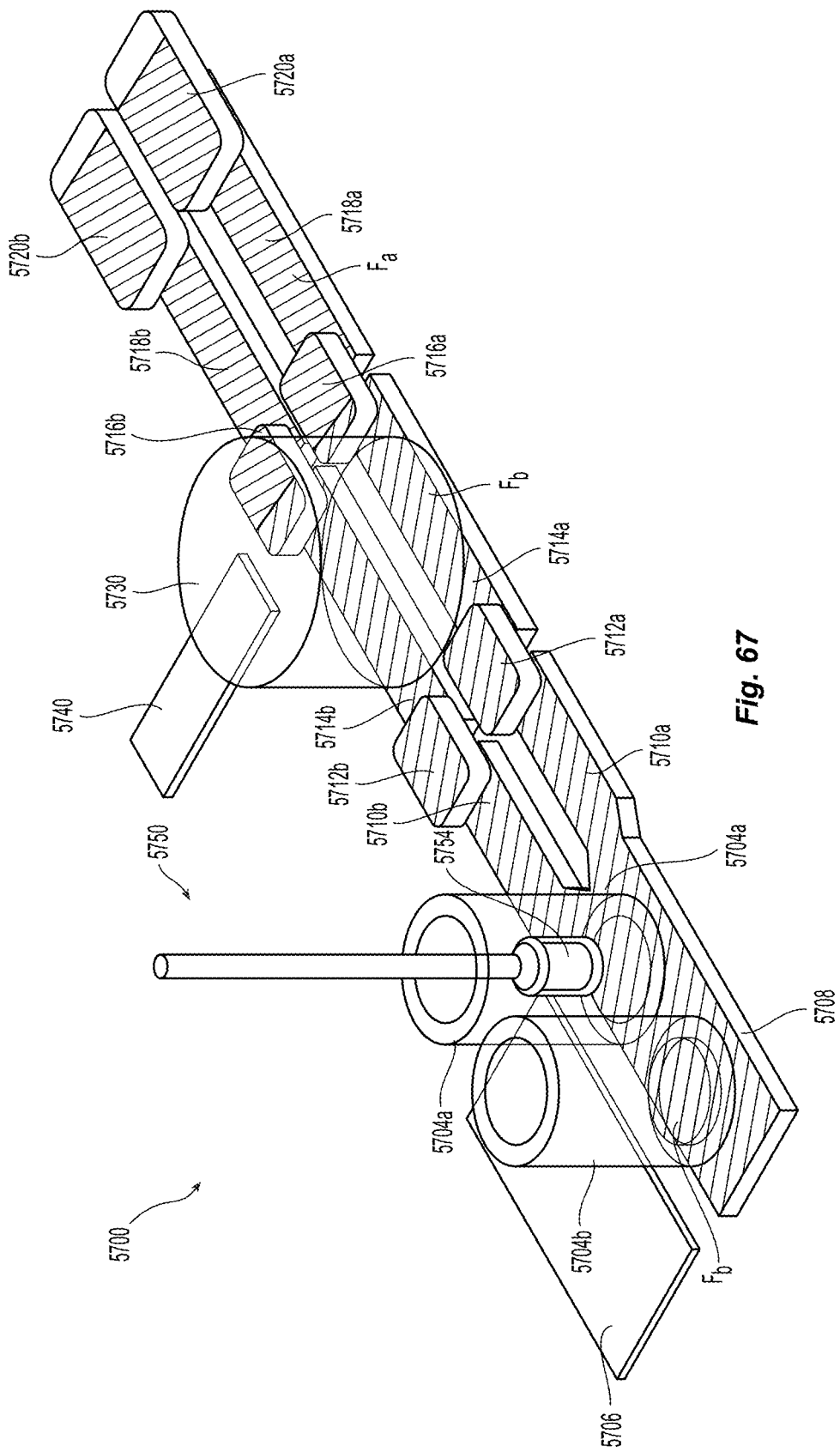
Figure 68:
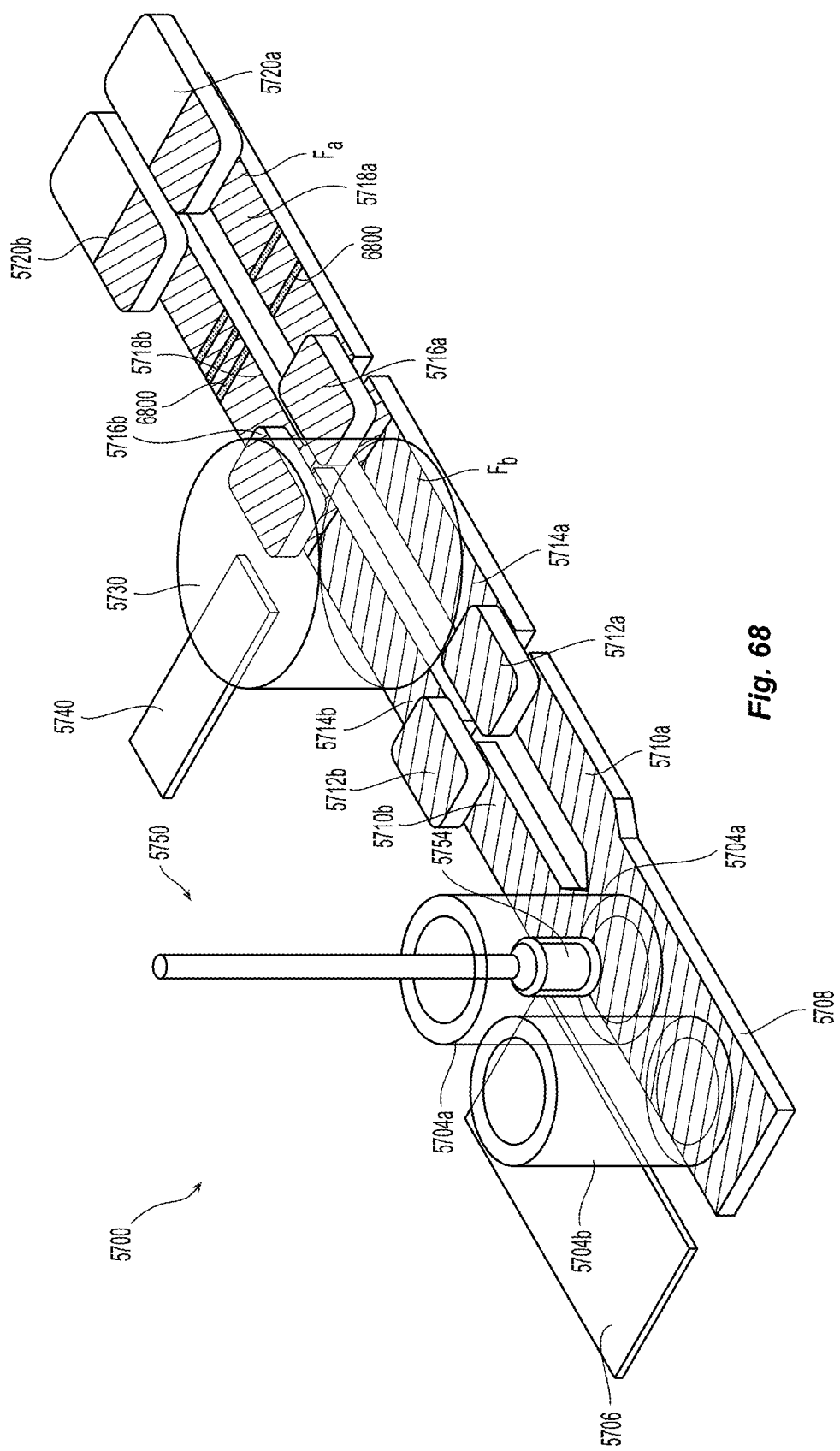

As shown in FIG. 66, the second fluid $F_b$ pushes the first fluid $F_a$ (e.g., now an amplification mixture) through the capture bead mixture in the detection pads 5716a, 5716b, thereby hydrating it. As shown in FIG. 67, the first fluid mixture then flows across the detection legs 5718a, 5718b. As shown in FIG. 68, the target and control lines 6800 are then visible in the detection legs 5718a, 5718b.

VII. EXAMPLES

1. A device comprising:
   a porous receiving element having an input region and a receiving region;
   a first fluid source configured to hold a first fluid, the first fluid source having a first outlet positioned within the input region of the receiving element; and
   a second fluid source configured to hold a second fluid, the second fluid source having a second outlet positioned within the input region of the receiving element, wherein the first outlet is positioned between the second outlet and the receiving region,
   wherein, when both the first and second fluid sources are in fluid connection with the input region, the device is configured to sequentially deliver the first fluid and the second fluid to the receiving region without leakage.

2. The device of example 1 wherein:
   the first fluid source comprises a first well having negligible capillary backpressure; and
   the second fluid source comprises a second well having negligible capillary backpressure.

3. The device of example 1 or example 2, further comprising:
   a first barrier between the first outlet and the input region; and
   a second barrier between the second outlet and the input region.

4. The device of example 3, further comprising a puncturing element configured to puncture at least one of the first barrier and the second barrier to fluidly connect the first fluid source to the input region and the second fluid source to the input region.

5. The device of example 3, wherein the first and second barriers are moveable relative to the first and second outlets.

6. The device of any one of examples 1 to 5 wherein the input region further comprises a spacer portion between the first outlet and the second outlet.

7. The device of any one of examples 1 to 6, further comprising a porous leg adjacent the receiving region of the receiving element.

8. The device of example 7, further comprising a valve positioned between the porous leg and the receiving region, wherein the valve is configured to fluidly connect the leg and the receiving region.

9. The device of example 8 wherein the valve comprises an actuatable polymer configured to expand when exposed to a particular fluid.

10. The device of example 7, further comprising a valve positioned between the porous leg and the receiving region, wherein the valve is configured to fluidly disconnect the leg and the receiving region.

11. The device of example 7, further comprising a dissolvable volume-metering element positioned between the leg and the receiving region, wherein the volume metering element is configured to provide a fluid connection between the leg and the receiving region and to at least partially dissolve and break the fluid connection between the leg and the receiving region once a predetermined volume of fluid flows therethrough.

12. The device of example 7 wherein the leg includes a plurality of capture molecules configured to selectively adhere a biological sample within the first or second fluid.

13. The device of example 7 wherein the leg has a porosity sufficiently small to trap a biological sample within the first or second fluid.

14. The device of example 7 wherein at least a portion of the porous receiving element is impregnated with a linear polysaccharide configured to bind nucleic acids in a pH-dependent manner.

15. The device of example 14 wherein the linear polysaccharide is chitin or chitosan.

16. The device of example 7 wherein at least one of the first and second fluid sources contains nucleic acid amplification agents.

17. The device of any one of examples 1 to 16 wherein at least one of the first and second fluid sources is configured to receive a biological sample.

18. The device of any one of examples 1 to 17 wherein the porous receiving element is in fluid communication with a heat source.

19. The device of any one of examples 1 to 18 wherein the device includes at least one heat source configured to deactivate ACP.

20. A method for delivering a first fluid and a second fluid to a porous receiving element, the porous receiving element having an input region and a receiving region, the method comprising:
    simultaneously fluidly connecting—
        a first fluid source to the porous receiving element at a first connection positioned within the input region, wherein the first fluid source contains a first fluid; and
        a second fluid source to the porous receiving element at a second connection positioned within the input region and between the first fluid source and the receiving region, wherein the second fluid source contains a second fluid;
    sequentially delivering the first fluid and the second fluid to the porous receiving element without the first and second fluids substantially mixing.

21. The method of example 20 wherein the first fluid has a first volume and the second fluid has a second volume, and wherein the method further comprises delivering the entire second volume to the receiving region before delivering the first fluid volume to the receiving region.

22. The method of example 20 or example 21 wherein simultaneously fluidly connecting comprises puncturing a first barrier at the first connection and puncturing a second barrier the second connection.

23. The method of any one of examples 20 to 22, further comprising fluidly connecting the receiving region to a leg adjacent the receiving region.

24. The method of example 23, wherein fluidly connecting the receiving region to the leg includes:
    positioning a polymer material between the leg and the receiving region; and
    expanding the polymer material.

25. The method of example 24 further comprising fluidly disconnecting the receiving region 26. The method of example 25 wherein fluidly disconnecting the receiving region to the leg includes:
    positioning a polymer material between the leg and the receiving region; and
    expanding the polymer material.

27. The method of any one of examples 20 to 26, further comprising positioning a dissolvable volume-metering element positioned between the leg and the receiving region.

28. A device for nucleic acid detection, comprising:
    an input zone including—
        a porous receiving element;
        a first fluid source configured to hold a first fluid, the first fluid source having a first outlet positioned adjacent the receiving element and a first inlet opposite the first outlet;
        a second fluid source configured to hold a second fluid, the second fluid source having a second outlet positioned adjacent the receiving element and a second inlet opposite the second outlet, wherein the first outlet is positioned downstream of the second outlet;
        wherein, when both the first and second fluid sources are in fluid connection with the receiving element, the device is configured to sequentially deliver the first fluid and the second fluid to the receiving element without leakage; and
        a first barrier positioned between the first and second outlets and the receiving element;
    an amplification zone downstream of the input zone, the amplification zone including—
        a porous amplification pad containing one or more substances configured to facilitate an isothermal amplification reaction, wherein the amplification pad is fluidly coupled to the receiving element;
        a heating zone, the heating zone including a heat source adjacent a porous pathway, wherein the pathway is fluidly coupled to the amplification pad; and
    a detection zone including—
        a detection pad containing one or more detection agents, the detection pad fluidly separated from the pathway by a second barrier; and
        a porous detection pathway fluidly coupled to the detection pad.

V. CONCLUSION

Any of the devices, systems and/or methods detailed above can be used for analyzing, diffusing, detecting, filtering, processing, measuring and/or separating fluid samples, solid-phase assay and selective capture and/or others. The present technology can be used to perform these processes on a microfluidic scale, and with control over fluid and reagent transport within the device and/or system.

In certain embodiments, the present disclosure is directed to devices comprised of porous wicks, which are capable of isolating and concentrating nucleic acid components of a biological sample through adsorption. In certain embodiments the nucleic acid components absorb onto chitosan or other biopolymers which are deposited onto the surface of the porous matrix or membrane. In further embodiments of this disclosure, the nucleic acid components associate and dissociate from the treated porous matrix in a pH dependent manner. Dissociated nucleic acid can then be detected or treated in other ways in other areas of the porous matrix.

In certain embodiments, this system is compatible with lateral flow in a porous wick and is based on a reversible pH-triggering method which captures the nucleic acids.

It has been found that this technique also substantially concentrates the sample resulting in a multi-purpose device where capture and concentration occur simultaneously. The synchronized combination of these events provides a unique system which can be used for a wide range of nucleic acid targets. The isolated and concentrated nucleic acids are ready to use in various downstream applications, including PCR or other methods of nucleic acid amplification, without further purification. Additionally, the release profile of nucleic acid can be tuned with this system by modulating pH. Rapid release results in highly concentrated samples while slower release allows for a more constant availability of nucleic acid. A system with this tunable nature allows for greater control of the purified NA when added into downstream applications where the concentration and timing of NA delivery is vital. These methods have been performed on commercially available membranes, such as nitrocellulose, through the adsorption of chitosan to the membranes via, for instance, ink-jet patterning. The pH-triggered release of the nucleic acids does not release the chitosan from the paper substrate. This system relies on capture of the nucleic acids on a surface due to a change in surface charge instead of the more traditional capture in solution.

The above-described devices, systems and methods of concentration can be useful for applications such as lysis, amplification and detection and any part of a diagnostic device. For example, proteins, reagents and nucleotides may be concentrated just after cell lysis. They may be also concentrated just prior to their detection (to enhance the limits of detection of a device). In yet another scenario, they may be concentrated before amplification. More importantly, this method may also be employed conjointly, combining many steps (as in one localized area) such as analyte capture along with concentration and many such processes.

The capillarity-based devices, systems and methods disclosed herein offer several advantages over conventional systems. First, conventional paper network assays require multiple fluid loading steps of specific volumes of fluid. In contrast, the present technology provides a multi-step chemical process with a single activation step. Also, the exact volume of fluid need not be added by the user to the source since the volume-metering element automatically dispenses the desired volume, regardless of the volume of fluid deposited into the source. Moreover, various methods of the present technology do not require a user to position the device in a specific orientation for operation.

Generally, devices configured in accordance with the present technology are expected to adapt the features of microfluidic devices to a porous wick (or paper) system, but without the need for external pumps, mechanical or electroosmotic, and without the need for pressure or vacuum sources to regulate the flow of fluid. Thus, no external force is necessary for the device to modulate the flow of fluid by means other than the capillary action (surface tension) of the wick and the associated absorbent pads.

In addition to the application of simple reagent loading, the present technology can be used in alternate contexts for controlling fluid volumes in paper networks. Specifically, these turn-off valves can be used further downstream in the paper network to meter volumes of reagents for interactions such as chemical dilution or reaction. Though the present technology demonstrates a range of volumes metered from about 10 µL to about 80 µL, one having skill in the art would understand how to extend this range by implementation of the volume-metering element in alternate materials and/or geometries.

The devices disclosed herein are also expected to improve the detection limits for analytes, such as simultaneous detection of two antigens from malarial parasites in blood, but at a manufacturing cost equal to that of conventional rapid diagnostic tests (RDTs). Further, results of a chemical process performed on the device can be read by eye or by cameras of mobile devices. For example, by capturing device detection spot intensities with mobile device cameras, blood antigen concentrations can be rapidly measured locally or remotely. This feature, for example, is expected to greatly aid in screening for the degree of subclinical infections at remote sites. This new approach to point-of-care diagnostics combines the sophistication of chemical processing developed in microfluidics with the simplicity and low cost of lateral flow immunoassays.

From the foregoing it will be appreciated that, although specific embodiments of the technology have been described herein for purposes of illustration, various modifications may be made without deviating from the spirit and scope of the technology. For example, the presence/configuration of the base or housing, the number of pathways, flow-metering elements, volume-metering features, the use of pre-wetted pads, the specific types of fluids, and the material choices for various components of the devices described above with reference to FIGS. 1A-70 may vary in different embodiments of the technology. Further, certain aspects of the new technology described in the context of particular embodiments may be combined or eliminated in other embodiments. For example, in the embodiments illustrated above, various combinations of flow-metering and volume-metering elements or features may be combined into a single device. Additionally, one or more pseudo-1DPN devices described above with reference to FIGS. 11-21 can be incorporated into a 2DPN device. For example, the receiving element of any of the sequential delivery devices can be in fluid communication with at least one wettably distinct pathway. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A device for nucleic acid detection, comprising:
an input zone including
a porous receiving element;
a first fluid source configured to hold a first fluid, the first fluid source having a first outlet positioned adjacent the receiving element and a first inlet opposite the first outlet;
a second fluid source configured to hold a second fluid, the second fluid source having a second outlet positioned adjacent the receiving element and a second inlet opposite the second outlet, wherein the first outlet is positioned downstream of the second outlet;
wherein, when both the first and second fluid sources are in fluid connection with the receiving element, the device is configured to sequentially deliver the first fluid and the second fluid to the receiving element without leakage; and
a first barrier positioned between the first and second outlets and the receiving element;
an amplification zone downstream of the input zone, the amplification zone including a porous amplification pad containing one or more substances configured to facilitate an isothermal amplification reaction, wherein the amplification pad is fluidly coupled to the receiving element;

a heating zone, the heating zone including a heat source adjacent a porous heating pathway, wherein the porous heating pathway is fluidly coupled to the amplification pad; and a detection zone including
  a detection pad containing one or more detection agents, the detection pad fluidly separated from the porous heating pathway by a second barrier; and
  a porous detection pathway fluidly coupled to the detection pad.

2. The device of claim 1 wherein:
the first fluid source comprises a first well having a first negligible capillary backpressure; and
the second fluid source comprises a second well having a second negligible capillary backpressure.

3. The device of claim 1 wherein at least one of the first and second fluid sources is configured to receive a biological sample.

4. The device of claim 1, further comprising a protective film removably coupled over the first inlet and the second inlet.

5. The device of claim 1 wherein the first barrier is configured to be removed to fluidly connect the first and second fluid sources to the receiving element.

6. The device of claim 1 wherein the second barrier is configured to be removed to fluidly connect the porous heating pathway to the detection pad.

7. The device of claim 1 wherein the receiving element includes a first porous receiving pathway and a second porous receiving pathway separate from the first receiving pathway.

8. The device of claim 7 wherein the porous amplification pad is a first porous amplification pad fluidly coupled to the first porous receiving pathway, and wherein the amplification zone further includes a second porous amplification pad fluidly coupled to the second porous receiving pathway.

9. The device of claim 1 wherein the porous heating pathway is a first porous heating pathway, and wherein the heating zone further includes a second porous heating pathway separate from the first porous heating pathway.

10. The device of claim 9 wherein the detection pad is a first detection pad fluidly separated from the first porous heating pathway by the second barrier, and wherein the detection zone further includes a second detection pad fluidly separated from the second porous heating pathway by the second barrier.

11. The device of claim 1 wherein the porous detection pathway is a first porous detection pathway, and wherein the detection zone further includes a second porous detection pathway separate from the first porous detection pathway.

12. The device of claim 11 wherein the detection pad is a first detection pad fluidly coupled to the first porous detection pathway, and wherein the detection zone further includes a second detection pad fluidly coupled to the second porous detection pathway.

* * * * *